US009971866B2

(12) United States Patent
Takahashi et al.

(10) Patent No.: US 9,971,866 B2
(45) Date of Patent: May 15, 2018

(54) METHOD OF EVALUATING FATTY LIVER RELATED DISEASE, FATTY LIVER RELATED DISEASE-EVALUATING APPARATUS, FATTY LIVER RELATED DISEASE-EVALUATING METHOD, FATTY LIVER RELATED DISEASE-EVALUATING PROGRAM PRODUCT, FATTY LIVER RELATED DISEASE-EVALUATING SYSTEM, INFORMATION COMMUNICATION TERMINAL APPARATUS, AND METHOD OF SEARCHING FOR PROPHYLACTIC/AMELIORATING SUBSTANCE FOR FATTY LIVER RELATED DISEASE

(71) Applicant: AJINOMOTO CO., INC., Tokyo (JP)

(72) Inventors: Mitsuo Takahashi, Kanagawa (JP);
Hiroshi Yamamoto, Kanagawa (JP);
Fumihiko Takatsuki, Kanagawa (JP);
Toshihiko Ando, Kanagawa (JP);
Minoru Yamakado, Tokyo (JP)

(73) Assignee: Ajinomoto Co., Inc., Tokyo (JP)

( * ) Notice: Subject to any disclaimer, the term of this patent is extended or adjusted under 35 U.S.C. 154(b) by 1032 days.

(21) Appl. No.: 14/140,152

(22) Filed: Dec. 24, 2013

(65) Prior Publication Data

US 2014/0113378 A1 Apr. 24, 2014

Related U.S. Application Data

(63) Continuation of application No. PCT/JP2012/066739, filed on Jun. 29, 2012.

(30) Foreign Application Priority Data

Jun. 30, 2011 (JP) .................................. 2011-146696

(51) Int. Cl.
*G01N 33/48* (2006.01)
*G06F 19/18* (2011.01)
*G01N 33/68* (2006.01)

(52) U.S. Cl.
CPC ......... *G06F 19/18* (2013.01); *G01N 33/6812* (2013.01); *G01N 2800/085* (2013.01)

(58) Field of Classification Search
CPC ...................................................... G06F 19/18
USPC ........................................................ 702/19
See application file for complete search history.

(56) References Cited

U.S. PATENT DOCUMENTS

| | | | |
|---|---|---|---|
| 6,631,330 B1 | 10/2003 | Poynard | |
| 8,234,075 B2 | 7/2012 | Kimura et al. | |
| 8,244,476 B2 | 8/2012 | Zhang et al. | |
| 2004/0039553 A1 | 2/2004 | Poynard | |
| 2005/0283347 A1 | 12/2005 | Kimura et al. | |
| 2008/0147368 A1 | 6/2008 | Sugimoto et al. | |
| 2008/0154515 A1 | 6/2008 | Zhang et al. | |
| 2009/0155826 A1 | 6/2009 | Hu et al. | |
| 2009/0253116 A1 | 10/2009 | Takahashi et al. | |
| 2010/0173348 A1 | 7/2010 | Tanaka et al. | |
| 2010/0261282 A1 | 10/2010 | Takahashi et al. | |
| 2010/0279956 A1 | 11/2010 | McCreedy, Jr. et al. | |
| 2010/0280809 A1 | 11/2010 | Takahashi et al. | |
| 2012/0041684 A1 | 2/2012 | Tanaka et al. | |
| 2012/0122981 A1 | 5/2012 | Hu et al. | |
| 2012/0239366 A1 | 9/2012 | Kimura et al. | |
| 2014/0127819 A1 | 5/2014 | Takahashi et al. | |

FOREIGN PATENT DOCUMENTS

| | | |
|---|---|---|
| EP | 2381259 A1 | 10/2011 |
| JP | 2007-315752 A | 12/2007 |
| JP | 2011-503547 A | 1/2011 |
| JP | 2011-232164 A | 11/2011 |
| JP | 2013-040923 A | 2/2013 |
| WO | WO 02/16949 A1 | 2/2002 |
| WO | WO 2004/052191 A1 | 6/2004 |
| WO | WO 2006/098192 A1 | 9/2006 |
| WO | WO 2006/129513 A1 | 12/2006 |
| WO | WO 2008/015929 A1 | 2/2008 |
| WO | WO 2009/001892 A1 | 12/2008 |
| WO | WO 2009/054350 A1 | 4/2009 |
| WO | WO 2009/054351 A1 | 4/2009 |
| WO | WO 2009/090882 A1 | 7/2009 |
| WO | WO 2010/073870 A1 | 7/2010 |
| WO | WO 2010/095682 A1 | 8/2010 |

OTHER PUBLICATIONS

"Guide for Diagnosis of NASH/NAFLD," Edited by Japan Society of Hepatology, 2010, with partial English translation of paragraphs marked with a star.
Abukawa et al., "An undescribed subset of neonatal intrahepatic cholestasis associated with multiple hyperaminoacidemia," Hepatology Research, 2001, 21:8-13.
Angulo et al., "Independent Predictors of Liver Fibrosis in Patients with Nonalcoholic Steatohepatitis," Hepatology, 1999, 30(6): 1356-1362.
Brunt et al., "Nonalcoholic Steatohepatitis: A Proposal for Grading and Staging the Histological Lesions," American Journal of Gastroenterology, 1999, 94(9):2467-2474.
Caballero et al., "Plasma amino acid concentrations in healthy elderly men and women," Am. J. Clin. Nutr., 1991, 53(5):1249-1252.

(Continued)

*Primary Examiner* — Jerry Lin
(74) *Attorney, Agent, or Firm* — Foley & Lardner LLP

(57) ABSTRACT

A method of evaluating fatty liver related disease includes (I) an obtaining step of obtaining amino acid concentration data on a concentration value of an amino acid in blood collected from a subject to be evaluated and (II) a concentration value criterion evaluating step of evaluating a state of a fatty liver related disease including at least one of fatty liver, NAFLD, and NASH in the subject, based on the amino acid concentration data of the subject obtained at the obtaining step.

33 Claims, 34 Drawing Sheets

(56) References Cited

OTHER PUBLICATIONS

Chitturi et al., "Serum Leptin in NASH Correlates with Hepatic Steatosis by Not Fibrosis: A Manisfestation of Lipotoxicity?", Hepatology, 2002, 36:403-409.

Dahlhoff et al., "Hepatic Methionine Homeostasis is Conserved in C57BL/6N Mice on High-Fat Diet Despite Major Changes in Hepatic One-Carbon Metabolism," PLOS One, Mar. 2013, 8(3):e57387, 1-13.

Dowman et al., "Systematic review: the diagnosis and staging of non-alcoholic fatty liver disease and non-alcoholic steatohepatitis," Aliment. Pharmacol. Ther., 2011, 33:525-540.

Enwonwu et al., "Accumulation of histidine, 3-methylhistidine, and homocarnosine in the brains of protein-calorie deficient monkeys," Journal of Neurochemistry, 1973, 21:799-807.

Fischer et al., "The role of plasma amino acids in hepatic encephalopathy," Surgery, Sep. 1975, 78(3):276-290.

Hakimi et al., "Phosphoenolpyruvate carboxykinase and the critical role of cataplerosis in the control of hepatic metabolism," Nutrition & Metabolism, 2005, 2:33, 1-12.

Hui et al., "Beyond Insulin Resistance in NASH: TNF-α or Adiponectin?", Hepatology, 2004, 40:46-54.

Kaneda et al., "Investigation of Predictors for Advanced Fibrosis in Nonalcoholic Fatty Liver Disease," Liver, 2004, 45(Supp.1):A316, p. 326, with English translation.

Levine et al., "Tyrosine Metabolism in Patients with Liver Disease," J. Clin. Invest., 1967, 46(12):2012-2020.

Loguercio et al., "Ethanol Consumption, Amino Acid and Glutathione Blood Levels in Patients With and Without Chronic Liver Disease," Alcoholism: Clinical and Experimental Research, Nov. 1999, 23(11):1780-1784.

Matteoni et al., "Nonalcoholic Fatty Liver Disease: A Spectrum of Clinical and Pathological Severity," Gastroenterology, 1999, 116:1413-1419.

Morgan et al., "Plasma amino-acid patterns in liver disease," Gut, 1982, 23:362-370.

Mukherjee et al., "Role of plasma amino acids and GABA in alcoholic and non-alcoholic fatty liver disease—A pilot study," Indian Journal of Clinical Biochemistry, 2010, 25(1):37-42.

Nakajima et al., "Abnormal Amino Acid Metabolism in Various Diseases and Countermeasures," Nihon Rinsho 50, 1992, 1609-1613, with English translation.

Plauth et al., "Characteristic Pattern of Free Amino Acids in Plasma and Skeletal Muscle in Stable Heaptic Cirrhosis," Hepatogastroenterol., 1990, 37:135-139.

Reid, Andrea E., "Nonalcoholic Steatohepatitis," Gastroenterology, 2001, 121:710-723.

Rosen et al., "Plasma Amino Acid Patterns in Hepatic Encephalopathy of Differing Etiology," Gastroenterology, 1977, 72(3):483-487.

Sakugawa et al., "Clinical usefulness of biochemical markers of liver fibrosis in patients with nonalcoholic fatty liver disease," World J. Gastroenterol., 2005, 11(2):255-259.

Shaw et al., "Plasma amino acid abnormalities in the alcoholic, Respective role of alcohol, nutrition, and livery injury," Gastroenterology, 1978, 74(4):677-682.

Stanko et al., "Prevention of Effects of Ethanol on Amino Acid Concentrations in Plasma and Tissues by Hepatic Lipotropic Factors in Rats," Gastroenterology, 1979, 76(1):132-138.

Sumida et al., "Serum thioredoxin levels as a predictor of steatohepatitis in patients with nonalcoholic fatty liver disease," Journal of Hepatology, 2003, 38:32-38.

Suzuki et al., "Hyaluronic acid, an accurate serum marker for severe hepatic fibrosis in patients with non-alcoholic fatty liver disease," Liver International, 2005, 25:779-786.

Takahashi et al., "'Aminoindex' and Fatty Liver (First Report) Possibility of NAFLD/NASH Discrimination," Ningen Dock, Jul. 2011, 26(2):270, with English translation.

Wu et al., "Changes in Free Amino Acids in the Plasma During Hepatic Coma," J. Clin. Invest., 1955, 34:845-849.

Zhang et al., "Plasma amino acid profiles applied for diagnosis of advanced liver fibrosis in patients with chronic hepatitis C infection," Hepatology Research, 2006, 34:170-177.

FIG.7

| USER ID | USER PASSWORD | NAME | ORGANI-ZATION ID | DEPART-MENT ID | DEPART-MENT NAME | E-MAIL ADDRESS | ... |
|---|---|---|---|---|---|---|---|
| ⋮ | ⋮ | ⋮ | ⋮ | ⋮ | ⋮ | ⋮ | ⋮ |

| INDIVIDUAL (SAMPLE) NO. | AMINO ACID CONCENTRATION DATA | | | | | |
|---|---|---|---|---|---|---|
| | Gly | Leu | Val | Ile | Phe | ... |
| U-1 | 9.5 | 11.2 | 2.7 | 8.5 | 4.9 | ... |
| U-2 | 8.5 | 10.5 | 3.9 | 9.8 | 6.1 | ... |
| ⋮ | ⋮ | ⋮ | ⋮ | ⋮ | ⋮ | ⋮ |

| INDIVIDUAL (SAMPLE) NO. | FATTY LIVER RELATED DISEASE STATE INDEX DATA (T) | | | | AMINO ACID CONCENTRATION DATA 106c | | | | | |
|---|---|---|---|---|---|---|---|---|---|---|
| | $T_1$ | $T_2$ | $T_3$ | ... | Gly | Leu | Val | Ile | Phe | ... |
| A-1 | 23.4 | 62.5 | 37.1 | ... | 9.5 | 11.2 | 2.7 | 8.5 | 4.9 | ... |
| A-2 | 27.5 | 66.1 | 39.5 | ... | 8.5 | 10.5 | 3.9 | 9.8 | 6.1 | ... |
| ... | ... | ... | ... | | | | | | | |

FIG.10

| INDIVIDUAL (SAMPLE) NO. | FATTY LIVER RELATED DISEASE STATE INDEX DATA (T) | AMINO ACID CONCENTRATION DATA | | | |
|---|---|---|---|---|---|
| | $T_2$ | Gly | Leu | Phe | ... |
| A-1 | 62.5 | 9.5 | 11.2 | 4.9 | ... |
| A-2 | 66.1 | 8.5 | 10.5 | 6.1 | ... |
| ⋮ | ⋮ | ⋮ | ⋮ | ⋮ | ⋮ |

| RANK | CANDIDATE MULTIVARIATE DISCRIMINANT |
|---|---|
| 1 | $F_1$ (Gly, Leu, Phe, ...) |
| 2 | $F_2$ (Gly, Leu, Phe, ...) |
| 3 | $F_3$ (Gly, Leu, Phe, ...) |
| ⋮ | ⋮ |

FIG.12

| RANK | CANDIDATE MULTIVARIATE DISCRIMINANT | VERIFI-CATION RESULT |
|---|---|---|
| 1 | $F_k$ (Gly, Leu, Phe, ⋯) | 1.22 |
| 2 | $F_m$ (Gly, Leu, Phe, ⋯) | 2.28 |
| 3 | $F_l$ (Gly, Leu, Phe, ⋯) | 2.95 |
| ⋮ | ⋮ | ⋮ |

FIG.13

| INDIVIDUAL (SAMPLE) NO. | FATTY LIVER RELATED DISEASE STATE INDEX DATA (T) | AMINO ACID CONCENTRATION DATA | |
|---|---|---|---|
| | $T_2$ | Leu | Phe | ⋯ |
| A-1 | 62.5 | 11.2 | 4.9 | ⋯ |
| A-2 | 66.1 | 10.5 | 6.1 | ⋯ |
| ⋮ | ⋮ | ⋮ | ⋮ | ⋮ |

FIG.14

| RANK | MULTIVARIATE DISCRIMINANT | THRESHOLD VALUE | VERIFICATION RESULT |
|---|---|---|---|
| 1 | $F_p$ (Phe, ⋯) | 0.23 | 0.62 |
| 2 | $F_p$ (Gly, Leu, Phe) | -2.12 | 1.02 |
| 3 | $F_k$ (Gly, Leu, Phe, ⋯) | 1.23 | 1.22 |
| ⋮ | ⋮ | ⋮ | ⋮ |

| INDIVIDUAL (SAMPLE) NO. | RANK | DISCRIMINANT VALUE |
|---|---|---|
| U-1 | 1 | 1.13 |
| ⋮ | ⋮ | ⋮ |

106f

| INDIVIDUAL (SAMPLE) NO. | AMINO ACID CONCENTRATION DATA | | | | DISCRIMI-NANT VALUE | EVALUATION RESULT |
|---|---|---|---|---|---|---|
| | Gly | Leu | Phe | ... | | |
| U-1 | 9.5 | 11.2 | 4.9 | ... | | |
| U-2 | 8.5 | 10.5 | 6.1 | ... | | |
| ⋮ | ⋮ | ⋮ | ⋮ | ⋮ | | |

(BASIC PRINCIPLE OF THE INVENTION)

FIG.25

| NO | FORMULA (Variable only) | ROC (Validation) | ROC (No Validation) |
|---|---|---|---|
| 1 | Ser,Glu,Gly,Ala,Val,Tyr | 0.792 | 0.796 |
| 2 | Ser,Glu,Ala,Cit,Val,Tyr | 0.791 | 0.795 |
| 3 | Ser,Glu,Ala,Val,Tyr,Orn | 0.791 | 0.795 |
| 4 | Ser,Glu,Gly,Ala,Leu,Tyr | 0.790 | 0.795 |
| 5 | Ser,Glu,Ala,Cit,Leu,Tyr | 0.790 | 0.795 |
| 6 | Ser,Glu,Ala,Val,Leu,Tyr | 0.790 | 0.795 |
| 7 | Ser,Glu,Ala,Val,Tyr,His | 0.790 | 0.794 |
| 8 | Ser,Glu,Ala,Val,Tyr,Trp | 0.790 | 0.794 |
| 9 | Thr,Ser,Glu,Ala,Val,Tyr | 0.789 | 0.794 |
| 10 | Ser,Glu,Ala,Val,Ile,Tyr | 0.789 | 0.794 |
| 11 | Ser,Glu,Ala,Cit,Ile,Tyr | 0.789 | 0.794 |
| 12 | Ser,Glu,Ala,Leu,Tyr,Orn | 0.789 | 0.793 |
| 13 | Ser,Glu,Ala,Val,Tyr | 0.789 | 0.793 |
| 14 | Ser,Glu,Pro,Ala,Val,Tyr | 0.789 | 0.793 |
| 15 | Ser,Glu,Ala,Val,Met,Tyr | 0.789 | 0.793 |
| 16 | Ser,Glu,Gly,Ala,Ile,Tyr | 0.789 | 0.793 |
| 17 | Ser,Glu,Ala,Leu,Tyr,Trp | 0.789 | 0.793 |
| 18 | Ser,Glu,Ala,Val,Tyr,Lys | 0.789 | 0.793 |
| 19 | Ser,Glu,Ala,Val,Tyr,Arg | 0.789 | 0.793 |
| 20 | Ser,Asn,Glu,Ala,Val,Tyr | 0.788 | 0.793 |
| 21 | Ser,Glu,Gln,Ala,Val,Tyr | 0.788 | 0.793 |
| 22 | Ser,Glu,Ala,ABA,Val,Tyr | 0.788 | 0.793 |
| 23 | Ser,Glu,Ala,Val,Tyr,Phe | 0.788 | 0.793 |
| 24 | Ser,Glu,Ala,Ile,Tyr,Orn | 0.788 | 0.792 |
| 25 | Ser,Glu,Ala,Ile,Leu,Tyr | 0.788 | 0.792 |
| 26 | Ser,Glu,Ala,Leu,Tyr,His | 0.788 | 0.792 |
| 27 | Thr,Ser,Glu,Ala,Leu,Tyr | 0.788 | 0.792 |
| 28 | Ser,Glu,Ala,Leu,Tyr | 0.788 | 0.791 |
| 29 | Ser,Glu,Ala,Met,Leu,Tyr | 0.788 | 0.792 |
| 30 | Ser,Glu,Pro,Ala,Leu,Tyr | 0.787 | 0.792 |
| 31 | Ser,Asn,Glu,Ala,Leu,Tyr | 0.787 | 0.792 |
| 32 | Ser,Glu,Gly,Ala,Tyr,Trp | 0.787 | 0.791 |
| 33 | Ser,Glu,Gln,Ala,Leu,Tyr | 0.787 | 0.791 |
| 34 | Ser,Glu,Ala,Leu,Tyr,Arg | 0.787 | 0.791 |
| 35 | Ser,Glu,Ala,Ile,Tyr,His | 0.787 | 0.791 |
| 36 | Ser,Glu,Ala,Leu,Tyr,Phe | 0.787 | 0.791 |
| 37 | Thr,Glu,Gly,Ala,Val,Tyr | 0.787 | 0.791 |
| 38 | Ser,Glu,Ala,Leu,Tyr,Lys | 0.787 | 0.791 |
| 39 | Ser,Glu,Ala,ABA,Leu,Tyr | 0.787 | 0.791 |
| 40 | Ser,Glu,Ala,Ile,Tyr,Trp | 0.787 | 0.791 |
| 41 | Ser,Glu,Gly,Ala,Tyr,His | 0.787 | 0.791 |
| 42 | Ser,Glu,Gly,Ala,Cit,Tyr | 0.786 | 0.791 |
| 43 | Ser,Glu,Gly,Ala,Met,Tyr | 0.786 | 0.791 |
| 44 | Ser,Glu,Gly,Ala,Val,Met | 0.786 | 0.790 |
| 45 | Glu,Gly,Ala,Cit,Val,Tyr | 0.786 | 0.790 |
| 46 | Glu,Gly,Ala,Val,Tyr,Orn | 0.786 | 0.790 |
| 47 | Ser,Glu,Ala,Cit,Tyr,Trp | 0.786 | 0.790 |
| 48 | Ser,Glu,Ala,Met,Ile,Tyr | 0.786 | 0.790 |
| 49 | Asn,Glu,Gly,Ala,Val,Tyr | 0.786 | 0.790 |
| 50 | Glu,Gly,Ala,Val,Tyr,Trp | 0.786 | 0.790 |

FIG.26

| NO | FORMULA (Variable only) | ROC (Validation) | ROC (No Validation) |
|---|---|---|---|
| 51 | Ser,Glu,Pro,Ala,Ile,Tyr | 0.785 | 0.790 |
| 52 | Glu,Gly,Ala,Val,Leu,Tyr | 0.785 | 0.790 |
| 53 | Ser,Glu,Cit,Val,Tyr,His | 0.785 | 0.790 |
| 54 | Ser,Glu,Ala,Ile,Tyr,Lys | 0.785 | 0.790 |
| 55 | Ser,Glu,Ala,Ile,Tyr | 0.785 | 0.789 |
| 56 | Ser,Glu,Gly,Ala,Tyr,Orn | 0.785 | 0.790 |
| 57 | Glu,Gly,Ala,Val,Tyr,His | 0.785 | 0.790 |
| 58 | Ser,Glu,Cit,Val,Met,Tyr | 0.785 | 0.789 |
| 59 | Ser,Glu,Gly,Ala,Val,His | 0.785 | 0.790 |
| 60 | Thr,Ser,Glu,Ala,Ile,Tyr | 0.785 | 0.790 |
| 61 | Ser,Glu,Ala,Tyr,Trp,Orn | 0.785 | 0.789 |
| 62 | Ser,Glu,Gly,Ala,Tyr | 0.785 | 0.789 |
| 63 | Ser,Glu,Ala,Tyr,His,Trp | 0.785 | 0.789 |
| 64 | Ser,Glu,Ala,Ile,Tyr,Arg | 0.785 | 0.789 |
| 65 | Ser,Glu,Ala,Ile,Tyr,Phe | 0.785 | 0.789 |
| 66 | Ser,Asn,Glu,Ala,Ile,Tyr | 0.785 | 0.789 |
| 67 | Ser,Glu,Ala,Cit,Met,Tyr | 0.785 | 0.789 |
| 68 | Glu,Gly,Ala,Val,Ile,Tyr | 0.785 | 0.789 |
| 69 | Ser,Glu,Gln,Ala,Ile,Tyr | 0.785 | 0.789 |
| 70 | Ser,Glu,Gly,Ala,Tyr,Lys | 0.785 | 0.789 |
| 71 | Thr,Glu,Gly,Ala,Leu,Tyr | 0.785 | 0.789 |
| 72 | Ser,Glu,Gly,Ala,Met,Leu | 0.785 | 0.789 |
| 73 | Ser,Glu,Ala,ABA,Ile,Tyr | 0.785 | 0.789 |
| 74 | Ser,Glu,Gly,Ala,Tyr,Arg | 0.785 | 0.789 |
| 75 | Ser,Glu,Cit,Val,Leu,Tyr | 0.785 | 0.789 |
| 76 | Ser,Glu,Gly,Ala,Tyr,Phe | 0.785 | 0.789 |
| 77 | Ser,Glu,Gly,Ala,Val,Leu | 0.785 | 0.789 |
| 78 | Ser,Glu,Cit,Val,Tyr,Trp | 0.785 | 0.789 |
| 79 | Ser,Glu,Pro,Gly,Ala,Tyr | 0.784 | 0.789 |
| 80 | Ser,Glu,Gly,Ala,Met,Ile | 0.784 | 0.789 |
| 81 | Ser,Glu,Cit,Val,Ile,Tyr | 0.784 | 0.789 |
| 82 | Ser,Glu,Ala,Cit,Tyr,His | 0.784 | 0.789 |
| 83 | Ser,Asn,Glu,Gly,Ala,Tyr | 0.784 | 0.789 |
| 84 | Ser,Glu,Gly,Ala,Val,Trp | 0.784 | 0.789 |
| 85 | Glu,Gly,Ala,Val,Tyr | 0.784 | 0.788 |
| 86 | Ser,Glu,Gln,Gly,Ala,Tyr | 0.784 | 0.789 |
| 87 | Ser,Glu,Gly,Ala,Val,Ile | 0.784 | 0.789 |
| 88 | Glu,Gly,Ala,Cit,Ile,Tyr | 0.784 | 0.789 |
| 89 | Ser,Glu,Gly,Ala,ABA,Tyr | 0.784 | 0.789 |
| 90 | Ser,Glu,Gly,Ala,Ile,His | 0.784 | 0.789 |
| 91 | Glu,Gly,Ala,ABA,Val,Tyr | 0.784 | 0.789 |
| 92 | Glu,Gly,Ala,Ile,Tyr,Orn | 0.784 | 0.788 |
| 93 | Glu,Gly,Ala,Leu,Tyr,Trp | 0.784 | 0.788 |
| 94 | Glu,Pro,Gly,Ala,Val,Tyr | 0.784 | 0.788 |
| 95 | Glu,Gly,Ala,Cit,Leu,Tyr | 0.784 | 0.788 |
| 96 | Ser,Glu,Gly,Ala,Val,Phe | 0.784 | 0.788 |
| 97 | Ser,Glu,Val,Tyr,His,Orn | 0.784 | 0.788 |
| 98 | Ser,Glu,Gly,Val,Tyr,His | 0.784 | 0.788 |
| 99 | Glu,Gly,Ala,Val,Tyr,Arg | 0.784 | 0.788 |
| 100 | Glu,Gly,Ala,Val,Tyr,Lys | 0.784 | 0.788 |

FIG.27

| NO | FORMULA | ROC (Validation) | ROC (No Validation) |
|---|---|---|---|
| 1 | (Glu+Tyr)/(Asn+Cit)+(Ala+Val)/(Ser+Gly) | 0.781 | 0.784 |
| 2 | (Glu+Tyr)/(Cit+Ser)+(Ala+Leu)/(Gln+Gly) | 0.780 | 0.784 |
| 3 | (Glu+Tyr)/(Asn+Cit)+(Ala+Leu)/(Ser+Gly) | 0.780 | 0.783 |
| 4 | (Glu+Tyr)/(Asn+Cit)+(Ala+Ile)/(Ser+Gly) | 0.780 | 0.783 |
| 5 | (Glu+Tyr)/(Cit+Ser)+(Ala+Ile)/(Gln+Gly) | 0.779 | 0.783 |
| 6 | (Glu+Tyr)/(Cit+Ser)+(Ala+Val)/(Gln+Gly) | 0.778 | 0.783 |
| 7 | (Glu+Tyr)/(Asn+Cit)+(Ala+Trp)/(Ser+Gly) | 0.778 | 0.781 |
| 8 | (Ala)/(Orn+Gln+Gly)+(Glu+Tyr)/(Cit+Ser) | 0.778 | 0.782 |
| 9 | (Glu+Tyr)/(Asn+Cit)+(Ala+Arg)/(Ser+Gly) | 0.778 | 0.781 |
| 10 | (Glu+Tyr)/(Cit+Ser)+(Ala+Met)/(Gln+Gly) | 0.778 | 0.782 |
| 11 | (Ala)/(Gln+Thr+Gly)+(Glu+Tyr)/(Cit+Ser) | 0.778 | 0.782 |
| 12 | (Glu+Tyr)/(Cit+Ser)+(Ala+Trp)/(Gln+Gly) | 0.778 | 0.782 |
| 13 | (Glu+Tyr)/(Asn+Cit)+(Ala+His)/(Ser+Gly) | 0.778 | 0.781 |
| 14 | (Ala)/(Asn+Gln+Gly)+(Glu+Tyr)/(Cit+Ser) | 0.778 | 0.782 |
| 15 | (Glu+Tyr)/(Cit+Ser)+(Ile+Met)/(Orn+Gly) | 0.778 | 0.783 |
| 16 | (Ala)/(Gln+Gly)+(Glu+Tyr)/(Cit+Ser) | 0.778 | 0.781 |
| 17 | (Glu+Tyr)/(Cit+Ser)+(Ala+His)/(Gln+Gly) | 0.778 | 0.781 |
| 18 | (Ile)/(Gly)+(Glu+Tyr+Met)/(Orn+Cit+Ser) | 0.778 | 0.783 |
| 19 | (Glu+Tyr)/(Ser)+(Ala+Ile)/(Orn+Cit+Gly) | 0.777 | 0.781 |
| 20 | (Glu+Tyr)/(Asn+Cit)+(Ala+Phe)/(Ser+Gly) | 0.777 | 0.780 |
| 21 | (Glu+Tyr)/(Asn+Cit)+(Ala+Met)/(Ser+Gly) | 0.777 | 0.780 |
| 22 | (Ala)/(Gln+Gly)+(Glu+Tyr+Met)/(Cit+Ser) | 0.777 | 0.781 |
| 23 | (Glu+Met)/(Asn+Cit)+(Ala+Tyr)/(Ser+Gly) | 0.777 | 0.780 |
| 24 | (Glu+Tyr)/(Ser)+(Ala+Leu)/(Orn+Asn+Gly) | 0.777 | 0.781 |
| 25 | (Glu+Tyr)/(Cit+Ser)+(Ala+ABA)/(Gln+Gly) | 0.777 | 0.781 |
| 26 | (Glu+Tyr)/(Ser)+(Ala+Leu)/(Orn+Cit+Gly) | 0.777 | 0.781 |
| 27 | (Glu+Tyr)/(Cit+Ser)+(Ala+Arg)/(Gln+Gly) | 0.777 | 0.781 |
| 28 | (Glu+Tyr)/(Cit+Ser)+(Ala+Phe)/(Gln+Gly) | 0.777 | 0.781 |
| 29 | (Ile)/(Orn+Gly)+(Glu+Tyr+Met)/(Cit+Ser) | 0.777 | 0.782 |
| 30 | (Ala)/(Gln+Gly)+(Glu+Tyr)/(Asn+Cit+Ser) | 0.777 | 0.780 |
| 31 | (Glu+Tyr)/(Ser)+(Ala+Leu)/(Asn+Cit+Gly) | 0.777 | 0.781 |
| 32 | (Glu+Tyr)/(Ser)+(Ala+Ile)/(Orn+Asn+Gly) | 0.777 | 0.780 |
| 33 | (Glu+Tyr)/(Ser)+(Ala+Ile)/(Asn+Cit+Gly) | 0.777 | 0.780 |
| 34 | (Glu)/(Asn+Cit)+(Ala+Tyr+Ile)/(Ser+Gly) | 0.777 | 0.780 |
| 35 | (Glu+Met)/(Gly)+(Tyr+Ile)/(Orn+Cit+Ser) | 0.776 | 0.782 |
| 36 | (Ala)/(Orn+Asn+Cit+Gly)+(Glu+Tyr)/(Ser) | 0.776 | 0.780 |
| 37 | (Glu+Met)/(Asn+Cit)+(Ala+Ile)/(Ser+Gly) | 0.776 | 0.779 |
| 38 | (Glu+Tyr)/(Ser)+(Ala+Val)/(Orn+Thr+Gly) | 0.776 | 0.781 |
| 39 | (Glu+Tyr)/(Cit+Ser)+(Ile+Met)/(Asn+Gly) | 0.776 | 0.782 |
| 40 | (Glu+Tyr)/(Ser)+(Ala+Leu)/(Thr+Cit+Gly) | 0.776 | 0.781 |
| 41 | (Glu+Tyr)/(Asn+Ser)+(Ala+Leu)/(Gln+Gly) | 0.776 | 0.780 |
| 42 | (Glu+Tyr)/(Ser)+(Ala+Val)/(Thr+Cit+Gly) | 0.776 | 0.781 |
| 43 | (Glu+Met)/(Asn+Cit)+(Ala+Leu)/(Ser+Gly) | 0.776 | 0.780 |
| 44 | (Ile)/(Asn+Gly)+(Glu+Tyr+Met)/(Cit+Ser) | 0.776 | 0.782 |
| 45 | (Ala)/(Ser+Gly)+(Glu+Tyr)/(Asn+Cit) | 0.776 | 0.779 |
| 46 | (Ile)/(Gly)+(Glu+Tyr+Met)/(Cit+Ser) | 0.776 | 0.782 |
| 47 | (Tyr)/(Gly)+(Glu+Ile+Met)/(Orn+Cit+Ser) | 0.776 | 0.782 |
| 48 | (Glu+Tyr)/(Cit+Ser)+(Ile+His)/(Orn+Gly) | 0.776 | 0.781 |
| 49 | (Ala)/(Ser+Gly)+(Glu+Tyr+Met)/(Asn+Cit) | 0.776 | 0.779 |
| 50 | (Glu+Tyr)/(Cit+Ser)+(Ile+Trp)/(Orn+Gly) | 0.776 | 0.782 |

FIG.28

| NO | FORMULA | ROC (Validation) | ROC (No Validation) |
|---|---|---|---|
| 51 | (Glu+Tyr)/(Orn+Asn)+(Ala+Val)/(Ser+Gly) | 0.776 | 0.780 |
| 52 | (Glu+Tyr)/(Orn+Ser)+(Ile+Met)/(Cit+Gly) | 0.776 | 0.781 |
| 53 | (Glu+Tyr)/(Ser)+(Ala+Leu)/(Orn+Thr+Gly) | 0.776 | 0.781 |
| 54 | (Ile)/(Asn+Gly)+(Glu+Tyr)/(Orn+Cit+Ser) | 0.776 | 0.781 |
| 55 | (Glu+Met)/(Asn+Cit)+(Ala+Val)/(Ser+Gly) | 0.776 | 0.780 |
| 56 | (Glu)/(Asn+Cit)+(Ala+Tyr+Leu)/(Ser+Gly) | 0.776 | 0.780 |
| 57 | (Ala)/(Orn+Thr+Gly)+(Glu+Tyr)/(Cit+Ser) | 0.776 | 0.780 |
| 58 | (Glu+Tyr)/(Ser)+(Ala+Val)/(Orn+Asn+Gly) | 0.776 | 0.780 |
| 59 | (Glu)/(Orn+Cit)+(Ala+Tyr+Ile)/(Ser+Gly) | 0.776 | 0.779 |
| 60 | (Glu+Tyr)/(Asn+Cit)+(Ala+ABA)/(Ser+Gly) | 0.776 | 0.779 |
| 61 | (Glu+Tyr)/(Ser)+(Ala+Val)/(Orn+Cit+Gly) | 0.776 | 0.780 |
| 62 | (Glu+Tyr)/(Ser)+(Ala+Ile)/(Thr+Cit+Gly) | 0.776 | 0.780 |
| 63 | (Glu+Met)/(Cit+Ser)+(Tyr+Ile)/(Orn+Gly) | 0.776 | 0.781 |
| 64 | (Leu)/(Orn+Gly)+(Glu+Tyr+Met)/(Cit+Ser) | 0.776 | 0.782 |
| 65 | (Glu)/(Asn+Cit)+(Ala+Tyr+Trp)/(Ser+Gly) | 0.776 | 0.779 |
| 66 | (Glu+Tyr)/(Orn+Ser)+(Ala+Leu)/(Gln+Gly) | 0.775 | 0.780 |
| 67 | (Glu+Tyr)/(Orn+Asn)+(Ala+Leu)/(Ser+Gly) | 0.775 | 0.779 |
| 68 | (Glu+Tyr)/(Ser)+(Ala+Val)/(Asn+Cit+Gly) | 0.775 | 0.780 |
| 69 | (Glu+Tyr)/(Ser)+(Ala+Met)/(Asn+Cit+Gly) | 0.775 | 0.779 |
| 70 | (Glu+Tyr)/(Ser)+(Ala+Met)/(Orn+Asn+Gly) | 0.775 | 0.779 |
| 71 | (Glu+Tyr)/(Ser)+(Ala+Ile)/(Orn+Thr+Gly) | 0.775 | 0.780 |
| 72 | (Glu+Tyr)/(Orn+Cit+Ser)+(Ile+Met)/(Gly) | 0.775 | 0.781 |
| 73 | (Glu)/(Gly)+(Tyr+Ile+Met)/(Orn+Cit+Ser) | 0.775 | 0.781 |
| 74 | (Glu+Tyr)/(Asn+Ser)+(Ala+Ile)/(Gln+Gly) | 0.775 | 0.779 |
| 75 | (Glu+Tyr)/(Ser)+(Ala+Met)/(Orn+Cit+Gly) | 0.775 | 0.779 |
| 76 | (Glu)/(Asn+Cit)+(Ala+Tyr+Met)/(Ser+Gly) | 0.775 | 0.778 |
| 77 | (Glu+Tyr)/(Orn+Ser)+(Ala+Ile)/(Gln+Gly) | 0.775 | 0.779 |
| 78 | (Glu+Ile)/(Ser)+(Ala+Tyr)/(Orn+Cit+Gly) | 0.775 | 0.779 |
| 79 | (Glu+Tyr)/(Cit+Ser)+(Ile+Met)/(Thr+Gly) | 0.775 | 0.781 |
| 80 | (Glu+Met)/(Ser)+(Ala+Tyr)/(Orn+Asn+Gly) | 0.775 | 0.778 |
| 81 | (Ile)/(Thr+Gly)+(Glu+Tyr)/(Orn+Cit+Ser) | 0.775 | 0.781 |
| 82 | (Glu+Tyr)/(Cit+Ser)+(Ile+Met)/(Gly) | 0.775 | 0.781 |
| 83 | (Ile)/(Orn+Gly)+(Glu+Tyr)/(Cit+Ser) | 0.775 | 0.781 |
| 84 | (Glu+Tyr)/(Cit+Ser)+(Trp+Met)/(Orn+Gly) | 0.775 | 0.780 |
| 85 | (Glu+Tyr)/(Orn+Ser)+(Ala+Val)/(Gln+Gly) | 0.775 | 0.779 |
| 86 | (Ala)/(Asn+Thr+Gly)+(Glu+Tyr)/(Cit+Ser) | 0.775 | 0.779 |
| 87 | (Glu)/(Asn+Cit)+(Ala+Tyr+His)/(Ser+Gly) | 0.775 | 0.778 |
| 88 | (Glu)/(Gly)+(Tyr+Met)/(Orn+Cit+Ser) | 0.775 | 0.779 |
| 89 | (Glu)/(Asn+Cit)+(Ala+Tyr+Phe)/(Ser+Gly) | 0.775 | 0.778 |
| 90 | (Glu+Met)/(Ser)+(Ala+Tyr)/(Thr+Cit+Gly) | 0.775 | 0.779 |
| 91 | (Glu+Tyr)/(Ser)+(Ala+Trp)/(Asn+Cit+Gly) | 0.775 | 0.778 |
| 92 | (Glu+Met)/(Asn+Cit)+(Ala+Trp)/(Ser+Gly) | 0.775 | 0.778 |
| 93 | (Ile)/(Thr+Gly)+(Glu+Tyr+Met)/(Cit+Ser) | 0.775 | 0.781 |
| 94 | (Glu+Tyr)/(Ser)+(Ala+Trp)/(Orn+Cit+Gly) | 0.775 | 0.778 |
| 95 | (Glu+Tyr)/(Asn+Ser)+(Ala+Val)/(Gln+Gly) | 0.775 | 0.779 |
| 96 | (Glu+Tyr)/(Ser)+(Ala+His)/(Asn+Cit+Gly) | 0.775 | 0.778 |
| 97 | (Glu+Met)/(Ser)+(Ala+Tyr)/(Asn+Cit+Gly) | 0.775 | 0.778 |
| 98 | (Glu+Tyr)/(Orn+Asn)+(Ala+Ile)/(Ser+Gly) | 0.775 | 0.778 |
| 99 | (Glu+Tyr)/(Ser)+(Ala+ABA)/(Orn+Cit+Gly) | 0.775 | 0.778 |
| 100 | (Glu+Tyr)/(Ser)+(Ala+Phe)/(Orn+Cit+Gly) | 0.775 | 0.778 |

FIG.29

| NO | FORMULA(Variable only) | ROC (Validation) | ROC (No Validation) |
|---|---|---|---|
| 1 | Ser,Glu,Val,Tyr,His,Orn | 0.820 | 0.828 |
| 2 | Ser,Glu,Val,Tyr,Phe,His | 0.819 | 0.827 |
| 3 | Ser,Glu,Cit,Val,Tyr,His | 0.819 | 0.827 |
| 4 | Ser,Glu,Val,Tyr,His,Trp | 0.819 | 0.827 |
| 5 | Ser,Glu,Ala,Val,Tyr,His | 0.818 | 0.826 |
| 6 | Ser,Glu,Val,Ile,Tyr,His | 0.818 | 0.827 |
| 7 | Glu,Val,Ile,Tyr,His,Orn | 0.818 | 0.826 |
| 8 | Thr,Ser,Glu,Val,Tyr,His | 0.818 | 0.826 |
| 9 | Thr,Glu,Val,Tyr,His,Trp | 0.817 | 0.826 |
| 10 | Ser,Glu,Val,Tyr,His | 0.817 | 0.824 |
| 11 | Thr,Glu,Val,Tyr,His,Orn | 0.817 | 0.825 |
| 12 | Thr,Glu,Val,Ile,Tyr,His | 0.817 | 0.825 |
| 13 | Ser,Glu,Val,Met,Tyr,His | 0.817 | 0.825 |
| 14 | Glu,Val,Tyr,His,Trp,Orn | 0.817 | 0.825 |
| 15 | Glu,Val,Tyr,Phe,His,Orn | 0.817 | 0.825 |
| 16 | Thr,Glu,Ala,Val,Tyr,His | 0.816 | 0.825 |
| 17 | Ser,Glu,Gly,Val,Tyr,His | 0.816 | 0.825 |
| 18 | Thr,Glu,Cit,Val,Tyr,His | 0.816 | 0.825 |
| 19 | Ser,Glu,Val,Leu,Tyr,His | 0.816 | 0.825 |
| 20 | Ser,Glu,ABA,Val,Tyr,His | 0.816 | 0.825 |
| 21 | Thr,Glu,Val,Tyr,Phe,His | 0.816 | 0.824 |
| 22 | Ser,Glu,Val,Tyr,His,Lys | 0.816 | 0.824 |
| 23 | Glu,Ala,Val,Tyr,His,Orn | 0.816 | 0.824 |
| 24 | Ser,Asn,Glu,Val,Tyr,His | 0.816 | 0.824 |
| 25 | Ser,Glu,Val,Tyr,His,Arg | 0.816 | 0.824 |
| 26 | Glu,Ile,Tyr,Phe,His,Orn | 0.815 | 0.824 |
| 27 | Glu,Val,Tyr,His,Orn | 0.815 | 0.822 |
| 28 | Glu,Gly,Val,Tyr,His,Orn | 0.815 | 0.824 |
| 29 | Thr,Glu,Val,Tyr,His | 0.815 | 0.822 |
| 30 | Thr,Glu,Gly,Val,Tyr,His | 0.815 | 0.824 |
| 31 | Glu,Cit,Val,Tyr,His,Orn | 0.815 | 0.823 |
| 32 | Thr,Glu,Val,Leu,Tyr,His | 0.815 | 0.823 |
| 33 | Thr,Glu,ABA,Val,Tyr,His | 0.815 | 0.823 |
| 34 | Glu,ABA,Val,Tyr,His,Orn | 0.815 | 0.823 |
| 35 | Glu,Gly,Ala,Val,Tyr,His | 0.815 | 0.823 |
| 36 | Asn,Glu,Val,Tyr,His,Orn | 0.815 | 0.823 |
| 37 | Glu,Cit,Val,Ile,Tyr,His | 0.815 | 0.823 |
| 38 | Glu,Gly,Val,Tyr,His,Trp | 0.815 | 0.823 |
| 39 | Ser,Glu,Pro,Val,Tyr,His | 0.814 | 0.823 |
| 40 | Glu,Cit,Val,Tyr,His,Trp | 0.814 | 0.822 |
| 41 | Glu,Cit,Val,Tyr,Phe,His | 0.814 | 0.822 |
| 42 | Ser,Glu,Ile,Tyr,His,Orn | 0.814 | 0.823 |
| 43 | Glu,Gly,Val,Ile,Tyr,His | 0.814 | 0.823 |
| 44 | Glu,Val,Ile,Tyr,His,Trp | 0.814 | 0.822 |
| 45 | Ser,Glu,Ile,Tyr,Phe,His | 0.814 | 0.823 |
| 46 | Glu,Val,Tyr,His,Orn,Arg | 0.814 | 0.822 |
| 47 | Thr,Asn,Glu,Val,Tyr,His | 0.814 | 0.822 |
| 48 | Glu,Gly,Cit,Val,Tyr,His | 0.814 | 0.822 |
| 49 | Glu,Val,Leu,Tyr,His,Orn | 0.814 | 0.822 |
| 50 | Ser,Glu,Val,Tyr,Phe,Orn | 0.814 | 0.821 |

FIG.30

| NO | FORMULA(Variable only) | ROC (Validation) | ROC (No Validation) |
|---|---|---|---|
| 51 | Thr,Glu,Val,Tyr,His,Lys | 0.814 | 0.822 |
| 52 | Thr,Glu,Val,Met,Tyr,His | 0.814 | 0.822 |
| 53 | Glu,Cit,Ile,Tyr,Phe,His | 0.814 | 0.822 |
| 54 | Glu,Ala,Val,Tyr,His,Trp | 0.814 | 0.821 |
| 55 | Ser,Glu,Gln,Val,Tyr,His | 0.814 | 0.822 |
| 56 | Ser,Glu,Cit,Ile,Tyr,His | 0.814 | 0.822 |
| 57 | Glu,Val,Tyr,Phe,His,Trp | 0.814 | 0.822 |
| 58 | Glu,Val,Tyr,His,Orn,Lys | 0.813 | 0.822 |
| 59 | Glu,Val,Met,Tyr,His,Orn | 0.813 | 0.822 |
| 60 | Glu,Val,Ile,Tyr,Phe,His | 0.813 | 0.822 |
| 61 | Glu,Ile,Tyr,His,Trp,Orn | 0.813 | 0.822 |
| 62 | Glu,Gly,Val,Tyr,Phe,His | 0.813 | 0.821 |
| 63 | Glu,Ala,Cit,Val,Tyr,His | 0.813 | 0.821 |
| 64 | Glu,Cit,Ile,Tyr,His,Orn | 0.813 | 0.821 |
| 65 | Thr,Glu,Val,Tyr,His,Arg | 0.813 | 0.822 |
| 66 | Glu,Ala,Val,Ile,Tyr,His | 0.813 | 0.821 |
| 67 | Glu,Gly,ABA,Val,Tyr,His | 0.813 | 0.822 |
| 68 | Glu,Cit,ABA,Val,Tyr,His | 0.813 | 0.821 |
| 69 | Asn,Glu,Val,Tyr,His,Trp | 0.813 | 0.821 |
| 70 | Glu,Ala,Ile,Tyr,His,Orn | 0.813 | 0.821 |
| 71 | Glu,Val,Tyr,His,Trp | 0.813 | 0.819 |
| 72 | Glu,Ala,Val,Tyr,Phe,His | 0.813 | 0.821 |
| 73 | Glu,Val,Ile,Tyr,Phe,Orn | 0.813 | 0.821 |
| 74 | Glu,ABA,Val,Ile,Tyr,His | 0.813 | 0.821 |
| 75 | Thr,Glu,Pro,Val,Tyr,His | 0.813 | 0.821 |
| 76 | Glu,Val,Ile,Tyr,His | 0.813 | 0.820 |
| 77 | Glu,Cit,Val,Tyr,His | 0.812 | 0.820 |
| 78 | Asn,Glu,Cit,Val,Tyr,His | 0.812 | 0.821 |
| 79 | Ser,Glu,Ile,Tyr,His,Trp | 0.812 | 0.821 |
| 80 | Glu,Gly,Val,Tyr,His | 0.812 | 0.820 |
| 81 | Glu,ABA,Ile,Tyr,His,Orn | 0.812 | 0.821 |
| 82 | Asn,Glu,Val,Ile,Tyr,His | 0.812 | 0.821 |
| 83 | Glu,ABA,Val,Tyr,His,Trp | 0.812 | 0.820 |
| 84 | Ser,Glu,Ala,Val,Tyr,Orn | 0.812 | 0.820 |
| 85 | Thr,Glu,Gln,Val,Tyr,His | 0.812 | 0.821 |
| 86 | Thr,Glu,Cit,Ile,Tyr,His | 0.812 | 0.821 |
| 87 | Thr,Glu,Ile,Tyr,His,Orn | 0.812 | 0.821 |
| 88 | Glu,Cit,Ile,Tyr,His,Trp | 0.812 | 0.820 |
| 89 | Glu,Val,Tyr,Phe,Trp,Orn | 0.812 | 0.820 |
| 90 | Thr,Glu,Ile,Tyr,His,Trp | 0.812 | 0.820 |
| 91 | Glu,Ala,Val,Tyr,His | 0.812 | 0.819 |
| 92 | Glu,Ala,Val,Tyr,Phe,Orn | 0.812 | 0.819 |
| 93 | Glu,Gln,Val,Tyr,His,Orn | 0.812 | 0.820 |
| 94 | Asn,Glu,Ala,Val,Tyr,His | 0.812 | 0.820 |
| 95 | Glu,ABA,Val,Tyr,Phe,His | 0.812 | 0.820 |
| 96 | Thr,Glu,Ile,Tyr,Phe,His | 0.812 | 0.821 |
| 97 | Glu,Pro,Val,Tyr,His,Orn | 0.812 | 0.820 |
| 98 | Ser,Glu,Val,Tyr,Trp,Orn | 0.812 | 0.819 |
| 99 | Glu,Ile,Tyr,His,Orn | 0.812 | 0.819 |
| 100 | Ser,Glu,Tyr,Phe,His,Trp | 0.812 | 0.820 |

FIG.31

| NO | FORMULA | ROC (Validation) | ROC (No Validation) |
|---|---|---|---|
| 1 | (Glu+Met)/(Ser+Cit)+(Tyr+His)/(Orn+Gly) | 0.799 | 0.799 |
| 2 | (Glu+Tyr)/(Asn+Orn+Cit)+(Ile+His)/(Gly) | 0.798 | 0.796 |
| 3 | (Val)/(Ser+Gly)+(Glu+Tyr)/(Asn+Orn+Cit) | 0.798 | 0.797 |
| 4 | (Val)/(Gln+Gly)+(Glu+Tyr)/(Orn+Ser+Cit) | 0.798 | 0.800 |
| 5 | (His)/(Gly)+(Glu+Tyr+Met)/(Asn+Ser+Cit) | 0.797 | 0.797 |
| 6 | (Phe)/(Gly)+(Glu+Tyr+Met)/(Orn+Ser+Cit) | 0.797 | 0.798 |
| 7 | (Glu)/(Gly)+(Tyr+His)/(Asn+Orn+Ser+Cit) | 0.797 | 0.795 |
| 8 | (Tyr)/(Gly)+(Glu+His+Met)/(Asn+Ser+Cit) | 0.797 | 0.797 |
| 9 | (Glu+Tyr)/(Asn+Cit)+(Val+Ala)/(Ser+Gly) | 0.797 | 0.794 |
| 10 | (Glu+Tyr)/(Asn+Cit)+(Val+His)/(Orn+Gly) | 0.797 | 0.795 |
| 11 | (Glu+His)/(Orn+Ser+Cit)+(Tyr+Met)/(Gly) | 0.796 | 0.795 |
| 12 | (Glu+Tyr)/(Asn+Cit)+(Val+His)/(Ser+Gly) | 0.796 | 0.796 |
| 13 | (Glu+Met)/(Ser+Cit)+(Tyr+Phe)/(Orn+Gly) | 0.796 | 0.799 |
| 14 | (Glu+Tyr)/(Asn+Orn+Cit)+(Ile+Phe)/(Gly) | 0.796 | 0.796 |
| 15 | (Glu+Tyr)/(Ser+Cit)+(Ile+His)/(Orn+Gly) | 0.796 | 0.798 |
| 16 | (Tyr)/(Gly)+(Glu+His)/(Asn+Orn+Ser+Cit) | 0.796 | 0.795 |
| 17 | (Tyr)/(Gly)+(Glu+His+Met)/(Orn+Ser+Cit) | 0.796 | 0.796 |
| 18 | (Glu+His)/(Asn+Ser+Cit)+(Tyr+Met)/(Gly) | 0.796 | 0.795 |
| 19 | (Glu+Tyr)/(Asn+Ser+Cit)+(His+Met)/(Gly) | 0.796 | 0.795 |
| 20 | (Glu+Tyr)/(Orn+Ser)+(Ile+His)/(Cit+Gly) | 0.796 | 0.796 |
| 21 | (His)/(Gly)+(Glu+Tyr+Met)/(Orn+Ser+Cit) | 0.796 | 0.795 |
| 22 | (Glu+Tyr)/(Orn+Ser+Cit)+(His+Met)/(Gly) | 0.796 | 0.794 |
| 23 | (Glu+Ile)/(Gly)+(Tyr+His)/(Orn+Ser+Cit) | 0.796 | 0.795 |
| 24 | (Glu+Tyr)/(Asn+Orn+Cit)+(Ile+Trp)/(Gly) | 0.796 | 0.795 |
| 25 | (Glu+Tyr)/(Asn+Orn)+(Val+His)/(Ser+Gly) | 0.796 | 0.794 |
| 26 | (Glu+Tyr)/(Orn+Ser+Cit)+(Phe+Met)/(Gly) | 0.796 | 0.796 |
| 27 | (Glu+Tyr)/(Ser+Cit)+(Phe+His)/(Orn+Gly) | 0.796 | 0.797 |
| 28 | (Tyr)/(Gly)+(Glu+Phe+Met)/(Orn+Ser+Cit) | 0.796 | 0.797 |
| 29 | (Glu+Tyr)/(Ser+Cit)+(His+Met)/(Orn+Gly) | 0.796 | 0.797 |
| 30 | (Val+His)/(Gly)+(Glu+Tyr+Met)/(Asn+Cit) | 0.796 | 0.794 |
| 31 | (Glu+Met)/(Orn+Ser)+(Tyr+His)/(Cit+Gly) | 0.795 | 0.795 |
| 32 | (Glu+Met)/(Ser+Cit)+(Tyr+Ile)/(Orn+Gly) | 0.795 | 0.798 |
| 33 | (Glu+Tyr)/(Asn+Orn)+(Val+His)/(Cit+Gly) | 0.795 | 0.793 |
| 34 | (Glu)/(Gly)+(Tyr+Met)/(Orn+Ser+Cit) | 0.795 | 0.795 |
| 35 | (Glu+Ile)/(Gly)+(Tyr+Met)/(Asn+Orn+Cit) | 0.795 | 0.792 |
| 36 | (His)/(Orn+Gly)+(Glu+Tyr)/(Asn+Ser+Cit) | 0.795 | 0.796 |
| 37 | (Glu+Tyr)/(Asn+Cit)+(Val+Phe)/(Orn+Gly) | 0.795 | 0.794 |
| 38 | (Glu+Tyr)/(Asn+Orn+Cit)+(Ile+Met)/(Gly) | 0.795 | 0.794 |
| 39 | (Met)/(Gly)+(Glu+Tyr)/(Asn+Orn+Ser+Cit) | 0.795 | 0.796 |
| 40 | (Ile)/(Gly)+(Glu+Tyr+Met)/(Orn+Ser+Cit) | 0.795 | 0.797 |
| 41 | (Glu+Met)/(Gly)+(Tyr+His)/(Orn+Ser+Cit) | 0.795 | 0.793 |
| 42 | (Glu+His)/(Asn+Orn+Cit)+(Tyr+Ile)/(Gly) | 0.795 | 0.793 |
| 43 | (Glu+Tyr)/(Gly)+(Ile+His)/(Orn+Ser+Cit) | 0.795 | 0.795 |
| 44 | (Glu+Met)/(Ser+Cit)+(Tyr+His)/(Asn+Gly) | 0.795 | 0.796 |
| 45 | (Glu+Met)/(Gly)+(Tyr+His)/(Asn+Orn+Ser) | 0.795 | 0.793 |
| 46 | (Glu+Tyr)/(Asn+Cit)+(Val+Ala)/(Orn+Gly) | 0.795 | 0.791 |
| 47 | (Glu+Tyr)/(Asn+Cit)+(Val+Trp)/(Orn+Gly) | 0.795 | 0.794 |
| 48 | (Glu+Tyr)/(Asn+Cit)+(Val+Ile)/(Orn+Gly) | 0.795 | 0.794 |
| 49 | (Glu+Met)/(Asn+Ser)+(Tyr+His)/(Orn+Gly) | 0.795 | 0.796 |
| 50 | (Glu)/(Ser+Cit)+(Tyr+His+Met)/(Orn+Gly) | 0.795 | 0.795 |

FIG.32

| NO | FORMULA | ROC (Validation) | ROC (No Validation) |
|---|---|---|---|
| 51 | (Glu+Met)/(Gly)+(Tyr+Phe)/(Orn+Ser+Cit) | 0.795 | 0.795 |
| 52 | (Tyr)/(Gly)+(Glu+His+Met)/(Asn+Orn+Ser) | 0.795 | 0.794 |
| 53 | (Glu+Tyr)/(Orn+Ser)+(Val+His)/(Gln+Gly) | 0.795 | 0.797 |
| 54 | (Glu)/(Gly)+(Tyr+Met)/(Asn+Orn+Ser+Cit) | 0.795 | 0.794 |
| 55 | (Glu+His)/(Gly)+(Tyr+Ile)/(Orn+Ser+Cit) | 0.795 | 0.794 |
| 56 | (Glu)/(Ser+Cit)+(Tyr+Ile+His)/(Orn+Gly) | 0.795 | 0.795 |
| 57 | (Glu+Tyr)/(Ser+Cit)+(Val+His)/(Orn+Gly) | 0.795 | 0.795 |
| 58 | (Ile)/(Gly)+(Glu+Tyr+His)/(Orn+Ser+Cit) | 0.795 | 0.796 |
| 59 | (Tyr)/(Gly)+(Glu+His)/(Orn+Ser+Cit) | 0.795 | 0.794 |
| 60 | (Glu+Tyr)/(Orn+Ser+Cit)+(Ile+Met)/(Gly) | 0.794 | 0.796 |
| 61 | (Val)/(Arg+Orn+Gly)+(Glu+Tyr)/(Ser+Cit) | 0.794 | 0.797 |
| 62 | (Glu+Tyr)/(Asn+Cit)+(Val+Met)/(Orn+Gly) | 0.794 | 0.794 |
| 63 | (Glu+Met)/(Asn+Ser)+(Tyr+His)/(Cit+Gly) | 0.794 | 0.795 |
| 64 | (His)/(Gly)+(Glu+Tyr+Ile)/(Orn+Ser+Cit) | 0.794 | 0.796 |
| 65 | (Tyr)/(Gly)+(Glu+Ile+Met)/(Orn+Ser+Cit) | 0.794 | 0.797 |
| 66 | (His)/(Asn+Gly)+(Glu+Tyr)/(Orn+Ser+Cit) | 0.794 | 0.794 |
| 67 | (Glu+Phe)/(Asn+Orn+Cit)+(Tyr+Ile)/(Gly) | 0.794 | 0.794 |
| 68 | (Glu+Tyr)/(Asn+Cit)+(Val+His+Met)/(Gly) | 0.794 | 0.792 |
| 69 | (Glu+Met)/(Gly)+(Tyr+Ile)/(Orn+Ser+Cit) | 0.794 | 0.796 |
| 70 | (Glu+Tyr)/(Asn+Orn)+(Val+Phe)/(Ser+Gly) | 0.794 | 0.794 |
| 71 | (Tyr)/(Orn+Ser+Cit)+(Glu+Met)/(Asn+Gly) | 0.794 | 0.793 |
| 72 | (Glu+Met)/(Gly)+(Tyr+His)/(Asn+Ser+Cit) | 0.794 | 0.793 |
| 73 | (Glu+His)/(Orn+Ser+Cit)+(Tyr+Ile)/(Gly) | 0.794 | 0.793 |
| 74 | (Glu)/(Asn+Gly)+(Tyr+Met)/(Orn+Ser+Cit) | 0.794 | 0.794 |
| 75 | (Glu+Met)/(Ser+Cit)+(Tyr+His)/(Arg+Gly) | 0.794 | 0.796 |
| 76 | (Met)/(Asn+Orn+Cit)+(Glu+Tyr)/(Ser+Gly) | 0.794 | 0.792 |
| 77 | (Glu+Tyr)/(Orn+Ser)+(Val+Ala)/(Gln+Gly) | 0.794 | 0.795 |
| 78 | (Phe)/(Gly)+(Glu+Tyr)/(Orn+Ser+Cit) | 0.794 | 0.795 |
| 79 | (Glu+His)/(Orn+Ser)+(Tyr+Ile)/(Cit+Gly) | 0.794 | 0.795 |
| 80 | (Glu+Tyr)/(Asn+Orn)+(Val+Ile)/(Ser+Gly) | 0.794 | 0.793 |
| 81 | (Glu+Tyr)/(Asn+Orn)+(Val+Trp)/(Ser+Gly) | 0.794 | 0.793 |
| 82 | (Glu+Met)/(Orn+Ser)+(Tyr+Phe)/(Cit+Gly) | 0.794 | 0.795 |
| 83 | (Glu+Tyr)/(Asn+Orn)+(Val+Ala)/(Ser+Gly) | 0.794 | 0.791 |
| 84 | (Tyr)/(Orn+Gly)+(Glu+Met)/(Asn+Ser+Cit) | 0.794 | 0.796 |
| 85 | (Glu+His)/(Asn+Orn+Ser)+(Tyr+Met)/(Gly) | 0.794 | 0.792 |
| 86 | (His)/(Gly)+(Glu+Tyr)/(Orn+Ser+Cit) | 0.794 | 0.793 |
| 87 | (Glu+Tyr)/(Ser+Cit)+(Trp+His)/(Orn+Gly) | 0.794 | 0.795 |
| 88 | (Glu+Tyr)/(Asn+Cit)+(Val+Leu)/(Orn+Gly) | 0.794 | 0.793 |
| 89 | (Glu+Tyr)/(Asn+Orn)+(Val+Ile)/(Cit+Gly) | 0.794 | 0.792 |
| 90 | (Glu+Tyr)/(Asn+Cit)+(Val+Phe)/(Ser+Gly) | 0.794 | 0.794 |
| 91 | (Glu+Met)/(Ser+Cit)+(Tyr+Trp)/(Orn+Gly) | 0.794 | 0.796 |
| 92 | (Glu+Tyr)/(Asn+Orn)+(Val+Phe)/(Cit+Gly) | 0.794 | 0.792 |
| 93 | (Glu+Tyr)/(Asn+Cit)+(Val+Leu)/(Ser+Gly) | 0.794 | 0.793 |
| 94 | (Glu+Tyr)/(Asn+Cit)+(Val+Ile)/(Ser+Gly) | 0.794 | 0.793 |
| 95 | (Ile)/(Gly)+(Glu+Tyr+Phe)/(Orn+Ser+Cit) | 0.794 | 0.796 |
| 96 | (Ile)/(Arg+Gly)+(Glu+Tyr)/(Orn+Ser+Cit) | 0.794 | 0.796 |
| 97 | (Val)/(Gln+Gly)+(Glu+Tyr)/(Asn+Orn+Ser) | 0.794 | 0.796 |
| 98 | (Val+Trp)/(Gly)+(Glu+Tyr+Met)/(Asn+Cit) | 0.794 | 0.793 |
| 99 | (Glu+Tyr)/(Orn+Ser+Cit)+(Ile+His)/(Gln) | 0.794 | 0.796 |
| 100 | (Glu+Tyr)/(Orn+Ser)+(Ile+Phe)/(Cit+Gly) | 0.794 | 0.795 |

FIG.33

| NO | FORMULA(Variable only) | ROC (Validation) | ROC (No Validation) |
|---|---|---|---|
| 1 | Glu,Gln,Ala,Val,Tyr,His | 0.847 | 0.862 |
| 2 | Glu,Gln,Ala,Tyr,Phe,His | 0.845 | 0.860 |
| 3 | Glu,Gln,Ala,Val,Tyr,Phe | 0.845 | 0.857 |
| 4 | Thr,Glu,Gln,Ala,Val,Tyr | 0.845 | 0.859 |
| 5 | Glu,Gln,Val,Tyr,Phe,His | 0.844 | 0.858 |
| 6 | Glu,Gln,Ala,Tyr,Phe | 0.843 | 0.855 |
| 7 | Glu,Gln,Ala,Val,Tyr | 0.843 | 0.854 |
| 8 | Asn,Glu,Gln,Ala,Val,Tyr | 0.843 | 0.857 |
| 9 | Thr,Glu,Gln,Val,Tyr,His | 0.843 | 0.859 |
| 10 | Thr,Glu,Ala,Val,Tyr,Phe | 0.843 | 0.859 |
| 11 | Asn,Glu,Gln,Val,Tyr,His | 0.843 | 0.857 |
| 12 | Asn,Glu,Ala,Val,Tyr,Phe | 0.843 | 0.856 |
| 13 | Glu,Gln,Ala,Tyr,His | 0.842 | 0.855 |
| 14 | Glu,Gln,Pro,Ala,Val,Tyr | 0.842 | 0.856 |
| 15 | Glu,Gln,Ala,ABA,Tyr,Phe | 0.842 | 0.856 |
| 16 | Glu,Gln,Val,Tyr,His | 0.842 | 0.855 |
| 17 | Glu,Gln,Ala,Val,Phe,His | 0.842 | 0.856 |
| 18 | Thr,Glu,Ala,Val,Tyr | 0.842 | 0.856 |
| 19 | Glu,Gln,Ala,Val,Met,Tyr | 0.842 | 0.855 |
| 20 | Glu,Gln,Gly,Ala,Val,Tyr | 0.842 | 0.857 |
| 21 | Glu,Gln,Ala,Met,Tyr,Phe | 0.842 | 0.856 |
| 22 | Ser,Glu,Gln,Val,Tyr,His | 0.841 | 0.858 |
| 23 | Glu,Gln,Ala,Val,Tyr,Orn | 0.841 | 0.855 |
| 24 | Glu,Gln,Ala,Val,Tyr,Trp | 0.841 | 0.854 |
| 25 | Glu,Gln,Ala,ABA,Val,Tyr | 0.841 | 0.855 |
| 26 | Ser,Glu,Ala,Val,Tyr,Phe | 0.841 | 0.857 |
| 27 | Thr,Glu,Gln,Ala,Tyr,Phe | 0.841 | 0.856 |
| 28 | Glu,Gln,Ala,Val,Tyr,Lys | 0.841 | 0.854 |
| 29 | Asn,Glu,Ala,Val,Tyr,His | 0.841 | 0.858 |
| 30 | Asn,Glu,Gln,Ala,Tyr,Phe | 0.841 | 0.854 |
| 31 | Thr,Glu,Ala,Val,Tyr,His | 0.841 | 0.859 |
| 32 | Glu,Gln,Ala,Tyr,Phe,Lys | 0.841 | 0.855 |
| 33 | Ser,Glu,Gln,Ala,Val,Tyr | 0.841 | 0.856 |
| 34 | Asn,Glu,Ala,Val,Tyr | 0.841 | 0.853 |
| 35 | Glu,Gln,Ala,Val,Leu,Tyr | 0.841 | 0.855 |
| 36 | Glu,Gln,Ala,Cit,Val,Tyr | 0.841 | 0.855 |
| 37 | Glu,Gln,Ala,Cit,Tyr,Phe | 0.841 | 0.855 |
| 38 | Glu,Gln,Val,Met,Tyr,His | 0.841 | 0.855 |
| 39 | Glu,Gln,Pro,Ala,Tyr,Phe | 0.841 | 0.855 |
| 40 | Glu,Gln,Val,Tyr,His,Orn | 0.841 | 0.855 |
| 41 | Glu,Gln,ABA,Val,Tyr,His | 0.840 | 0.856 |
| 42 | Glu,Gln,Ala,Tyr,Phe,Orn | 0.840 | 0.854 |
| 43 | Glu,Gln,Val,Tyr,His,Lys | 0.840 | 0.856 |
| 44 | Glu,Gln,Ala,Leu,Tyr,Phe | 0.840 | 0.853 |
| 45 | Glu,Ala,Val,Tyr,Phe | 0.840 | 0.853 |
| 46 | Ser,Glu,Gln,Ala,Tyr,Phe | 0.840 | 0.856 |
| 47 | Glu,Gln,Ala,Val,Tyr,Arg | 0.840 | 0.854 |
| 48 | Glu,Ala,Val,Tyr,Phe,Orn | 0.840 | 0.855 |
| 49 | Glu,Gln,Val,Tyr,His,Trp | 0.840 | 0.854 |
| 50 | Glu,Gln,Ala,Leu,Tyr,His | 0.840 | 0.855 |

FIG.34

| NO | FORMULA(Variable only) | ROC (Validation) | ROC (No Validation) |
|---|---|---|---|
| 51 | Thr,Glu,Ala,Val,Tyr,Orn | 0.840 | 0.856 |
| 52 | Glu,Gln,Gly,Ala,Tyr,His | 0.840 | 0.857 |
| 53 | Glu,Gln,Gly,Ala,Tyr,Phe | 0.840 | 0.855 |
| 54 | Thr,Glu,Ala,Val,Ile,Tyr | 0.840 | 0.856 |
| 55 | Thr,Asn,Glu,Ala,Val,Tyr | 0.840 | 0.856 |
| 56 | Glu,Gln,Ala,Tyr,Phe,Arg | 0.840 | 0.855 |
| 57 | Asn,Glu,Val,Tyr,Phe,His | 0.839 | 0.856 |
| 58 | Glu,Gln,Cit,Val,Tyr,His | 0.839 | 0.855 |
| 59 | Glu,Ala,Val,Tyr,Phe,Lys | 0.839 | 0.854 |
| 60 | Thr,Glu,Pro,Ala,Val,Tyr | 0.839 | 0.856 |
| 61 | Glu,Gln,Gly,Val,Tyr,His | 0.839 | 0.856 |
| 62 | Glu,Gln,Pro,Val,Tyr,His | 0.839 | 0.855 |
| 63 | Asn,Glu,Ala,Val,Tyr,Orn | 0.839 | 0.854 |
| 64 | Glu,Ala,Tyr,Phe | 0.839 | 0.850 |
| 65 | Glu,Gln,Ala,Val,Ile,Tyr | 0.839 | 0.854 |
| 66 | Thr,Glu,Ala,Val,Tyr,Trp | 0.839 | 0.855 |
| 67 | Thr,Glu,Ala,Val,Tyr,Lys | 0.839 | 0.856 |
| 68 | Glu,Gln,Gly,Ala,Met,Phe | 0.839 | 0.856 |
| 69 | Thr,Glu,Gln,Val,Met,Tyr | 0.839 | 0.855 |
| 70 | Glu,Gln,Ala,Tyr,His,Lys | 0.839 | 0.855 |
| 71 | Glu,Gln,Ala,Met,Tyr,His | 0.839 | 0.856 |
| 72 | Glu,Gln,Ala,Cit,Tyr,His | 0.839 | 0.855 |
| 73 | Ser,Glu,Ala,Val,Tyr | 0.839 | 0.855 |
| 74 | Ser,Glu,Ala,Val,Tyr,His | 0.839 | 0.858 |
| 75 | Ser,Glu,Ala,Tyr,Phe | 0.839 | 0.855 |
| 76 | Thr,Glu,Ala,ABA,Val,Tyr | 0.839 | 0.856 |
| 77 | Thr,Ser,Glu,Ala,Val,Tyr | 0.839 | 0.857 |
| 78 | Thr,Glu,Gln,Ala,Met,Phe | 0.839 | 0.854 |
| 79 | Asn,Glu,Gln,Ala,Leu,Tyr | 0.839 | 0.853 |
| 80 | Glu,Gln,Ala,ABA,Tyr,His | 0.839 | 0.856 |
| 81 | Asn,Glu,Gly,Ala,Val,Tyr | 0.839 | 0.855 |
| 82 | Thr,Glu,Ala,Cit,Val,Tyr | 0.839 | 0.856 |
| 83 | Glu,Gln,Val,Tyr,His,Arg | 0.839 | 0.855 |
| 84 | Glu,Gln,Pro,Ala,Tyr,His | 0.839 | 0.855 |
| 85 | Asn,Glu,Gln,Ala,Tyr,His | 0.839 | 0.855 |
| 86 | Asn,Glu,Ala,Val,Ile,Tyr | 0.839 | 0.853 |
| 87 | Thr,Glu,Ala,Val,Leu,Tyr | 0.839 | 0.855 |
| 88 | Asn,Glu,Ala,Val,Leu,Tyr | 0.839 | 0.854 |
| 89 | Ser,Glu,Gln,Ala,Tyr,His | 0.839 | 0.857 |
| 90 | Thr,Glu,Ala,Val,Met,Tyr | 0.839 | 0.855 |
| 91 | Asn,Glu,Ala,Val,Tyr,Lys | 0.839 | 0.853 |
| 92 | Thr,Glu,Gly,Ala,Val,Tyr | 0.839 | 0.857 |
| 93 | Ser,Glu,Val,Tyr,Phe,His | 0.838 | 0.857 |
| 94 | Asn,Glu,Ala,ABA,Val,Tyr | 0.838 | 0.853 |
| 95 | Thr,Glu,Gln,Ala,Met,Tyr | 0.838 | 0.855 |
| 96 | Glu,Gln,Ala,Tyr,His,Orn | 0.838 | 0.854 |
| 97 | Glu,Gly,Ala,Val,Tyr,His | 0.838 | 0.856 |
| 98 | Glu,Ala,Val,Tyr,Orn | 0.838 | 0.852 |
| 99 | Thr,Glu,Ala,Tyr,Phe | 0.838 | 0.853 |
| 100 | Glu,Ala,Val,Tyr | 0.838 | 0.850 |

FIG.35

| NO | FORMULA | ROC (Validation) | ROC (No Validation) |
|----|---------|------------------|---------------------|
| 1 | (Met)/(Ser+Thr)+(Glu+Tyr+His)/(Gln+Gly) | 0.855 | 0.854 |
| 2 | (Met)/(Gly)+(Glu+Tyr+His)/(Ser+Thr+Gln) | 0.853 | 0.851 |
| 3 | (Glu+Met)/(Ser+Thr)+(Val+Ala)/(Gln+Gly) | 0.851 | 0.853 |
| 4 | (Glu+Tyr)/(Ser+Thr)+(Val+Ala)/(Gln+Gly) | 0.851 | 0.853 |
| 5 | (Glu+Tyr)/(Gly)+(Val+Ala+His)/(Thr+Gln) | 0.851 | 0.851 |
| 6 | (Glu+Met)/(Ser+Asn)+(Val+Ala)/(Gln+Gly) | 0.851 | 0.852 |
| 7 | (Met)/(Gly)+(Glu+Tyr+His)/(Arg+Thr+Gln) | 0.851 | 0.849 |
| 8 | (Met)/(Gly)+(Glu+Phe+His)/(Ser+Thr+Gln) | 0.851 | 0.850 |
| 9 | (Met)/(Gly)+(Glu+Tyr+His)/(Thr+Asn+Gln) | 0.851 | 0.849 |
| 10 | (Glu+Tyr)/(Gly)+(Val+Ala+His)/(Ser+Gln) | 0.851 | 0.850 |
| 11 | (Glu+Tyr)/(Gly)+(Val+Ala)/(Ser+Thr+Gln) | 0.851 | 0.850 |
| 12 | (Met)/(Gly)+(Glu+Tyr+His)/(Arg+Ser+Gln) | 0.851 | 0.848 |
| 13 | (Glu+His)/(Gly)+(Val+Tyr+Ala)/(Thr+Gln) | 0.851 | 0.848 |
| 14 | (Met)/(Arg+Thr)+(Glu+Tyr+His)/(Gln+Gly) | 0.850 | 0.848 |
| 15 | (Glu+Tyr)/(Ser+Asn)+(Val+Ala)/(Gln+Gly) | 0.850 | 0.850 |
| 16 | (Glu)/(Ser+Thr)+(Val+Tyr+Ala)/(Gln+Gly) | 0.850 | 0.851 |
| 17 | (Met)/(Gly)+(Glu+Tyr+His)/(Ser+Asn+Gln) | 0.850 | 0.848 |
| 18 | (Val+Ala)/(Thr+Gln)+(Glu+Tyr+Met)/(Gly) | 0.850 | 0.850 |
| 19 | (Glu+Tyr)/(Gly)+(Val+Ala)/(Thr+Asn+Gln) | 0.850 | 0.850 |
| 20 | (Met)/(Ser+Thr)+(Glu+Tyr+Phe)/(Gln+Gly) | 0.850 | 0.852 |
| 21 | (Val+Ala)/(Thr+Gln)+(Glu+Met+His)/(Gly) | 0.850 | 0.848 |
| 22 | (Glu+Tyr)/(Gly)+(Val+Ala)/(Ser+Asn+Gln) | 0.850 | 0.849 |
| 23 | (Glu+His)/(Gly)+(Val+Tyr+Ala)/(Ser+Gln) | 0.850 | 0.848 |
| 24 | (Glu)/(Ser)+(Val+Tyr+Ala+His)/(Gln+Gly) | 0.850 | 0.850 |
| 25 | (Val+Ala)/(Ser+Gln)+(Glu+Met+His)/(Gly) | 0.850 | 0.847 |
| 26 | (Met)/(Ser+Thr+Asn)+(Glu+Tyr)/(Gln+Gly) | 0.850 | 0.851 |
| 27 | (Glu+Met)/(Gly)+(Val+Ala)/(Ser+Thr+Gln) | 0.850 | 0.850 |
| 28 | (Glu+Tyr)/(Gly)+(Val+Ala)/(Arg+Thr+Gln) | 0.850 | 0.849 |
| 29 | (Glu+Tyr)/(Gly)+(Val+Ala+Met)/(Thr+Gln) | 0.850 | 0.850 |
| 30 | (Val+Ala)/(Thr+Gln)+(Glu+Tyr+His)/(Gly) | 0.850 | 0.847 |
| 31 | (Val+Ala)/(Ser+Gln)+(Glu+Tyr+His)/(Gly) | 0.850 | 0.847 |
| 32 | (Met)/(Gly)+(Glu+Phe+His)/(Ser+Asn+Gln) | 0.850 | 0.848 |
| 33 | (Met)/(Asn+Gly)+(Glu+Tyr+His)/(Ser+Gln) | 0.850 | 0.847 |
| 34 | (Glu)/(Ser+Thr)+(Val+Ala+His)/(Gln+Gly) | 0.850 | 0.849 |
| 35 | (Glu+Met)/(Ser)+(Val+Tyr+Ala)/(Gln+Gly) | 0.850 | 0.851 |
| 36 | (Val+Ala)/(Ser+Gln)+(Glu+Tyr+Met)/(Gly) | 0.849 | 0.849 |
| 37 | (Glu)/(Ser+Asn)+(Val+Tyr+Ala)/(Gln+Gly) | 0.849 | 0.850 |
| 38 | (Met)/(Thr+Asn)+(Glu+Tyr+His)/(Gln+Gly) | 0.849 | 0.849 |
| 39 | (Met)/(Ser+Asn)+(Glu+Tyr+His)/(Gln+Gly) | 0.849 | 0.847 |
| 40 | (Glu+Tyr)/(Gly)+(Val+Ala+Phe)/(Thr+Gln) | 0.849 | 0.849 |
| 41 | (Met)/(Gly)+(Glu+Tyr+His)/(Cit+Thr+Gln) | 0.849 | 0.847 |
| 42 | (Glu+Tyr)/(Gly)+(Val+Ala)/(Arg+Ser+Gln) | 0.849 | 0.848 |
| 43 | (Glu+Tyr)/(Asn+Gly)+(Val+Ala)/(Thr+Gln) | 0.849 | 0.849 |
| 44 | (Glu+Met)/(Ser)+(Val+Ala+His)/(Gln+Gly) | 0.849 | 0.850 |
| 45 | (Met)/(Gly)+(Glu+Phe+His)/(Arg+Ser+Gln) | 0.849 | 0.848 |
| 46 | (Val+Ala)/(Gln)+(Glu+Tyr+His)/(Asn+Gly) | 0.849 | 0.847 |
| 47 | (Glu+His)/(Gly)+(Val+Ala+Met)/(Thr+Gln) | 0.849 | 0.847 |
| 48 | (Glu+His)/(Gly)+(Val+Ala)/(Ser+Asn+Gln) | 0.849 | 0.847 |
| 49 | (Glu+Tyr)/(Gly)+(Val+Ala)/(Cit+Thr+Gln) | 0.849 | 0.849 |
| 50 | (Met)/(Cit+Gly)+(Glu+Tyr+His)/(Thr+Gln) | 0.849 | 0.847 |

FIG.36

| NO | FORMULA | ROC (Validation) | ROC (No Validation) |
|---|---|---|---|
| 51 | (Met)/(Gly)+(Glu+Tyr+His)/(Thr+Gln) | 0.849 | 0.847 |
| 52 | (Glu+Tyr)/(Gly)+(Leu+Ala+His)/(Thr+Gln) | 0.849 | 0.849 |
| 53 | (Met)/(Cit+Gly)+(Glu+Tyr+His)/(Ser+Gln) | 0.849 | 0.847 |
| 54 | (Glu)/(Ser+Asn)+(Val+Ala+His)/(Gln+Gly) | 0.849 | 0.849 |
| 55 | (Met)/(Cit+Ser+Thr)+(Glu+Tyr)/(Gln+Gly) | 0.849 | 0.850 |
| 56 | (Glu+His)/(Gly)+(Val+Ala+Met)/(Ser+Gln) | 0.849 | 0.847 |
| 57 | (Glu+Met)/(Gly)+(Val+Tyr+Ala)/(Thr+Gln) | 0.849 | 0.849 |
| 58 | (Met)/(Arg+Ser)+(Glu+Tyr+His)/(Gln+Gly) | 0.849 | 0.846 |
| 59 | (Met)/(Asn+Gly)+(Glu+Tyr+His)/(Thr+Gln) | 0.849 | 0.847 |
| 60 | (Glu+His)/(Gly)+(Val+Ala+Phe)/(Ser+Gln) | 0.849 | 0.847 |
| 61 | (Glu+Tyr)/(Gly)+(Val+Ala+Met)/(Ser+Gln) | 0.849 | 0.849 |
| 62 | (Glu)/(Ser)+(Val+Tyr+Ala+Phe)/(Gln+Gly) | 0.849 | 0.850 |
| 63 | (Glu+His)/(Gln)+(Tyr+Met)/(Ser+Thr+Gly) | 0.849 | 0.847 |
| 64 | (Glu+His)/(Gly)+(Val+Ala+Phe)/(Thr+Gln) | 0.849 | 0.847 |
| 65 | (Glu+Tyr)/(Gly)+(Val+Ala)/(Thr+Gln) | 0.849 | 0.849 |
| 66 | (Glu+His)/(Gly)+(Val+Ala)/(Ser+Thr+Gln) | 0.849 | 0.847 |
| 67 | (Met)/(Gly)+(Glu+Tyr+Phe+His)/(Thr+Gln) | 0.849 | 0.847 |
| 68 | (Glu)/(Ser)+(Val+Tyr+Ala+Met)/(Gln+Gly) | 0.849 | 0.850 |
| 69 | (Val+Ala)/(Asn+Gln)+(Glu+Tyr+His)/(Gly) | 0.849 | 0.846 |
| 70 | (Glu)/(Ser)+(Val+Ala+Phe+His)/(Gln+Gly) | 0.849 | 0.849 |
| 71 | (Glu+Tyr)/(Gly)+(Leu+Ala+His)/(Ser+Gln) | 0.849 | 0.848 |
| 72 | (Met)/(Gly)+(Glu+Tyr+His)/(Cit+Ser+Gln) | 0.849 | 0.846 |
| 73 | (Glu)/(Ser+Thr)+(Val+Ala+Phe)/(Gln+Gly) | 0.849 | 0.849 |
| 74 | (Glu+Tyr)/(Gly)+(Val+Ala+His)/(Arg+Gln) | 0.849 | 0.847 |
| 75 | (Met)/(Gly)+(Glu+Phe+His)/(Thr+Asn+Gln) | 0.849 | 0.848 |
| 76 | (Met)/(Ser+Thr)+(Glu+Phe+His)/(Gln+Gly) | 0.849 | 0.849 |
| 77 | (Met)/(Gly)+(Glu+Tyr+Phe+His)/(Ser+Gln) | 0.849 | 0.847 |
| 78 | (Val+Ala)/(Arg+Gln)+(Glu+Tyr+His)/(Gly) | 0.849 | 0.845 |
| 79 | (Glu+Tyr)/(Gly)+(Val+Ala)/(Arg+Asn+Gln) | 0.849 | 0.848 |
| 80 | (Glu+Phe)/(Ser+Asn)+(Val+Ala)/(Gln+Gly) | 0.849 | 0.849 |
| 81 | (Glu)/(Thr+Asn)+(Val+Tyr+Ala)/(Gln+Gly) | 0.848 | 0.849 |
| 82 | (Glu+Tyr+His)/(Gly)+(Val+Ala+Met)/(Gln) | 0.848 | 0.846 |
| 83 | (Glu+His)/(Gly)+(Val+Ala)/(Arg+Ser+Gln) | 0.848 | 0.845 |
| 84 | (Glu+Met)/(Ser)+(Val+Ala+Phe)/(Gln+Gly) | 0.848 | 0.850 |
| 85 | (Glu+Tyr+Met+His)/(Ser+Thr+Gln+Gly) | 0.848 | 0.846 |
| 86 | (Glu+Tyr)/(Gly)+(Val+Ala+ABA)/(Thr+Gln) | 0.848 | 0.848 |
| 87 | (Glu+Phe)/(Ser+Thr)+(Val+Ala)/(Gln+Gly) | 0.848 | 0.850 |
| 88 | (Val+Ala)/(Arg+Gln)+(Glu+Met+His)/(Gly) | 0.848 | 0.845 |
| 89 | (Met)/(Gly)+(Glu+Tyr+His)/(Ser+Gln) | 0.848 | 0.846 |
| 90 | (Glu+Tyr)/(Gly)+(Val+Ala+Phe)/(Ser+Gln) | 0.848 | 0.848 |
| 91 | (Glu+Tyr)/(Gly)+(Val+Ala)/(Ser+Gln) | 0.848 | 0.848 |
| 92 | (Glu)/(Ser)+(Val+Ala+Met+His)/(Gln+Gly) | 0.848 | 0.848 |
| 93 | (Glu+Tyr)/(Gly)+(Ala+Phe+His)/(Thr+Gln) | 0.848 | 0.848 |
| 94 | (Glu+His)/(Gly)+(Val+Tyr+Ala)/(Arg+Gln) | 0.848 | 0.845 |
| 95 | (Glu+His)/(Gly)+(Val+Ala)/(Thr+Asn+Gln) | 0.848 | 0.846 |
| 96 | (Val+Ala)/(Asn+Gln)+(Glu+Met+His)/(Gly) | 0.848 | 0.846 |
| 97 | (Glu+His)/(Ser+Thr)+(Val+Ala)/(Gln+Gly) | 0.848 | 0.847 |
| 98 | (Glu+His)/(Gly)+(Val+Tyr+Ala)/(Asn+Gln) | 0.848 | 0.846 |
| 99 | (Glu+His)/(Gly)+(Val+Ala)/(Ser+Gln) | 0.848 | 0.845 |
| 100 | (Glu)/(Ser+Asn)+(Val+Ala+Phe)/(Gln+Gly) | 0.848 | 0.849 |

FIG.37

| NO | FORMULA(Variable only) | ROC (Validation) | ROC (No Validation) |
|---|---|---|---|
| 1 | Asn,Gln,Ala,Cit,Ile,Leu | 0.712 | 0.764 |
| 2 | Asn,Gln,Ala,Cit | 0.708 | 0.745 |
| 3 | Asn,Gln,Ala,Cit,Met,Trp | 0.708 | 0.756 |
| 4 | Asn,Gln,Ala,Cit,Leu | 0.707 | 0.748 |
| 5 | Asn,Gln,Ala,Cit,Trp | 0.706 | 0.751 |
| 6 | Gln,Ala,Cit,Trp | 0.705 | 0.741 |
| 7 | Asn,Gln,Ala,Cit,Orn | 0.705 | 0.744 |
| 8 | Asn,Gln,Ala,Cit,Met | 0.705 | 0.747 |
| 9 | Gln,Ala,Cit,Leu,Trp | 0.704 | 0.746 |
| 10 | Asn,Gln,Ala,Cit,Trp,Orn | 0.704 | 0.751 |
| 11 | Asn,Gln,Ala,Cit,Phe | 0.704 | 0.745 |
| 12 | Asn,Gln,Ala,Cit,Ile | 0.703 | 0.746 |
| 13 | Asn,Gln,Gly,Ala,Cit,Met | 0.703 | 0.753 |
| 14 | Asn,Gln,Gly,Ala,Cit | 0.703 | 0.743 |
| 15 | Asn,Gln,Ala,Cit,Val | 0.702 | 0.744 |
| 16 | Asn,Gln,Ala,Cit,Arg | 0.702 | 0.744 |
| 17 | Asn,Gln,Ala,Cit,Leu,Trp | 0.702 | 0.750 |
| 18 | Asn,Gln,Pro,Ala,Cit,Leu | 0.702 | 0.749 |
| 19 | Asn,Gln,Ala,Cit,Lys | 0.702 | 0.744 |
| 20 | Gln,Ala,Cit,Val,Trp | 0.701 | 0.742 |
| 21 | Asn,Gln,Pro,Ala,Cit | 0.701 | 0.744 |
| 22 | Asn,Gln,Ala,Cit,Phe,Orn | 0.701 | 0.748 |
| 23 | Asn,Gln,Ala,Cit,Leu,Orn | 0.701 | 0.751 |
| 24 | Gln,Ala,Cit,Leu | 0.701 | 0.739 |
| 25 | Thr,Asn,Gln,Ala,Cit | 0.701 | 0.745 |
| 26 | Asn,Gln,Ala,Cit,Leu,Phe | 0.701 | 0.750 |
| 27 | Gln,Ala,Cit,Met,Trp | 0.700 | 0.742 |
| 28 | Ser,Asn,Gln,Ala,Cit,Leu | 0.700 | 0.753 |
| 29 | Gln,Pro,Ala,Cit,Leu,Trp | 0.700 | 0.748 |
| 30 | Gln,Ala,Cit,Leu,Trp,Lys | 0.700 | 0.748 |
| 31 | Asn,Gln,Gly,Ala,Cit,Trp | 0.700 | 0.748 |
| 32 | Asn,Gln,Pro,Ala,Cit,Trp | 0.700 | 0.750 |
| 33 | Glu,Gln,Ala,Cit,Trp | 0.700 | 0.742 |
| 34 | Asn,Gln,Ala,Cit,ABA | 0.700 | 0.744 |
| 35 | Gln,Ala,Cit,Phe,Trp | 0.700 | 0.743 |
| 36 | Asn,Gln,Ala,Cit,Met,Leu | 0.700 | 0.749 |
| 37 | Asn,Gln,Ala,Cit,Ile,Phe | 0.700 | 0.747 |
| 38 | Asn,Gln,Ala,Cit,Phe,Trp | 0.700 | 0.752 |
| 39 | Thr,Asn,Gln,Ala,Cit,Trp | 0.700 | 0.752 |
| 40 | Gln,Ala,Cit,Orn | 0.700 | 0.732 |
| 41 | Gln,Ala,Cit,Ile,Leu,Trp | 0.700 | 0.749 |
| 42 | Gln,Pro,Ala,Cit,Trp | 0.699 | 0.740 |
| 43 | Asn,Glu,Gln,Ala,Cit,Orn | 0.699 | 0.744 |
| 44 | Asn,Glu,Gln,Ala,Cit,Leu | 0.699 | 0.749 |
| 45 | Asn,Gln,Gly,Ala,Cit,Leu | 0.699 | 0.751 |
| 46 | Asn,Gln,Ala,Cit,Leu,Tyr | 0.699 | 0.745 |
| 47 | Asn,Gln,Pro,Ala,Cit,Met | 0.699 | 0.748 |
| 48 | Gln,Ala,Cit,Phe | 0.699 | 0.734 |
| 49 | Thr,Asn,Gln,Ala,Cit,Orn | 0.699 | 0.744 |
| 50 | Asn,Gln,Ala,Cit,Ile,Trp | 0.699 | 0.751 |

FIG.38

| NO | FORMULA(Variable only) | ROC (Validation) | ROC (No Validation) |
|---|---|---|---|
| 51 | Asn,Glu,Gln,Ala,Cit | 0.699 | 0.744 |
| 52 | Asn,Gln,Pro,Ala,Cit,Orn | 0.699 | 0.744 |
| 53 | Asn,Gln,Ala,Cit,Orn,Lys | 0.699 | 0.744 |
| 54 | Asn,Gln,Ala,Cit,ABA,Leu | 0.699 | 0.749 |
| 55 | Asn,Gln,Pro,Ala,Cit,Phe | 0.699 | 0.746 |
| 56 | Asn,Gln,Ala,Cit,Met,Orn | 0.698 | 0.750 |
| 57 | Asn,Gln,Ala,Cit,Val,Trp | 0.698 | 0.749 |
| 58 | Asn,Gln,Ala,Cit,Leu,Lys | 0.698 | 0.750 |
| 59 | Asn,Gln,Ala,Cit,Ile,Orn | 0.698 | 0.750 |
| 60 | Asn,Gln,Ala,Cit,ABA,Trp | 0.698 | 0.748 |
| 61 | Ser,Asn,Gln,Ala,Cit,Trp | 0.698 | 0.753 |
| 62 | Glu,Gln,Ala,Cit,Val,Trp | 0.698 | 0.746 |
| 63 | Asn,Glu,Gln,Ala,Cit,Trp | 0.698 | 0.752 |
| 64 | Asn,Gln,Gly,Ala,Cit,Phe | 0.698 | 0.747 |
| 65 | Asn,Gln,Ala,Cit,Leu,Arg | 0.698 | 0.747 |
| 66 | Glu,Gln,Ala,Cit | 0.698 | 0.737 |
| 67 | Gln,Ala,Cit,Trp,Orn | 0.698 | 0.742 |
| 68 | Ser,Asn,Gln,Ala,Cit,Orn | 0.698 | 0.748 |
| 69 | Asn,Gln,Ala,Cit,Val,Leu | 0.698 | 0.748 |
| 70 | Asn,Gln,Ala,Cit,Val,Ile | 0.698 | 0.750 |
| 71 | Gln,Gly,Ala,Cit,Trp | 0.698 | 0.740 |
| 72 | Asn,Glu,Gln,Ala,Cit,Phe | 0.698 | 0.748 |
| 73 | Gln,Ala,Cit,ABA,Trp | 0.697 | 0.740 |
| 74 | Glu,Gln,Ala,Cit,Leu,Trp | 0.697 | 0.747 |
| 75 | Gln,Ala,Cit,Val,Met,Trp | 0.697 | 0.748 |
| 76 | Asn,Gln,Ala,Cit,ABA,Met | 0.697 | 0.747 |
| 77 | Gln,Ala,Cit,Leu,Orn | 0.697 | 0.737 |
| 78 | Asn,Gln,Ala,Cit,ABA,Orn | 0.697 | 0.747 |
| 79 | Gln,Ala,Cit,Ile,Leu | 0.697 | 0.738 |
| 80 | Gln,Ala,Cit,Leu,Phe,Trp | 0.697 | 0.746 |
| 81 | Gln,Pro,Ala,Cit | 0.697 | 0.733 |
| 82 | Gln,Ala,Cit,Trp,Arg | 0.697 | 0.739 |
| 83 | Asn,Gln,Ala,Cit,Tyr,Trp | 0.697 | 0.748 |
| 84 | Asn,Gln,Ala,Cit,Met,Phe | 0.697 | 0.750 |
| 85 | Asn,Gln,Ala,Cit,Trp,Arg | 0.697 | 0.752 |
| 86 | Gln,Ala,Cit,Trp,Lys | 0.697 | 0.740 |
| 87 | Asn,Gln,Pro,Ala,Cit,Ile | 0.697 | 0.748 |
| 88 | Asn,Gln,Ala,Cit,Tyr | 0.697 | 0.740 |
| 89 | Asn,Gln,Ala,Cit,His | 0.697 | 0.745 |
| 90 | Ser,Asn,Gln,Ala,Cit | 0.697 | 0.746 |
| 91 | Asn,Gln,Gly,Ala,Cit,Orn | 0.697 | 0.746 |
| 92 | Gln,Ala,Cit,Val,Phe,Trp | 0.697 | 0.745 |
| 93 | Gln,Ala,Cit,Ile,Trp | 0.697 | 0.741 |
| 94 | Asn,Gln,Ala,Cit,Met,Lys | 0.697 | 0.747 |
| 95 | Asn,Glu,Gln,Ala,Cit,Val | 0.696 | 0.744 |
| 96 | Gln,Ala,Cit,Met,Leu,Trp | 0.696 | 0.747 |
| 97 | Gln,Ala,Cit,Val | 0.696 | 0.735 |
| 98 | Asn,Gln,Gly,Ala,Cit,Ile | 0.696 | 0.747 |
| 99 | Gln,Ala,Cit,Tyr,Trp | 0.696 | 0.739 |
| 100 | Asn,Gln,Ala,Cit,ABA,Phe | 0.696 | 0.746 |

FIG.39

| NO | FORMULA | ROC (Validation) | ROC (No Validation) |
|---|---|---|---|
| 1 | (Cit+Met)/(Trp+Asn)+(Leu+Pro+ABA)/(Gln) | 0.765 | 0.752 |
| 2 | (Cit+Met)/(Trp+Asn)+(Leu+Pro+Phe)/(Gln) | 0.762 | 0.751 |
| 3 | (Cit)/(Asn)+(Ala+Orn+Leu+Pro+Phe)/(Gln) | 0.761 | 0.749 |
| 4 | (Cit)/(Trp+Asn)+(Leu+Pro+Met+ABA)/(Gln) | 0.760 | 0.748 |
| 5 | (Cit+Met)/(Trp+Asn)+(Leu+Pro+Tyr)/(Gln) | 0.760 | 0.746 |
| 6 | (Cit+Met)/(Trp+Asn)+(Glu+Leu+Pro)/(Gln) | 0.760 | 0.750 |
| 7 | (Cit+Met)/(Trp)+(Ala+Val+Leu+Tyr)/(Gln) | 0.760 | 0.749 |
| 8 | (Cit)/(Asn)+(Glu+Ala+Leu+Pro+Phe)/(Gln) | 0.760 | 0.749 |
| 9 | (Cit)/(Asn)+(Ala+Orn+Leu+Pro+ABA)/(Gln) | 0.760 | 0.747 |
| 10 | (Cit)/(Asn)+(Glu+Ala+Orn+Leu+Pro)/(Gln) | 0.760 | 0.747 |
| 11 | (Cit)/(Asn)+(Ala+Leu+Pro+Phe+ABA)/(Gln) | 0.759 | 0.748 |
| 12 | (Cit+Met)/(Trp+Asn)+(Orn+Leu+Pro)/(Gln) | 0.759 | 0.747 |
| 13 | (Cit)/(Asn)+(Ala+Orn+Leu+Pro+Tyr)/(Gln) | 0.759 | 0.746 |
| 14 | (Cit)/(Asn)+(Ala+Leu+Pro+Tyr+Phe)/(Gln) | 0.759 | 0.747 |
| 15 | (Cit)/(Asn)+(Ala+Leu+Pro+Tyr+ABA)/(Gln) | 0.759 | 0.746 |
| 16 | (Cit)/(Asn)+(Glu+Ala+Leu+Pro+Met)/(Gln) | 0.758 | 0.746 |
| 17 | (Cit+Met)/(Trp)+(Glu+Ala+Val+Phe)/(Gln) | 0.758 | 0.749 |
| 18 | (Cit)/(Asn)+(Ala+Leu+Pro+Tyr)/(Trp+Gln) | 0.758 | 0.743 |
| 19 | (Cit+ABA)/(Trp+Asn)+(Leu+Pro+Met)/(Gln) | 0.758 | 0.743 |
| 20 | (Cit)/(Trp+Asn)+(Leu+Pro+Phe+ABA)/(Gln) | 0.758 | 0.749 |
| 21 | (Cit+Met)/(Trp)+(Glu+Ala+Val+Leu)/(Gln) | 0.758 | 0.748 |
| 22 | (Cit+Met)/(Trp)+(Ala+Orn+Val+ABA)/(Gln) | 0.758 | 0.747 |
| 23 | (Cit+Met)/(Trp)+(Glu+Ala+Val+Pro)/(Gln) | 0.758 | 0.750 |
| 24 | (Cit+Met)/(Trp)+(Glu+Ala+Orn+Val)/(Gln) | 0.757 | 0.748 |
| 25 | (Cit)/(Asn)+(Ala+Orn+Leu+Pro+Met)/(Gln) | 0.757 | 0.745 |
| 26 | (Cit+Met)/(Trp)+(Ala+Orn+Val+Leu)/(Gln) | 0.757 | 0.748 |
| 27 | (Leu+Pro)/(Gln)+(Cit+Met)/(Trp+Asn) | 0.757 | 0.744 |
| 28 | (Cit)/(Asn)+(Glu+Ala+Leu+Pro+Tyr)/(Gln) | 0.757 | 0.745 |
| 29 | (Cit)/(Asn)+(Ala+Leu+Pro+Met+Phe)/(Gln) | 0.757 | 0.746 |
| 30 | (Cit)/(Asn)+(Ala+Leu+Pro+ABA)/(Trp+Gln) | 0.757 | 0.742 |
| 31 | (Cit)/(Asn)+(Glu+Ala+Leu+Pro+ABA)/(Gln) | 0.757 | 0.744 |
| 32 | (Cit+Met)/(Trp)+(Glu+Ala+Val+Tyr)/(Gln) | 0.757 | 0.747 |
| 33 | (Cit)/(Asn)+(Ala+Orn+Leu+Met+ABA)/(Gln) | 0.757 | 0.745 |
| 34 | (Cit)/(Asn)+(Glu+Ala+Orn+Pro+Tyr)/(Gln) | 0.757 | 0.744 |
| 35 | (Cit)/(Asn)+(Ala+Leu+Pro+Phe)/(Gln) | 0.757 | 0.744 |
| 36 | (Cit+Met)/(Trp)+(Glu+Ala+Val)/(Gln) | 0.757 | 0.746 |
| 37 | (Cit)/(Asn)+(Ala+Leu+Pro+Phe)/(Trp+Gln) | 0.756 | 0.743 |
| 38 | (Val+Pro)/(Gln)+(Cit+Met+ABA)/(Trp+Asn) | 0.756 | 0.747 |
| 39 | (Cit+Met)/(Trp)+(Glu+Ala+Leu+Pro)/(Gln) | 0.756 | 0.745 |
| 40 | (Cit)/(Asn)+(Glu+Ala+Orn+Pro+ABA)/(Gln) | 0.756 | 0.743 |
| 41 | (Cit+Met)/(Trp)+(Ala+Val+Leu+Pro)/(Gln) | 0.756 | 0.748 |
| 42 | (Cit)/(Asn)+(Ala+Leu+Pro+Met+ABA)/(Gln) | 0.756 | 0.743 |
| 43 | (Cit+Met)/(Trp)+(Glu+Ala+Val+ABA)/(Gln) | 0.756 | 0.747 |
| 44 | (Cit)/(Asn)+(Glu+Ala+Leu+Tyr)/(Trp+Gln) | 0.756 | 0.741 |
| 45 | (Cit)/(Asn)+(Glu+Ala+Pro+Phe+ABA)/(Gln) | 0.756 | 0.743 |
| 46 | (Cit)/(Asn)+(Ala+Leu+Pro+Met)/(Trp+Gln) | 0.756 | 0.741 |
| 47 | (Cit)/(Asn)+(Glu+Ala+Leu+Pro)/(Trp+Gln) | 0.756 | 0.742 |
| 48 | (Cit)/(Asn)+(Glu+Ala+Leu+Phe)/(Trp+Gln) | 0.756 | 0.742 |
| 49 | (Cit+Met)/(Trp)+(Ala+Val+Leu+Phe)/(Gln) | 0.756 | 0.748 |
| 50 | (Cit)/(Asn)+(Ala+Leu+Pro+Tyr+Met)/(Gln) | 0.756 | 0.743 |

FIG.40

| NO | FORMULA | ROC (Validation) | ROC (No Validation) |
|---|---|---|---|
| 51 | (Cit)/(Asn)+(Ala+Orn+Leu+Pro)/(Trp+Gln) | 0.756 | 0.742 |
| 52 | (Cit+Met)/(Trp)+(Ala+Val+Leu)/(Asn+Gln) | 0.756 | 0.744 |
| 53 | (Cit+Met)/(Trp)+(Ala+Orn+Val+Tyr)/(Gln) | 0.756 | 0.745 |
| 54 | (Cit)/(Asn)+(Glu+Ala+Leu+ABA)/(Trp+Gln) | 0.756 | 0.741 |
| 55 | (Cit+Met)/(Trp)+(Ala+Orn+Val+Phe)/(Gln) | 0.756 | 0.746 |
| 56 | (Cit+Met)/(Trp)+(Ala+Val+Leu+ABA)/(Gln) | 0.756 | 0.745 |
| 57 | (Cit)/(Trp+Asn)+(Leu+Pro+Met+Phe)/(Gln) | 0.756 | 0.746 |
| 58 | (Cit)/(Asn)+(Ala+Pro+Tyr+Phe+ABA)/(Gln) | 0.756 | 0.743 |
| 59 | (Cit)/(Asn)+(Ala+Orn+Leu+ABA)/(Gln) | 0.756 | 0.743 |
| 60 | (Cit)/(Asn)+(Glu+Ala+Orn+Leu+Phe)/(Gln) | 0.756 | 0.745 |
| 61 | (Cit)/(Asn)+(Ala+Orn+Leu+Pro)/(Gln) | 0.755 | 0.743 |
| 62 | (Cit)/(Trp+Asn)+(Leu+Pro+ABA)/(Gln) | 0.755 | 0.742 |
| 63 | (Cit)/(Asn)+(Ala+Orn+Pro+Phe+ABA)/(Gln) | 0.755 | 0.744 |
| 64 | (Cit+Met)/(Trp)+(Ala+Val+Phe+ABA)/(Gln) | 0.755 | 0.745 |
| 65 | (Cit+Met)/(Trp)+(Ala+Val+Tyr+ABA)/(Gln) | 0.755 | 0.745 |
| 66 | (Leu+Pro)/(Gln)+(Cit+Met+ABA)/(Trp+Asn) | 0.755 | 0.741 |
| 67 | (Cit)/(Asn)+(Glu+Ala+Pro+Tyr)/(Trp+Gln) | 0.755 | 0.740 |
| 68 | (Cit+Met)/(Trp)+(Ala+Val+Tyr+Phe)/(Gln) | 0.755 | 0.745 |
| 69 | (Cit+Met)/(Trp)+(Glu+Ala+Val)/(Asn+Gln) | 0.755 | 0.744 |
| 70 | (Cit)/(Asn)+(Glu+Ala+Leu+Pro)/(Gln) | 0.755 | 0.743 |
| 71 | (Cit+Met)/(Trp)+(Ala+Val+Pro+ABA)/(Gln) | 0.755 | 0.746 |
| 72 | (Cit)/(Asn)+(Glu+Ala+Orn+Pro+Phe)/(Gln) | 0.755 | 0.743 |
| 73 | (Cit)/(Asn)+(Ala+Orn+Leu+Met+Phe)/(Gln) | 0.755 | 0.745 |
| 74 | (Cit+Met)/(Trp+Asn)+(Val+Pro+ABA)/(Gln) | 0.755 | 0.746 |
| 75 | (Cit+Met)/(Trp)+(Ala+Leu+Pro+Tyr)/(Gln) | 0.755 | 0.742 |
| 76 | (Cit)/(Trp)+(Glu+Ala+Leu+Tyr)/(Asn+Gln) | 0.755 | 0.742 |
| 77 | (Cit)/(Asn)+(Glu+Ala+Pro+Tyr+Phe)/(Gln) | 0.755 | 0.742 |
| 78 | (Cit)/(Asn)+(Glu+Ala+Leu+Met)/(Arg+Gln) | 0.755 | 0.740 |
| 79 | (Cit)/(Trp)+(Glu+Ala+Pro+Tyr)/(Asn+Gln) | 0.755 | 0.742 |
| 80 | (Cit)/(Asn)+(Glu+Ala+Orn+Leu+Met)/(Gln) | 0.755 | 0.743 |
| 81 | (Cit)/(Asn)+(Glu+Ala+Pro+Met+ABA)/(Gln) | 0.755 | 0.741 |
| 82 | (Cit+ABA)/(Trp+Asn)+(Orn+Leu+Pro)/(Gln) | 0.755 | 0.740 |
| 83 | (Cit)/(Asn)+(Ala+Leu+Pro+Tyr)/(Gln) | 0.755 | 0.741 |
| 84 | (Cit)/(Asn)+(Ala+Leu+Pro+Met)/(Gln) | 0.755 | 0.741 |
| 85 | (Cit)/(Asn)+(Glu+Ala+Pro+Tyr+ABA)/(Gln) | 0.754 | 0.742 |
| 86 | (Cit+Met)/(Trp)+(Ala+Val+Pro+Tyr)/(Gln) | 0.754 | 0.745 |
| 87 | (Cit)/(Asn)+(Glu+Ala+Pro+Met+Phe)/(Gln) | 0.754 | 0.742 |
| 88 | (Cit)/(Asn)+(Ala+Orn+Pro+Tyr+ABA)/(Gln) | 0.754 | 0.741 |
| 89 | (Cit)/(Asn)+(Glu+Ala+Orn+Leu+Tyr)/(Gln) | 0.754 | 0.743 |
| 90 | (Cit)/(Asn)+(Glu+Ala+Leu+Phe+ABA)/(Gln) | 0.754 | 0.744 |
| 91 | (Cit)/(Trp)+(Glu+Ala+Leu+Phe)/(Asn+Gln) | 0.754 | 0.742 |
| 92 | (Cit+Met)/(Trp)+(Ala+Val+Tyr)/(Asn+Gln) | 0.754 | 0.742 |
| 93 | (Cit)/(Asn)+(Ala+Pro+Tyr+Phe)/(Trp+Gln) | 0.754 | 0.738 |
| 94 | (Cit)/(Asn)+(Ala+Orn+Leu+Tyr+ABA)/(Gln) | 0.754 | 0.742 |
| 95 | (Cit)/(Asn)+(Glu+Ala+Orn+Leu+ABA)/(Gln) | 0.754 | 0.743 |
| 96 | (Cit)/(Asn)+(Ala+Pro+Met+Phe+ABA)/(Gln) | 0.754 | 0.741 |
| 97 | (Cit)/(Asn)+(Glu+Ala+Leu+Met+Phe)/(Gln) | 0.754 | 0.743 |
| 98 | (Cit)/(Asn)+(Ala+Leu+Pro+ABA)/(Gln) | 0.754 | 0.740 |
| 99 | (Cit)/(Trp+Asn)+(Leu+Pro+Phe)/(Gln) | 0.754 | 0.743 |
| 100 | (Cit+Met)/(Trp)+(Glu+Val+Leu+Pro)/(Gln) | 0.754 | 0.745 |

| N | Prediction | | | Sum | Prev | Sen | PPV | PPV/Prev |
|---|---|---|---|---|---|---|---|---|
| | Normal | Steatosis | NASH | | | | | |
| Normal | 1098 | 187 | 130 | 1415 | 0.894 | 0.776 | 0.961 | 1.075 |
| Steatosis | 32 | 46 | 25 | 103 | 0.065 | 0.447 | 0.188 | 2.884 |
| NASH | 12 | 12 | 40 | 64 | 0.040 | 0.625 | 0.205 | 5.071 |
| Sum | 1142 | 245 | 195 | 1582 | | | | |

METHOD OF EVALUATING FATTY LIVER RELATED DISEASE, FATTY LIVER RELATED DISEASE-EVALUATING APPARATUS, FATTY LIVER RELATED DISEASE-EVALUATING METHOD, FATTY LIVER RELATED DISEASE-EVALUATING PROGRAM PRODUCT, FATTY LIVER RELATED DISEASE-EVALUATING SYSTEM, INFORMATION COMMUNICATION TERMINAL APPARATUS, AND METHOD OF SEARCHING FOR PROPHYLACTIC/AMELIORATING SUBSTANCE FOR FATTY LIVER RELATED DISEASE

CROSS-REFERENCE TO RELATED APPLICATION

This application is based upon and claims the benefit of priority from PCT Application PCT/JP2012/066739, filed Jun. 29, 2012, which claims priority from Japanese Patent Application No. 2011-146696, filed Jun. 30, 2011, the entire contents of which are incorporated herein by reference.

BACKGROUND OF THE INVENTION

1. Field of the Invention

The present invention relates to a method of evaluating fatty liver related disease, a fatty liver related disease-evaluating apparatus, a fatty liver related disease-evaluating method, a fatty liver related disease-evaluating program product, a fatty liver related disease-evaluating system, and information communication terminal apparatus, which utilize a concentration of an amino acid in blood (including, for example, plasma, serum, and the like) and a method of searching for prophylactic/ameliorating substance for fatty liver related disease which searches a substance for preventing a fatty liver related disease or ameliorating a state of a fatty liver related disease.

2. Description of the Related Art

Non-alcoholic steatohepatitis (NASH) and non-alcoholic fatty liver disease (NAFLD) are liver symptoms that are generally based on fatty liver (accumulation of fat droplets in hepatic cells) diagnosed by ultrasonic diagnosis and present a hepatic histological image similar to that of an alcoholic liver disorder in terms of a hepatic histological finding although the patient has no history of excessive alcohol drinking and is not infected with hepatitis virus ("Guide for Diagnosis of NASH/NAFLD, 2010, edited by Japan Society of Hepatology"). The liver disorder characterized principally by large droplet liver fat deposition is called NAFLD, and NAFLD is further classified into simple steatosis that has good prognosis, and NASH that is progressive and ultimately leads to hepatic cirrhosis ("Guide for Diagnosis of NASH/NAFLD, 2010, edited by Japan Society of Hepatology").

Historically, Ludwig reported in 1980, as NASH, a case where although having no history of excessive drinking, a patient had an alcoholic liver disorder leading to hepatic cirrhosis, and in 1986, Schaffner reported a group of diseases of NAFLD. Regarding the hepatic histological image of NAFLD, mention is made of Matteoni's four-type classification (type 1: simple steatosis; type 2: fatty hepatitis; type 3: fatty hepatic necrosis with balloon-like degeneration; and type 4: hepatic cell necrosis with Mallory body or fibrogenesis), and type 3 and type 4, with which the frequency of development to hepatic cirrhosis or liver-related death is high, belong to NASH. Regarding NASH, mention is made of Brunt's four-type classification by the degree of fibrogenesis (Stage 1: lobulus center; Stage 2: from lobulus center to portal vein area; Stage 3: bridging; and Stage 4: hepatic cirrhosis).

NASH and NAFLD strongly correlate with obesity or metabolic syndrome. In the obesity group, type 1 of NAFLD constitutes 60% to 70%, type 3 or type 4 of NAFLD (i.e. NASH) constitutes 20% to 25%, and hepatic cirrhosis (i.e. Stage 4 of NASH) constitutes 2% to 3%. Further, the frequencies of combination with lipid metabolism abnormality, high blood pressure, and hyperglycemia in NASH are 60%, 60%, and 30%, respectively, and the frequency of combination with metabolic syndrome is as high as about 50%.

Fatty liver, on which NASH and NAFLD are based, is found in 20% to 30% of all medical examination examinees, and has tended to increase in recent years as in the case of metabolic syndrome. In association with development of the hepatic symptom from fatty liver to NAFLD and to NASH, NAFLD is found in 8% of medical examination examinees, and the frequency of NASH is estimated to be 0.5% to 1% of adults. Prognosis of NASH is poor, and in NASH, development to fibrogenesis has been found in 25% of the patients and development to hepatic cirrhosis has been found in 15% of the patients over five years, and the survival rate of HASH is 67% for five years, and 59% for ten years.

Regarding the mechanism of onset of NAFLD and NASH, the "two-hit theory" is accepted in which first, fat accumulation occurs in hepatic cells, and then a factor of hepatic cell disorder such as oxidation stress is added, leading to onset of the disease. Regarding the treatment of NAFLD and NASH, exercise and dietary therapies for amelioration of obesity, and drug therapies using insulin resistance improving agents, biguanide agents, ursodeoxycholic acid, antihyperlipemic agents, antioxidants, and the like are examined, but therapies using control are scarcely examined.

For definite diagnosis of NAFLD and NASH, hepatic histological images from liver biopsy are required. However, liver biopsy is highly invasive, and gives pain to patients, and further has a risk of bleeding or the like, etc. so that patients are placed under a great burden. Therefore, it is almost practically impossible to subject 20% to 30% of all medical examination examinees, i.e. those that are found to have fatty liver, to liver biopsy.

In view of these situations, it is desired from the viewpoint of a physical burden of patients and medical economy that cases with a high possibility of NASH or NAFLD be first discriminated using a less-invasive simple and convenient method in lieu of liver biopsy, and the discriminated cases be determined as objects to be subjected to NASH diagnosis by liver biopsy and objects to be treated.

As low-invasive methods for discriminating NAFLD and NASH, transaminase (ALT>AST), a rise in γ GTP, an increase in AST/ALT ratio, a fibrogenesis marker such as hyaluronic acid, a decrease in blood platelet count, a HOMA index representing insulin resistance, an oxidation stress marker, an adipocyte-pokine such as adiponectin, a high-sensitivity CRP and so on have been heretofore reported ("Guide for Diagnosis of NASH/NAFLD, 2010, edited by Japan Society of Hepatology" and "Aliment Pharmacol Ther, 2011, 33, 525-540").

An index using a blood amino acid concentration for diagnosis of a liver disease is a Fischer ratio "(Leu+Val+Ile)/(Phe+Tyr)" proposed by Fischer, or a BTR index "(Leu+Val+Ile)/Tyr", a simplified form of the Fischer ratio, which is used for the same purpose as that of the Fischer ratio ("Fischer J E, Surgery, 1975, 78, 276-290").

WO 2004/052191, WO 2006/098192 and WO 2009/054351 related to a method of relating the amino acid concentration and a biological state are disclosed as previous patents. In WO 2004/052191, a method of diagnosing a hepatitis using a blood amino acid and an index for the purposes of discriminating between hepatitis-free and hepatitis in hepatitis C are disclosed. WO 2006/129513 related to an apparatus that evaluates a progress of a disease state of hepatic disease using index formula composed of a fractional expression having a concentration of an amino acid as an explanatory variable, is disclosed. WO 2008/015929 related to a method of evaluating a state of metabolic syndrome using amino acid concentration, WO 2009/001862 related to a method of evaluating a state of visceral fat accumulation using amino acid concentration, WO 2009/054350 related to a method of evaluating a state of impaired glucose tolerance using amino acid concentration, and WO 2010/095682 related to a method of evaluating states of apparent obesity, non-apparent obesity and obesity using amino acid concentration, are disclosed.

However, neither correlation of fatty liver, NAFLD, and NASH with a blood amino acid concentration nor application of a blood amino acid concentration to a method for discriminating fatty liver, NAFLD, and NASH has been heretofore reported. The discrimination methods reported in the documents "Guide for Diagnosis of NASH/NAFLD, 2010, edited by Japan Society of Hepatology" and "Aliment Pharmacol Ther, 2011, 33, 525-540" do not have sufficient diagnosis performance, and it is therefore difficult to apply the discrimination method as established diagnosis methods. The Fischer ratio and BTR index reported in the document "Fischer J E, Surgery, 1975, 78, 276-290" are used for diagnosis of hepatic encephalopathy, and therefore sufficient accuracy cannot be achieved when the Fischer ratio and BTR index are used for diagnosis of NAFLD or NASH. When the index formulae disclosed in WO 2004/052191, WO 2006/098192, WO 2009/054351, WO 2006/129513, WO 2008/015929, WO 2009/001862, WO 2009/054350 and WO 2010/095682 are used for diagnosis of NAFLD or NASH, sufficient accuracy cannot be achieved because diagnosis objects are different.

That is, there is the problem that a method for evaluating a state of fatty liver related diseases such as fatty liver, NAFLD, and NASH with a plurality of amino acids as explanatory variables has not been heretofore developed and put to practical use.

SUMMARY OF THE INVENTION

It is an object of the present invention to at least partially solve the problems in the conventional technology. The present invention has been made in view of the problems described above, and an object of the present invention is to provide (i) a method of evaluating fatty liver related disease, a fatty liver related disease-evaluating apparatus, a fatty liver related disease-evaluating method, a fatty liver related disease-evaluating program product, a fatty liver related disease-evaluating system, and an information communication terminal apparatus, which can evaluate accurately a state of the fatty liver related disease by using the amino acid concentration in blood, and (ii) a method of searching for prophylactic/ameliorating substance for fatty liver related disease which can search acculately a substance for preventing the fatty liver related disease or ameliorating a state of the fatty liver related disease by using the method of evaluating fatty liver related disease.

Amino acids are metabolized principally in the liver, and the process of progression from fatty liver to NAFLD and to NASH is considered to strongly correlate with carbohydrate metabolism, lipid metabolism, inflammatory reaction, and oxidation stress response reaction. Therefore, if blood amino acids varying in response to a change in hepatic histological image in a NAFLD or NASH state are identified, and an index formula using as an explanatory variable a concentration of the identified blood amino acids is found, the formula can be widely applied as a simple and convenient and effective method for discrimination of fatty liver, NAFLD, and NASH. Accordingly, the present inventors have conducted extensive studies for solving the problems described above, and resultantly identified an amino acid explanatory variable useful for discrimination of groups positive to fatty liver, NAFLD, and NASH by a concentration of amino acids in blood, and found a multivariate discriminant (function formula, index formula) for optimizing a capability of discriminating between two groups, in which the identified concentration of amino acids is used as an explanatory variable, leading to completion of the present invention.

To solve the problem and achieve the object described above, a method of evaluating fatty liver related disease according to one aspect of the present invention includes an obtaining step of obtaining amino acid concentration data on a concentration value of an amino acid in blood collected from a subject to be evaluated and a concentration value criterion evaluating step of evaluating a state of a fatty liver related disease including at least one of fatty liver, NAFLD (non-alcoholic fatty liver disease), and NASH (non-alcoholic steatohepatitis) in the subject, based on the amino acid concentration data of the subject obtained at the obtaining step.

Another aspect of the present invention is the method of evaluating fatty liver related disease, wherein at the concentration value criterion evaluating step, the state of the NASH in the subject is evaluated based on the concentration value of at least one of Gln, Glu, Pro, Gly, Ala, Leu, Ile, Val, Tyr, Phe, Met, His, Trp, Thr, Asn, and Ser contained in the amino acid concentration data obtained at the obtaining step.

Still another aspect of the present invention is the method of evaluating fatty liver related disease, wherein the concentration value criterion evaluating step further includes a concentration value criterion discriminating step of discriminating between the NASH and NASH-free based on the concentration value of at least one of Gln, Glu, Pro, Gly, Ala, Leu, Ile, Val, Tyr, Phe, Met, His, Trp, Thr, Asn, and Ser contained in the amino acid concentration data obtained at the obtaining step.

Still another aspect of the present invention is the method of evaluating fatty liver related disease, wherein at the concentration value criterion evaluating step, the state of the NAFLD in the subject is evaluated based on the concentration value of at least one of Gln, Glu, Pro, Gly, Ala, Cit, Leu, Ile, Val, Tyr, Phe, Met, His, Trp, Lys, Orn, Ser, Thr, and Asn contained in the amino acid concentration data obtained at the obtaining step.

Still another aspect of the present invention is the method of evaluating fatty liver related disease, wherein the concentration value criterion evaluating step further includes a concentration value criterion discriminating step of discriminating between the NAFLD and NAFLD-free in the subject based on the concentration value of at least one of Gln, Glu, Pro, Gly, Ala, Cit, Leu, Ile, Val, Tyr, Phe, Met, His, Trp, Lys, Orn, Ser, Thr, and Asn contained in the amino acid concentration data obtained at the obtaining step.

Still another aspect of the present invention is the method of evaluating fatty liver related disease, wherein at the concentration value criterion evaluating step, the state of the fatty liver in the subject is evaluated based on the concentration value of at least one of Thr, Ser, Glu, Pro, Gly, Ala, Cit, Leu, Ile, Val, Tyr, Phe, Met, His, Trp, Asn, and Orn contained in the amino acid concentration data obtained at the obtaining step.

Still another aspect of the present invention is the method of evaluating fatty liver related disease, wherein the concentration value criterion evaluating step further includes a concentration value criterion discriminating step of discriminating between the fatty liver and fatty liver-free in the subject based on the concentration value of at least one of Thr, Ser, Glu, Pro, Gly, Ala, Cit, Leu, Ile, Val, Tyr, Phe, Met, His, Trp, Asn, and Orn contained in the amino acid concentration data obtained at the obtaining step.

Still another aspect of the present invention is the method of evaluating fatty liver related disease, wherein at the concentration value criterion evaluating step, the states of the NASH and the NAFLD in the subject are evaluated based on the concentration value of at least one of Gln, Glu, Gly, Ala, Cit, Asn, Trp, Leu, Orn, Phe, Met, Ile, Pro, and ABA contained in the amino acid concentration data obtained at the obtaining step.

Still another aspect of the present invention is the method of evaluating fatty liver related disease, wherein the concentration value criterion evaluating step further includes a concentration value criterion discriminating step of discriminating between the NASH and both of NASH-free and the NAFLD in the subject based on the concentration value of at least one of Gln, Glu, Gly, Ala, Cit, Asn, Trp, Leu, Orn, Phe, Met, Ile, Pro, and ABA contained in the amino acid concentration data obtained at the obtaining step.

Still another aspect of the present invention is the method of evaluating fatty liver related disease, wherein the concentration value criterion evaluating step further includes a discriminant value calculating step of calculating a discriminant value that is a value of a multivariate discriminant containing a concentration of the amino acid as an explanatory variable, based on the amino acid concentration data obtained at the obtaining step and the previously established multivariate discriminant and a discriminant value criterion evaluating step of evaluating the state of the fatty liver related disease in the subject based on the discriminant value calculated at the discriminant value calculating step.

Still another aspect of the present invention is the method of evaluating fatty liver related disease, wherein the multivariate discriminant is any one of a logistic regression equation, a fractional expression, a linear discriminant, a multiple regression equation, a discriminant prepared by a support vector machine, a discriminant prepared by a Mahalanobis' generalized distance method, a discriminant prepared by canonical discriminant analysis, and a discriminant prepared by a decision tree.

Still another aspect of the present invention is the method of evaluating fatty liver related disease, wherein (I) at the discriminant value calculating step, the discriminant value is calculated based on both (i) the concentration value of at least one of Gln, Glu, Pro, Gly, Ala, Leu, Ile, Val, Tyr, Phe, Met, His, Trp, Thr, Asn, and Ser contained in the amino acid concentration data obtained at the obtaining step and (ii) the multivariate discriminant containing at least one of Gln, Glu, Pro, Gly, Ala, Leu, Ile, Val, Tyr, Phe, Met, His, Trp, Thr, Asn, and Ser as the explanatory variable and (II) at the discriminant value criterion evaluating step, the state of the NASH in the subject is evaluated based on the discriminant value calculated at the discriminant value calculating step.

Still another aspect of the present invention is the method of evaluating fatty liver related disease, wherein the discriminant value criterion evaluating step further includes a discriminant value criterion discriminating step of discriminating between the NASH and NASH-free in the subject based on the discriminant value calculated at the discriminant value calculating step.

Still another aspect of the present invention is the method of evaluating fatty liver related disease, wherein the multivariate discriminant is the logistic regression equation containing Glu, Gln, Gly, Ala, Val, and Tyr as the explanatory variables.

Still another aspect of the present invention is the method of evaluating fatty liver related disease, wherein (I) at the discriminant value calculating step, the discriminant value is calculated based on both (i) the concentration value of at least one of Gln, Glu, Pro, Gly, Ala, Cit, Leu, Ile, Val, Tyr, Phe, Met, His, Trp, Lys, Orn, Ser, Thr, and Asn contained in the amino acid concentration data obtained at the obtaining step and (ii) the multivariate discriminant containing at least one of Gln, Glu, Pro, Gly, Ala, Cit, Leu, Ile, Val, Tyr, Phe, Met, His, Trp, Lys, Orn, Ser, Thr, and Asn as the explanatory variable and (II) at the discriminant value criterion evaluating step, the state of the NAFLD in the subject is evaluated based on the discriminant value calculated at the discriminant value calculating step.

Still another aspect of the present invention is the method of evaluating fatty liver related disease, wherein the discriminant value criterion evaluating step further includes a discriminant value criterion discriminating step of discriminating between the NAFLD and NAFLD-free in the subject based on the discriminant value calculated at the discriminant value calculating step.

Still another aspect of the present invention is the method of evaluating fatty liver related disease, wherein the multivariate discriminant is the logistic regression equation containing Ser, Glu, Gly, Val, Tyr, and His as the explanatory variables.

Still another aspect of the present invention is the method of evaluating fatty liver related disease, wherein (I) at the discriminant value calculating step, the discriminant value is calculated based on both (i) the concentration value of at least one of Thr, Ser, Glu, Pro, Gly, Ala, Cit, Leu, Ile, Val, Tyr, Phe, Met, His, Trp, Asn, and Orn contained in the amino acid concentration data obtained at the obtaining step and (ii) the multivariate discriminant containing at least one of Thr, Ser, Glu, Pro, Gly, Ala, Cit, Leu, Ile, Val, Tyr, Phe, Met, His, Trp, Asn, and Orn as the explanatory variable and (II) at the discriminant value criterion evaluating step, the state of the fatty liver in the subject is evaluated based on the discriminant value calculated at the discriminant value calculating step.

Still another aspect of the present invention is the method of evaluating fatty liver related disease, wherein the discriminant value criterion evaluating step further includes a discriminant value criterion discriminating step of discriminating between the fatty liver and fatty liver-free in the subject based on the discriminant value calculated at the discriminant value calculating step.

Still another aspect of the present invention is the method of evaluating fatty liver related disease, wherein the multivariate discriminant is the logistic regression equation containing Ser, Glu, Gly, Ala, Val, and Tyr as the explanatory variables.

Still another aspect of the present invention is the method of evaluating fatty liver related disease, wherein (I) at the discriminant value calculating step, the discriminant value is calculated based on both (i) the concentration value of at least one of Gln, Glu, Gly, Ala, Cit, Asn, Trp, Leu, Orn, Phe, Met, Ile, Pro, and ABA contained in the amino acid concentration data obtained at the obtaining step and (ii) the multivariate discriminant containing at least one of Gln, Glu, Gly, Ala, Cit, Asn, Trp, Leu, Orn, Phe, Met, Ile, Pro, and ABA as the explanatory variable and (II) at the discriminant value criterion evaluating step, the states of the NASH and the NAFLD in the subject are evaluated based on the discriminant value calculated at the discriminant value calculating step.

Still another aspect of the present invention is the method of evaluating fatty liver related disease, wherein the discriminant value criterion evaluating step further includes a discriminant value criterion discriminating step of discriminating between the NASH and both of NASH-free and the NAFLD in the subject based on the discriminant value calculated at the discriminant value calculating step.

Still another aspect of the present invention is the method of evaluating fatty liver related disease, wherein the multivariate discriminant is the logistic regression equation containing Asn, Gln, Gly, Ala, Cit, and Met as the explanatory variables.

Still another aspect of the present invention is the method of evaluating fatty liver related disease, wherein the discriminant value criterion evaluating step further includes a discriminant value criterion discriminating step of discriminating between NAFLD-free, the NASH, and both of NASH-free and the NAFLD in the subject based on the discriminant value calculated at the discriminant value calculating step.

Still another aspect of the present invention is the method of evaluating fatty liver related disease, wherein the multivariate discriminant is the logistic regression equation containing Ser, Glu, Gly, Val, Tyr, and His as the explanatory variables and the logistic regression equation containing Asn, Gln, Gly, Ala, Cit, and Met as the explanatory variables.

A fatty liver related disease-evaluating apparatus according to one aspect of the present invention includes a control unit and a memory unit to evaluate a state of a fatty liver related disease including at least one of fatty liver, NAFLD (non-alcoholic fatty liver disease), and NASH (non-alcoholic steatohepatitis) in a subject to be evaluated. The control unit includes a discriminant value-calculating unit that calculates a discriminant value that is a value of a multivariate discriminant containing a concentration of an amino acid as an explanatory variable, based on both previously obtained amino acid concentration data of the subject on a concentration value of the amino acid and the multivariate discriminant stored in the memory unit and a discriminant value criterion-evaluating unit that evaluates the state of the fatty liver related disease in the subject based on the discriminant value calculated by the discriminant value-calculating unit.

Another aspect of the present invention is the fatty liver related disease-evaluating apparatus, wherein the control unit further may include a multivariate discriminant-preparing unit that prepares the multivariate discriminant stored in the memory unit, based on fatty liver related disease state information containing the amino acid concentration data and fatty liver related disease state index data on an index for indicating the state of the fatty liver related disease, stored in the memory unit. The multivariate discriminant-preparing unit further may include (I) a candidate multivariate discriminant-preparing unit that prepares a candidate multivariate discriminant that is a candidate of the multivariate discriminant, based on a predetermined discriminant-preparing method from the fatty liver related disease state information, (II) a candidate multivariate discriminant-verifying unit that verifies the candidate multivariate discriminant prepared by the candidate multivariate discriminant-preparing unit, based on a predetermined verifying method, and (III) an explanatory variable-selecting unit that selects the explanatory variable of the candidate multivariate discriminant based on a predetermined explanatory variable-selecting method from a verification result obtained by the candidate multivariate discriminant-verifying unit (however, the explanatory variable of the candidate multivariate discriminant may be selected based on the predetermined explanatory variable-selecting method without taking the verification result into consideration), thereby selecting a combination of the amino acid concentration data contained in the fatty liver related disease state information used in preparing the candidate multivariate discriminant. The multivariate discriminant-preparing unit may prepare the multivariate discriminant by selecting the candidate multivariate discriminant used as the multivariate discriminant, from a plurality of the candidate multivariate discriminants, based on the verification results accumulated by repeatedly executing the candidate multivariate discriminant-preparing unit, the candidate multivariate discriminant-verifying unit, and the explanatory variable-selecting unit.

A fatty liver related disease-evaluating method according to one aspect of the present invention is a method of evaluating a state of a fatty liver related disease including at least one of fatty liver, NAFLD (non-alcoholic fatty liver disease), and NASH (non-alcoholic steatohepatitis) in a subject to be evaluated. The method is carried out with an information processing apparatus including a control unit and a memory unit. The method includes (I) a discriminant value calculating step of calculating a discriminant value that is a value of a multivariate discriminant containing a concentration of an amino acid as an explanatory variable, based on both previously obtained amino acid concentration data of the subject on a concentration value of the amino acid and the multivariate discriminant stored in the memory unit and (II) a discriminant value criterion evaluating step of evaluating the state of the fatty liver related disease in the subject based on the discriminant value calculated at the discriminant value calculating step. The steps (I) and (II) are executed by the control unit.

A fatty liver related disease-evaluating program product according to one aspect of the present invention has a non-transitory computer readable medium including programmed instructions for making an information processing apparatus including a control unit and a memory unit execute a method of evaluating a state of a fatty liver related disease including at least one of fatty liver, NAFLD (non-alcoholic fatty liver disease), and NASH (non-alcoholic steatohepatitis) in a subject to be evaluated. The method includes (I) a discriminant value calculating step of calculating a discriminant value that is a value of a multivariate discriminant containing a concentration of an amino acid as an explanatory variable, based on both previously obtained amino acid concentration data of the subject on a concentration value of the amino acid and the multivariate discriminant stored in the memory unit and (II) a discriminant value criterion evaluating step of evaluating the state of the fatty liver related disease in the subject based on the discriminant value calculated at the discriminant value calculating step. The steps (I) and (II) are executed by the control unit.

A non-transitory computer-readable recording medium according to one aspect of the present invention includes the programmed instructions described above.

A fatty liver related disease-evaluating system according to one aspect of the present invention includes (I) a fatty liver related disease-evaluating apparatus including a control unit and a memory unit to evaluate a state of a fatty liver related disease including at least one of fatty liver, NAFLD (non-alcoholic fatty liver disease), and NASH (non-alcoholic steatohepatitis) in a subject to be evaluated and (II) an information communication terminal apparatus including a control unit to provide amino acid concentration data of the subject on a concentration value of an amino acid. The apparatuses are connected to each other communicatively via a network. The control unit of the information communication terminal apparatus includes an amino acid concentration data-sending unit that transmits the amino acid concentration data of the subject to the fatty liver related disease-evaluating apparatus and an evaluation result-receiving unit that receives an evaluation result of the subject on the state of the fatty liver related disease transmitted from the fatty liver related disease-evaluating apparatus. The control unit of the fatty liver related disease-evaluating apparatus includes (I) an amino acid concentration data-receiving unit that receives the amino acid concentration data transmitted from the information communication terminal apparatus, (II) a discriminant value-calculating unit that calculates a discriminant value that is a value of a multivariate discriminant containing a concentration of the amino acid as an explanatory variable, based on the amino acid concentration data received by the amino acid concentration data-receiving unit and the multivariate discriminant stored in the memory unit, (III) a discriminant value criterion-evaluating unit that evaluates the state of the fatty liver related disease in the subject based on the discriminant value calculated by the discriminant value-calculating unit, and (IV) an evaluation result-sending unit that transmits the evaluation result of the subject obtained by the discriminant value criterion-evaluating unit to the information communication terminal apparatus.

An information communication terminal apparatus according to one aspect of the present invention includes a control unit to provide amino acid concentration data of a subject to be evaluated on a concentration value of an amino acid. The information communication terminal apparatus is connected communicatively via a network to a fatty liver related disease-evaluating apparatus that evaluates a state of a fatty liver related disease including at least one of fatty liver, NAFLD (non-alcoholic fatty liver disease), and NASH (non-alcoholic steatohepatitis) in the subject. The control unit includes an amino acid concentration data-sending unit that transmits the amino acid concentration data of the subject to the fatty liver related disease-evaluating apparatus and an evaluation result-receiving unit that receives an evaluation result of the subject on the state of the fatty liver related disease transmitted from the fatty liver related disease-evaluating apparatus. The evaluation result is the result of (I) receiving the amino acid concentration data transmitted from the information communication terminal apparatus, (II) calculating a discriminant value that is a value of a multivariate discriminant containing a concentration of the amino acid as an explanatory variable, based on the received amino acid concentration data and the multivariate discriminant stored in the fatty liver related disease-evaluating apparatus, and (III) evaluating the state of the fatty liver related disease in the subject based on the calculated discriminant value, wherein the (I), (II), and (III) are executed by the fatty liver related disease-evaluating apparatus.

A fatty liver related disease-evaluating apparatus according to one aspect of the present invention includes a control unit and a memory unit to evaluate a state of a fatty liver related disease including at least one of fatty liver, NAFLD (non-alcoholic fatty liver disease), and NASH (non-alcoholic steatohepatitis) in a subject to be evaluated. The fatty liver related disease-evaluating apparatus is connected communicatively via a network to an information communication terminal apparatus that provides amino acid concentration data of the subject on a concentration value of an amino acid. The control unit includes (I) an amino acid concentration data-receiving unit that receives the amino acid concentration data transmitted from the information communication terminal apparatus, (II) a discriminant value-calculating unit that calculates a discriminant value that is a value of a multivariate discriminant containing a concentration of the amino acid as an explanatory variable, based on the amino acid concentration data received by the amino acid concentration data-receiving unit and the multivariate discriminant stored in the memory unit, (III) a discriminant value criterion-evaluating unit that evaluates the state of the fatty liver related disease in the subject based on the discriminant value calculated by the discriminant value-calculating unit, and (IV) an evaluation result-sending unit that transmits an evaluation result of the subject obtained by the discriminant value criterion-evaluating unit to the information communication terminal apparatus.

A method of searching for prophylactic/ameliorating substance for fatty liver related disease according to one aspect of the present invention includes (I) an obtaining step of obtaining amino acid concentration data on a concentration value of an amino acid in blood collected from a subject to be evaluated to which a desired substance group consisting of one or more substances has been administered, (II) a concentration value criterion evaluating step of evaluating a state of a fatty liver related disease including at least one of fatty liver, NAFLD (non-alcoholic fatty liver disease), and NASH (non-alcoholic steatohepatitis) in the subject, based on the amino acid concentration data obtained at the obtaining step, and (III) a judging step of judging whether or not the desired substance group prevents the fatty liver related disease or ameliorates the state of the fatty liver related disease, based on an evaluation result obtained at the concentration value criterion evaluating step.

According to the present invention, the amino acid concentration data on the concentration value of the amino acid in blood collected from the subject is obtained and the state of the fatty liver related disease including at least one of the fatty liver, the NAFLD (non-alcoholic fatty liver disease), and the NASH (non-alcoholic steatohepatitis) in the subject is evaluated based on the obtained amino acid concentration data. Thus, concentrations of amino acids in blood can be utilized to bring about the effect of enabling an accurate evaluation of the state of the fatty liver related disease.

According to the present invention, the state of the NASH in the subject is evaluated based on the concentration value of at least one of Gln, Glu, Pro, Gly, Ala, Leu, Ile, Val, Tyr, Phe, Met, His, Trp, Thr, Asn, and Ser contained in the amino acid concentration data. Thus, the concentrations of the amino acids which among amino acids in blood, are correlated with the state of the NASH can be utilized to bring about the effect of enabling an accurate evaluation of the state of the NASH.

According to the present invention, the discrimination between the NASH and the NASH-free is conducted based on the concentration value of at least one of Gln, Glu, Pro, Gly, Ala, Leu, Ile, Val, Tyr, Phe, Met, His, Trp, Thr, Asn, and Ser contained in the amino acid concentration data. Thus, the concentrations of the amino acids which among amino acids in blood, are useful for the 2-group discrimination between the NASH and the NASH-free can be utilized to bring about the effect of enabling accurately the 2-group discrimination.

According to the present invention, the state of the NAFLD in the subject is evaluated based on the concentration value of at least one of Gln, Glu, Pro, Gly, Ala, Cit, Leu, Ile, Val, Tyr, Phe, Met, His, Trp, Lys, Orn, Ser, Thr, and Asn contained in the amino acid concentration data. Thus, the concentrations of the amino acids which among amino acids in blood, are correlated with the state of the NAFLD can be utilized to bring about the effect of enabling an accurate evaluation of the state of the NAFLD.

According to the present invention, the discrimination between the NAFLD and the NAFLD-free in the subject is conducted based on the concentration value of at least one of Gln, Glu, Pro, Gly, Ala, Cit, Leu, Ile, Val, Tyr, Phe, Met, His, Trp, Lys, Orn, Ser, Thr, and Asn contained in the amino acid concentration data. Thus, the concentrations of the amino acids which among amino acids in blood, are useful for the 2-group discrimination between the NAFLD and the NAFLD-free can be utilized to bring about the effect of enabling accurately the 2-group discrimination.

According to the present invention, the state of the fatty liver in the subject is evaluated based on the concentration value of at least one of Thr, Ser, Glu, Pro, Gly, Ala, Cit, Leu, Ile, Val, Tyr, Phe, Met, His, Trp, Asn, and Orn contained in the amino acid concentration data. Thus, the concentrations of the amino acids which among amino acids in blood, are correlated with the state of the fatty liver can be utilized to bring about the effect of enabling an accurate evaluation of the state of the fatty liver.

According to the present invention, the discrimination between the fatty liver and the fatty liver-free in the subject is conducted based on the concentration value of at least one of Thr, Ser, Glu, Pro, Gly, Ala, Cit, Leu, Ile, Val, Tyr, Phe, Met, His, Trp, Asn, and Orn contained in the amino acid concentration data. Thus, the concentrations of the amino acids which among amino acids in blood, are useful for the 2-group discrimination between the fatty liver and the fatty liver-free can be utilized to bring about the effect of enabling accurately the 2-group discrimination.

According to the present invention, the states of the NASH and the NAFLD in the subject are evaluated based on the concentration value of at least one of Gln, Glu, Gly, Ala, Cit, Asn, Trp, Leu, Orn, Phe, Met, Ile, Pro, and ABA contained in the amino acid concentration data. Thus, the concentrations of the amino acids which among amino acids in blood, are correlated with the states of the NASH and the NAFLD can be utilized to bring about the effect of enabling an accurate evaluation of the states of the NASH and the NAFLD.

According to the present invention, the discrimination between the NASH and the both of the NASH-free and the NAFLD in the subject is conducted based on the concentration value of at least one of Gln, Glu, Gly, Ala, Cit, Asn, Trp, Leu, Orn, Phe, Met, Ile, Pro, and ABA contained in the amino acid concentration data. Thus, the concentrations of the amino acids which among amino acids in blood, are useful for the 2-group discrimination between the NASH and the simple steatosis can be utilized to bring about the effect of enabling accurately the 2-group discrimination.

According to the present invention, the discriminant value that is a value of the multivariate discriminant is calculated based on the amino acid concentration data and the previously established multivariate discriminant containing the concentration of the amino acid as the explanatory variable and then the state of the fatty liver related disease in the subject is evaluated based on the calculated discriminant value. Thus, the discriminant values obtained in the multivariate discriminants containing the concentration of the amino acid as the explanatory variable can be utilized to bring about the effect of enabling an accurate evaluation of the state of the fatty liver related disease.

According to the present invention, the multivariate discriminant is any one of the logistic regression equation, the fractional expression, the linear discriminant, the multiple regression equation, the discriminant prepared by the support vector machine, the discriminant prepared by the Mahalanobis' generalized distance method, the discriminant prepared by the canonical discriminant analysis, and the discriminant prepared by the decision tree. Thus, the discriminant values obtained in the multivariate discriminants containing the concentration of the amino acid as the explanatory variable can be utilized to bring about the effect of enabling a more accurate evaluation of the state of the fatty liver related disease.

According to the present invention, the discriminant value is calculated based on both (i) the concentration value of at least one of Gln, Glu, Pro, Gly, Ala, Leu, Ile, Val, Tyr, Phe, Met, His, Trp, Thr, Asn, and Ser contained in the amino acid concentration data and (ii) the multivariate discriminant containing at least one of Gln, Glu, Pro, Gly, Ala, Leu, Ile, Val, Tyr, Phe, Met, His, Trp, Thr, Asn, and Ser as the explanatory variable and then the state of the NASH in the subject is evaluated based on the calculated discriminant value. Thus, the discriminant values obtained in the multivariate discriminants correlated significantly with the state of the NASH can be utilized to bring about the effect of enabling an accurate evaluation of the state of the NASH.

According to the present invention, the discrimination between the NASH and the NASH-free in the subject is conducted based on the discriminant value. Thus, the discriminant values obtained in the multivariate discriminants useful for the 2-group discrimination between the NASH and the NASH-free can be utilized to bring about the effect of enabling accurately the 2-group discrimination.

According to the present invention, the multivariate discriminant is the logistic regression equation containing Glu, Gln, Gly, Ala, Val, and Tyr as the explanatory variables. Thus, the discriminant values obtained in the multivariate discriminants useful particularly for the 2-group discrimination between the NASH and the NASH-free can be utilized to bring about the effect of enabling more accurately the 2-group discrimination.

According to the present invention, the discriminant value is calculated based on both (i) the concentration value of at least one of Gln, Glu, Pro, Gly, Ala, Cit, Leu, Ile, Val, Tyr, Phe, Met, His, Trp, Lys, Orn, Ser, Thr, and Asn contained in the amino acid concentration data and (ii) the multivariate discriminant containing at least one of Gln, Glu, Pro, Gly, Ala, Cit, Leu, Ile, Val, Tyr, Phe, Met, His, Trp, Lys, Orn, Ser, Thr, and Asn as the explanatory variable and then the state of the NAFLD in the subject is evaluated based on the calculated discriminant value. Thus, the discriminant values obtained in the multivariate discriminants correlated significantly with the state of the NAFLD can be utilized to bring about the effect of enabling an accurate evaluation of the state of the NAFLD.

According to the present invention, the discrimination between the NAFLD and the NAFLD-free in the subject is conducted based on the discriminant value. Thus, the discriminant values obtained in the multivariate discriminants useful for the 2-group discrimination between the NAFLD and the NAFLD-free can be utilized to bring about the effect of enabling accurately the 2-group discrimination.

According to the present invention, the multivariate discriminant is the logistic regression equation containing Ser, Glu, Gly, Val, Tyr, and His as the explanatory variables. Thus, the discriminant values obtained in the multivariate discriminants useful particularly for the 2-group discrimination between the NAFLD and the NAFLD-free can be utilized to bring about the effect of enabling more accurately the 2-group discrimination.

According to the present invention, the discriminant value is calculated based on both (i) the concentration value of at least one of Thr, Ser, Glu, Pro, Gly, Ala, Cit, Leu, Ile, Val, Tyr, Phe, Met, His, Trp, Asn, and Orn contained in the amino acid concentration data and (ii) the multivariate discriminant containing at least one of Thr, Ser, Glu, Pro, Gly, Ala, Cit, Leu, Ile, Val, Tyr, Phe, Met, His, Trp, Asn, and Orn as the explanatory variable and then the state of the fatty liver in the subject is evaluated based on the calculated discriminant value. Thus, the discriminant values obtained in the multivariate discriminants correlated significantly with the state of the fatty liver can be utilized to bring about the effect of enabling an accurate evaluation of the state of the fatty liver.

According to the present invention, the discrimination between the fatty liver and the fatty liver-free in the subject is conducted based on the discriminant value. Thus, the discriminant values obtained in the multivariate discriminants useful for the 2-group discrimination between the fatty liver and the fatty liver-free can be utilized to bring about the effect of enabling accurately the 2-group discrimination.

According to the present invention, the multivariate discriminant is the logistic regression equation containing Ser, Glu, Gly, Ala, Val, and Tyr as the explanatory variables. Thus, the discriminant values obtained in the multivariate discriminants useful particularly for the 2-group discrimination between the fatty liver and the fatty liver-free can be utilized to bring about the effect of enabling more accurately the 2-group discrimination. According to the present invention, the discriminant value is calculated based on both (i) the concentration value of at least one of Gln, Glu, Gly, Ala, Cit, Asn, Trp, Leu, Orn, Phe, Met, Ile, Pro, and ABA contained in the amino acid concentration data and (ii) the multivariate discriminant containing at least one of Gln, Glu, Gly, Ala, Cit, Asn, Trp, Leu, Orn, Phe, Met, Ile, Pro, and ABA as the explanatory variable and then the states of the NASH and the NAFLD in the subject are evaluated based on the calculated discriminant value. Thus, the discriminant values obtained in the multivariate discriminants correlated significantly with the states of the NASH and the NAFLD can be utilized to bring about the effect of enabling an accurate evaluation of the states of the NASH and the NAFLD.

According to the present invention, the discrimination between the NASH and the both of the NASH-free and the NAFLD in the subject is conducted based on the discriminant value. Thus, the discriminant values obtained in the multivariate discriminants useful for the 2-group discrimination between the NASH and the simple steatosis can be utilized to bring about the effect of enabling accurately the 2-group discrimination.

According to the present invention, the multivariate discriminant is the logistic regression equation containing Asn, Gln, Gly, Ala, Cit, and Met as the explanatory variables. Thus, the discriminant values obtained in the multivariate discriminants useful particularly for the 2-group discrimination between the NASH and the simple steatosis can be utilized to bring about the effect of enabling more accurately the 2-group discrimination.

According to the present invention, the discrimination between the NAFLD-free, the NASH, and the both of the NASH-free and the NAFLD in the subject is conducted based on the discriminant value. Thus, the discriminant values obtained in the multivariate discriminants useful for the 3-group discrimination between the NAFLD-free, the NASH, and the simple steatosis can be utilized to bring about the effect of enabling accurately the 3-group discrimination.

According to the present invention, the multivariate discriminant is the logistic regression equation containing Ser, Glu, Gly, Val, Tyr, and His as the explanatory variables and the logistic regression equation containing Asn, Gln, Gly, Ala, Cit, and Met as the explanatory variables. Thus, the discriminant values obtained in the multivariate discriminants useful particularly for the 3-group discrimination between the NAFLD-free, the NASH, and the simple steatosis can be utilized to bring about the effect of enabling more accurately the 3-group discrimination.

According to the present invention, the multivariate discriminant stored in the memory unit may be prepared based on the fatty liver related disease state information containing the amino acid concentration data and the fatty liver related disease state index data on the index for indicating the state of the fatty liver related disease, stored in the memory unit. Specifically, (1) the candidate multivariate discriminant may be prepared based on the predetermined discriminant-preparing method from the fatty liver related disease state information, (2) the prepared candidate multivariate discriminant may be verified based on the predetermined verifying method, (3) the explanatory variables of the candidate multivariate discriminant may be selected based on the predetermined explanatory variable-selecting method from the verification result (however, the explanatory variable of the candidate multivariate discriminant may be selected based on the predetermined explanatory variable-selecting method without taking the verification result into consideration), thereby selecting the combination of the amino acid concentration data contained in the fatty liver related disease state information used in preparing of the candidate multivariate discriminant, and (4) the candidate multivariate discriminant used as the multivariate discriminant may be selected from a plurality of the candidate multivariate discriminants based on the verification results accumulated by repeatedly executing (1), (2) and (3), thereby preparing the multivariate discriminant. Thus, the effect of being able to prepare the multivariate discriminant most appropriate for evaluating the state of the fatty liver related disease is brought about.

According to the present invention, the fatty liver related disease-evaluating program recorded on the recording medium is read and executed by the computer, thereby allowing the computer to execute the fatty liver related disease-evaluating program, thus bringing about the effect of obtaining the effect same as above.

According to the present invention, the amino acid concentration data on the concentration value of the amino acid in blood collected from the subject to which the desired substance group consisting of one or more substances has been administered is obtained, the state of the fatty liver related disease including at least one of the fatty liver, the NAFLD (non-alcoholic fatty liver disease), and the NASH (non-alcoholic steatohepatitis) in the subject is evaluated based on the obtained amino acid concentration data, and whether or not the desired substance group prevents the fatty liver related disease or ameliorates the state of the fatty liver related disease is judged based on the evaluation result. Thus, the method of evaluating fatty liver related disease capable of accurately evaluating the state of the fatty liver related disease by utilizing concentrations of amino acids in blood can be used to bring about an effect of enabling an accurate search for a substance for preventing the fatty liver related disease or ameliorating the state of the fatty liver related disease. According to the present invention, information on amino acid concentration variation pattern typical of the fatty liver related disease or a multivariate discriminant corresponding to the state of the fatty liver related disease can be used for selecting a clinically effective chemical at an early stage or an existing animal model partially reflecting the state of the fatty liver related disease.

When the state of the fatty liver related disease is evaluated in the present invention, another biological information (e.g., biological metabolites such as glucose, lipid, protein, peptide, mineral and hormone, and biological indices such as blood glucose level, blood pressure level, sex, age, hepatic disease index, dietary habit, drinking habit, exercise habit, obesity level and disease history) may be used in addition to the amino acid concentration. When the state of the fatty liver related disease is evaluated in the present invention, another biological information (e.g., biological metabolites such as glucose, lipid, protein, peptide, mineral and hormone, and biological indices such as blood glucose level, blood pressure level, sex, age, hepatic disease index, dietary habit, drinking habit, exercise habit, obesity level and disease history) may be used as the explanatory variables in the multivariate discriminant in addition to the amino acid concentration.

The above and other objects, features, advantages and technical and industrial significance of this invention will be better understood by reading the following detailed description of presently preferred embodiments of the invention, when considered in connection with the accompanying drawings.

BRIEF DESCRIPTION OF THE DRAWINGS

FIG. 7 is a chart showing an example of information stored in a user information file 106a;

FIG. 8 is a chart showing an example of information stored in an amino acid concentration data file 106b;

FIG. 9 is a chart showing an example of information stored in a fatty liver related disease state information file 106c;

FIG. 10 is a chart showing an example of information stored in a designated fatty liver related disease state information file 106d;

FIG. 11 is a chart showing an example of information stored in a candidate multivariable discriminant file 106e1;

FIG. 12 is a chart showing an example of information stored in a verification result file 106e2;

FIG. 13 is a chart showing an example of information stored in a selected fatty liver related disease state information file 106e3;

FIG. 14 is a chart showing an example of information stored in a multivariable discriminant file 106e4;

FIG. 15 is a chart showing an example of information stored in a discriminant value file 106f;

FIG. 25 is a chart showing a list of the logistic regression equations having good discrimination capabilities for a discrimination between a fatty liver positive and a fatty liver negative;

FIG. 26 is a chart showing a list of the logistic regression equations having good discrimination capabilities for the discrimination between the fatty liver positive and the fatty liver negative;

FIG. 27 is a chart showing a list of the fractional expressions having good discrimination capabilities for the discrimination between the fatty liver positive and the fatty liver negative;

FIG. 28 is a chart showing a list of the fractional expressions having good discrimination capabilities for the discrimination between the fatty liver positive and the fatty liver negative;

FIG. 29 is a chart showing a list of the logistic regression equations having good discrimination capabilities for a discrimination between a NAFLD positive and a NAFLD negative;

FIG. 30 is a chart showing a list of the logistic regression equations having good discrimination capabilities for the discrimination between the NAFLD positive and the NAFLD negative;

FIG. 31 is a chart showing a list of the fractional expressions having good discrimination capabilities for the discrimination between the NAFLD positive and the NAFLD negative;

FIG. 32 is a chart showing a list of the fractional expressions having good discrimination capabilities for the discrimination between the NAFLD positive and the NAFLD negative;

FIG. 33 is a chart showing a list of the logistic regression equations having good discrimination capabilities for a discrimination between a NASH positive and a NASH negative;

FIG. 34 is a chart showing a list of the logistic regression equations having good discrimination capabilities for the discrimination between the NASH positive and the NASH negative;

FIG. 35 is a chart showing a list of the fractional expressions having good discrimination capabilities for the discrimination between the NASH positive and the NASH negative;

FIG. 36 is a chart showing a list of the fractional expressions having good discrimination capabilities for the discrimination between the NASH positive and the NASH negative;

FIG. 37 is a chart showing a list of the logistic regression equations having good discrimination capabilities for a discrimination between the NASH positive and a simple steatosis;

FIG. 38 is a chart showing a list of the logistic regression equations having good discrimination capabilities for the discrimination between the NASH positive and the simple steatosis;

FIG. 39 is a chart showing a list of the fractional expressions having good discrimination capabilities for the discrimination between the NASH positive and the simple steatosis;

FIG. 40 is a chart showing a list of the fractional expressions having good discrimination capabilities for the discrimination between the NASH positive and the simple steatosis;

DETAILED DESCRIPTION OF THE PREFERRED EMBODIMENTS

Hereinafter, an embodiment (first embodiment) of the method of evaluating fatty liver related disease of the present invention, an embodiment (second embodiment) of the fatty liver related disease-evaluating apparatus, the fatty liver related disease-evaluating method, the fatty liver related disease-evaluating program product, the recording medium, the fatty liver related disease-evaluating system, and the information communication terminal apparatus of the present invention, and an embodiment (third embodiment) of the method of searching for prophylactic/ameliorating substance for fatty liver related disease of the present invention are described in detail with reference to the drawings. The present invention is not limited to these embodiments.

First Embodiment

1-1. Outline of the Invention

Figure 1:
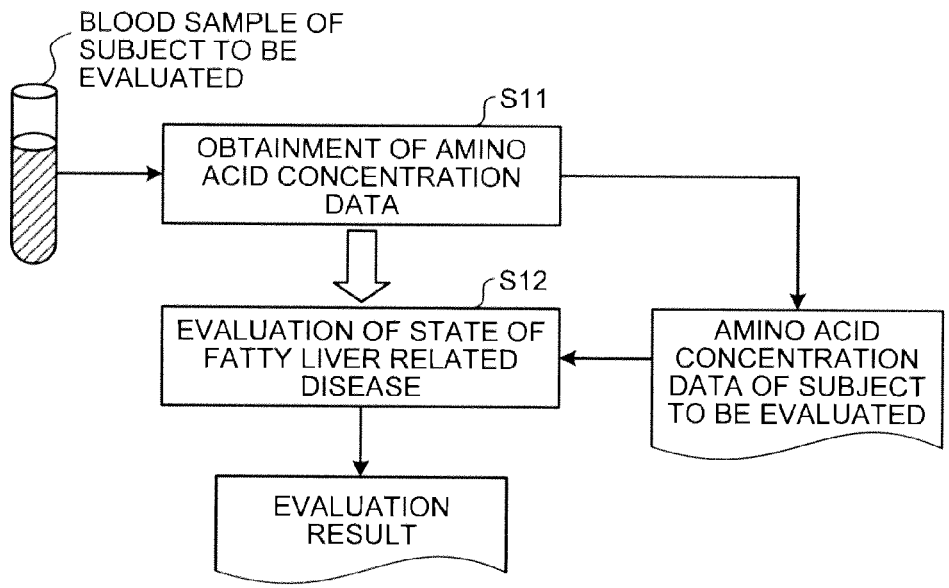
FIG. 1 is a principle configurational diagram showing a basic principle of the present invention.

Here, an outline of the method of evaluating fatty liver related disease of the present invention will be described with reference to FIG. 1. FIG. 1 is a principle configurational diagram showing a basic principle of the present invention.

First, amino acid concentration data on a concentration value of an amino acid in blood (including, for example, plasma, serum, and the like) collected from a subject to be evaluated (for example, an individual such as animal or human) is obtained (step S11). In step S11, for example, the amino acid concentration data determined by a company or the like that performs amino acid concentration measurements may be obtained, or amino acid concentration data may be obtained by determining amino acid concentration data by a measurement method such as, for example, the following method (A) or (B) from blood collected from the subject. Here, the unit of the amino acid concentration may be, for example, a molar concentration, a weight concentration, or one obtained by addition, subtraction, multiplication, and division of any constant with these concentrations.

(A) Plasma is separated from blood by centrifuging a collected blood sample. All plasma samples are frozen and stored at −80° C. until an amino acid concentration is measured. At the time of measuring an amino acid concentration, acetonitrile is added to perform a protein removal treatment, pre-column derivatization is then performed using a labeled reagent (3-aminopyridyl-N-hydroxysuccinimidyl carbamate), and an amino acid concentration is analyzed by liquid chromatograph mass spectrometer (LC-MS) (see International Publication WO 2003/069328 and International Publication WO 2005/116629).

(B) Plasma is separated from blood by centrifuging a collected blood sample. All plasma samples are frozen and stored at −80° C. until an amino acid concentration is measured. At the time of measuring an amino acid concentration, sulfosalicylic acid is added to perform a protein removal treatment, and an amino acid concentration is analyzed by an amino acid analyzer based on post-column derivatization using a ninhydrin reagent.

A state of a fatty liver related disease including at least one of fatty liver, NAFLD (non-alcoholic fatty liver disease), and NASH (non-alcoholic steatohepatitis) in the subject is evaluated based on the amino acid concentration data obtained in step S11 (step S12).

According to the present invention described above, the amino acid concentration data on the concentration value of the amino acid in blood collected from the subject is obtained and the state of the fatty liver related disease including at least one of the fatty liver, the NAFLD, and the NASH in the subject is evaluated based on the measured amino acid concentration data of the subject. Thus, concentrations of amino acids in blood can be utilized to bring about the effect of enabling an accurate evaluation of the state of the fatty liver related disease.

Before step S12 is executed, data such as defective and outliers may be removed from the amino acid concentration data obtained in step S11. Thus, the state of the fatty liver related disease can be more accurately evaluated.

In step S12, the state of the NASH in the subject may be evaluated based on the concentration value of at least one of Gln, Glu, Pro, Gly, Ala, Leu, Ile, Val, Tyr, Phe, Met, His, Trp, Thr, Asn, and Ser contained in the amino acid concentration data obtained in step S11. Thus, the concentrations of the amino acids which among amino acids in blood, are correlated with the state of the NASH can be utilized to bring about the effect of enabling an accurate evaluation of the state of the NASH. Specifically, the discrimination between the NASH and NASH-free may be conducted based on the concentration value of at least one of Gln, Glu, Pro, Gly, Ala, Leu, Ile, Val, Tyr, Phe, Met, His, Trp, Thr, Asn, and Ser contained in the amino acid concentration data. Thus, the concentrations of the amino acids which among amino acids in blood, are useful for the 2-group discrimination between the NASH and the NASH-free can be utilized to bring about the effect of enabling accurately the 2-group discrimination.

In step S12, the state of the NAFLD in the subject may be evaluated based on the concentration value of at least one of Gln, Glu, Pro, Gly, Ala, Cit, Leu, Ile, Val, Tyr, Phe, Met, His, Trp, Lys, Orn, Ser, Thr, and Asn contained in the amino acid concentration data obtained in step S11. Thus, the concentrations of the amino acids which among amino acids in blood, are correlated with the state of the NAFLD can be utilized to bring about the effect of enabling an accurate evaluation of the state of the NAFLD. Specifically, the discrimination between the NAFLD and NAFLD-free in the subject may be conducted based on the concentration value of at least one of Gln, Glu, Pro, Gly, Ala, Cit, Leu, Ile, Val, Tyr, Phe, Met, His, Trp, Lys, Orn, Ser, Thr, and Asn contained in the amino acid concentration data. Thus, the concentrations of the amino acids which among amino acids in blood, are useful for the 2-group discrimination between the NAFLD and the NAFLD-free can be utilized to bring about the effect of enabling accurately the 2-group discrimination.

In step S12, the state of the fatty liver in the subject may be evaluated based on the concentration value of at least one of Thr, Ser, Glu, Pro, Gly, Ala, Cit, Leu, Ile, Val, Tyr, Phe, Met, His, Trp, Asn, and Orn contained in the amino acid concentration data obtained in step S11. Thus, the concentrations of the amino acids which among amino acids in blood, are correlated with the state of the fatty liver can be utilized to bring about the effect of enabling an accurate evaluation of the state of the fatty liver. Specifically, the discrimination between the fatty liver and fatty liver-free in the subject may be conducted based on the concentration value of at least one of Thr, Ser, Glu, Pro, Gly, Ala, Cit, Leu, Ile, Val, Tyr, Phe, Met, His, Trp, Asn, and Orn contained in the amino acid concentration data. Thus, the concentrations of the amino acids which among amino acids in blood, are useful for the 2-group discrimination between the fatty liver and the fatty liver-free can be utilized to bring about the effect of enabling accurately the 2-group discrimination.

In step S12, the states of the NASH and the NAFLD in the subject may be evaluated based on the concentration value of at least one of Gln, Glu, Gly, Ala, Cit, Asn, Trp, Leu, Orn, Phe, Met, Ile, Pro, and ABA contained in the amino acid concentration data obtained in step S11. Thus, the concentrations of the amino acids which among amino acids in blood, are correlated with the states of the NASH and the NAFLD can be utilized to bring about the effect of enabling an accurate evaluation of the states of the NASH and the NAFLD. Specifically, the discrimination between the NASH and both of the NASH-free and the NAFLD in the subject may be conducted based on the concentration value of at least one of Gln, Glu, Gly, Ala, Cit, Asn, Trp, Leu, Orn, Phe, Met, Ile, Pro, and ABA contained in the amino acid concentration data. Thus, the concentrations of the amino acids which among amino acids in blood, are useful for the 2-group discrimination between the NASH and the simple steatosis can be utilized to bring about the effect of enabling accurately the 2-group discrimination.

In step S12, a discriminant value that is a value of a multivariate discriminant containing a concentration of the amino acid as an explanatory variable may be calculated based on the amino acid concentration data obtained in step S11 and the previously established multivariate discriminant and then the state of the fatty liver related disease in the subject may be evaluated based on the calculated discriminant value. Thus, the discriminant values obtained in the multivariate discriminants containing the concentration of the amino acid as the explanatory variable can be utilized to bring about the effect of enabling an accurate evaluation of the state of the fatty liver related disease.

The multivariate discriminant may be any one of the logistic regression equation, the fractional expression, the linear discriminant, the multiple regression equation, the discriminant prepared by the support vector machine, the discriminant prepared by the Mahalanobis' generalized distance method, the discriminant prepared by the canonical discriminant analysis, and the discriminant prepared by the decision tree. Thus, the discriminant values obtained in the multivariate discriminants containing the concentration of the amino acid as the explanatory variable can be utilized to bring about the effect of enabling a more accurate evaluation of the state of the fatty liver related disease.

In step S12, the discriminant value may be calculated based on both (i) the concentration value of at least one of Gln, Glu, Pro, Gly, Ala, Leu, Ile, Val, Tyr, Phe, Met, His, Trp, Thr, Asn, and Ser contained in the amino acid concentration data obtained in step S11 and (ii) the multivariate discriminant containing at least one of Gln, Glu, Pro, Gly, Ala, Leu, Ile, Val, Tyr, Phe, Met, His, Trp, Thr, Asn, and Ser as the explanatory variable and then the state of the NASH in the subject may be evaluated based on the calculated discriminant value. Thus, the discriminant values obtained in the multivariate discriminants correlated significantly with the state of the NASH can be utilized to bring about the effect of enabling an accurate evaluation of the state of the NASH. Specifically, the discrimination between the NASH and the NASH-free in the subject may be conducted based on the discriminant value. Thus, the discriminant values obtained in the multivariate discriminants useful for the 2-group discrimination between the NASH and the NASH-free can be utilized to bring about the effect of enabling accurately the 2-group discrimination. The multivariate discriminant may be the logistic regression equation containing Glu, Gln, Gly, Ala, Val, and Tyr as the explanatory variables. Thus, the discriminant values obtained in the multivariate discriminants useful particularly for the 2-group discrimination between the NASH and the NASH-free can be utilized to bring about the effect of enabling more accurately the 2-group discrimination.

In step S12, the discriminant value may be calculated based on both (i) the concentration value of at least one of Gln, Glu, Pro, Gly, Ala, Cit, Leu, Ile, Val, Tyr, Phe, Met, His, Trp, Lys, Orn, Ser, Thr, and Asn contained in the amino acid concentration data obtained in step S11 and (ii) the multivariate discriminant containing at least one of Gln, Glu, Pro, Gly, Ala, Cit, Leu, Ile, Val, Tyr, Phe, Met, His, Trp, Lys, Orn, Ser, Thr, and Asn as the explanatory variable and then the state of the NAFLD in the subject may be evaluated based on the calculated discriminant value. Thus, the discriminant values obtained in the multivariate discriminants correlated significantly with the state of the NAFLD can be utilized to bring about the effect of enabling an accurate evaluation of the state of the NAFLD. Specifically, the discrimination between the NAFLD and the NAFLD-free in the subject may be conducted based on the discriminant value. Thus, the discriminant values obtained in the multivariate discriminants useful for the 2-group discrimination between the NAFLD and the NAFLD-free can be utilized to bring about the effect of enabling accurately the 2-group discrimination. The multivariate discriminant may be the logistic regression equation containing Ser, Glu, Gly, Val, Tyr, and His as the explanatory variables. Thus, the discriminant values obtained in the multivariate discriminants useful particularly for the 2-group discrimination between the NAFLD and the NAFLD-free can be utilized to bring about the effect of enabling more accurately the 2-group discrimination.

In step S12, the discriminant value may be calculated based on both (i) the concentration value of at least one of Thr, Ser, Glu, Pro, Gly, Ala, Cit, Leu, Ile, Val, Tyr, Phe, Met, His, Trp, Asn, and Orn contained in the amino acid concentration data obtained in step S11 and (ii) the multivariate discriminant containing at least one of Thr, Ser, Glu, Pro, Gly, Ala, Cit, Leu, Ile, Val, Tyr, Phe, Met, His, Trp, Asn, and Orn as the explanatory variable and then the state of the fatty liver in the subject may be evaluated based on the calculated discriminant value. Thus, the discriminant values obtained in the multivariate discriminants correlated significantly with the state of the fatty liver can be utilized to bring about the effect of enabling an accurate evaluation of the state of the fatty liver. Specifically, the discrimination between the fatty liver and the fatty liver-free in the subject may be conducted based on the discriminant value. Thus, the discriminant values obtained in the multivariate discriminants useful for the 2-group discrimination between the fatty liver and the fatty liver-free can be utilized to bring about the effect of enabling accurately the 2-group discrimination. The multivariate discriminant may be the logistic regression equation containing Ser, Glu, Gly, Ala, Val, and Tyr as the explanatory variables. Thus, the discriminant values obtained in the multivariate discriminants useful particularly for the 2-group discrimination between the fatty liver and the fatty liver-free can be utilized to bring about the effect of enabling more accurately the 2-group discrimination.

In step S12, the discriminant value may be calculated based on both (i) the concentration value of at least one of Gln, Glu, Gly, Ala, Cit, Asn, Trp, Leu, Orn, Phe, Met, Ile, Pro, and ABA contained in the amino acid concentration data obtained in step S11 and (ii) the multivariate discriminant containing at least one of Gln, Glu, Gly, Ala, Cit, Asn, Trp, Leu, Orn, Phe, Met, Ile, Pro, and ABA as the explanatory variable and then the states of the NASH and the NAFLD in the subject may be evaluated based on the calculated discriminant value. Thus, the discriminant values obtained in the multivariate discriminants correlated significantly with the states of the NASH and the NAFLD can be utilized to bring about the effect of enabling an accurate evaluation of the states of the NASH and the NAFLD. Specifically, the discrimination between the NASH and the "both of the NASH-free and the NAFLD" (the simple steatosis) in the subject may be conducted based on the discriminant value. Thus, the discriminant values obtained in the multivariate discriminants useful for the 2-group discrimination between the NASH and the simple steatosis can be utilized to bring about the effect of enabling accurately the 2-group discrimination. The multivariate discriminant may be the logistic regression equation containing Asn, Gln, Gly, Ala, Cit, and Met as the explanatory variables. Thus, the discriminant values obtained in the multivariate discriminants useful particularly for the 2-group discrimination between the NASH and the simple steatosis can be utilized to bring about the effect of enabling more accurately the 2-group discrimination. Specifically, the discrimination between the NAFLD-free, the NASH, and the "both of the NASH-free and the NAFLD" in the subject may be conducted based on the discriminant value. Thus, the discriminant values obtained in the multivariate discriminants useful for the 3-group discrimination between the NAFLD-free, the NASH, and the simple steatosis can be utilized to bring about the effect of enabling accurately the 3-group discrimination. The multivariate discriminant may be the logistic regression equation containing Ser, Glu, Gly, Val, Tyr, and His as the explanatory variables and the logistic regression equation containing Asn, Gln, Gly, Ala, Cit, and Met as the explanatory variables. Thus, the discriminant values obtained in the multivariate discriminants useful particularly for the 3-group discrimination between the NAFLD-free, the NASH, and the simple steatosis can be utilized to bring about the effect of enabling more accurately the 3-group discrimination.

The multivariate discriminant described above may be prepared by a method described in International Publication WO 2004/052191 that is an international application filed by the present applicant or by a method (multivariate discriminant-preparing processing described in the second embodiment described later) described in International Publication WO 2006/098192 that is an international application filed by the present applicant. Any multivariate discriminants obtained by these methods can be preferably used in the evaluation of the state of the fatty liver related disease, regardless of the unit of the amino acid concentration in the amino acid concentration data as input data.

The multivariate discriminant refers to a form of equation used generally in multivariate analysis and includes, for example, fractional expression, multiple regression equation, multiple logistic regression equation, linear discriminant function, Mahalanobis' generalized distance, canonical discriminant function, support vector machine, and decision tree. The multivariate discriminant also includes an equation shown by the sum of different forms of multivariate discriminants. In the multiple regression equation, multiple logistic regression equation and canonical discriminant function, a coefficient and constant term are added to each explanatory variable, and the coefficient and constant term in this case are preferably real numbers, more preferably values in the range of 99% confidence interval for the coefficient and constant term obtained from data for discrimination, more preferably in the range of 95% confidence interval for the coefficient and constant term obtained from data for discrimination. The value of each coefficient and the confidence interval thereof may be those multiplied by a real number, and the value of each constant term and the confidence interval thereof may be those having an arbitrary actual constant added or subtracted or those multiplied or divided by an arbitrary actual constant. When an expression such as a logistic regression, a linear discriminant, and a multiple regression analysis is used as an index, a linear transformation of the expression (addition of a constant and multiplication by a constant) and a monotonic increasing (decreasing) transformation (for example, a logit transformation) of the expression do not alter discrimination capability, and thus are equivalent. Therefore, the expression includes an expression that is subjected to a linear transformation and a monotonic increasing (decreasing) transformation.

In the fractional expression, the numerator of the fractional expression is expressed by the sum of the amino acids A, B, C etc. and the denominator of the fractional expression is expressed by the sum of the amino acids a, b, c etc. The fractional expression also includes the sum of the fractional expressions $\alpha$, $\beta$, $\gamma$ etc. (for example, $\alpha+\beta$) having such constitution. The fractional expression also includes divided fractional expressions. The amino acids used in the numerator or denominator may have suitable coefficients respectively. The amino acids used in the numerator or denominator may appear repeatedly. Each fractional expression may have a suitable coefficient. A value of a coefficient for each explanatory variable and a value for a constant term may be any real numbers. In combinations where explanatory variables in the numerator and explanatory variables in the denominator in the fractional expression are switched with each other, the positive (or negative) sign is generally reversed in correlation with objective explanatory variables, but because their correlation is maintained, such combinations can be assumed to be equivalent to one another in discrimination, and thus the fractional expression also includes combinations where explanatory variables in the numerator and explanatory variables in the denominator in the fractional expression are switched with each other.

When the state of the fatty liver related disease is evaluated in the present invention, another biological information (e.g., biological metabolites such as glucose, lipid, protein, peptide, mineral and hormone, and biological indices such as blood glucose level, blood pressure level, sex, age, hepatic disease index, dietary habit, drinking habit, exercise habit, obesity level and disease history) may be used in addition to the amino acid concentration. When the state of the fatty liver related disease is evaluated in the present invention, another biological information (e.g., biological metabolites such as glucose, lipid, protein, peptide, mineral and hormone, and biological indices such as blood glucose level, blood pressure level, sex, age, hepatic disease index, dietary habit, drinking habit, exercise habit, obesity level and disease history) may be used as the explanatory variables in the multivariate discriminant in addition to the amino acid concentration.

Figure 2:
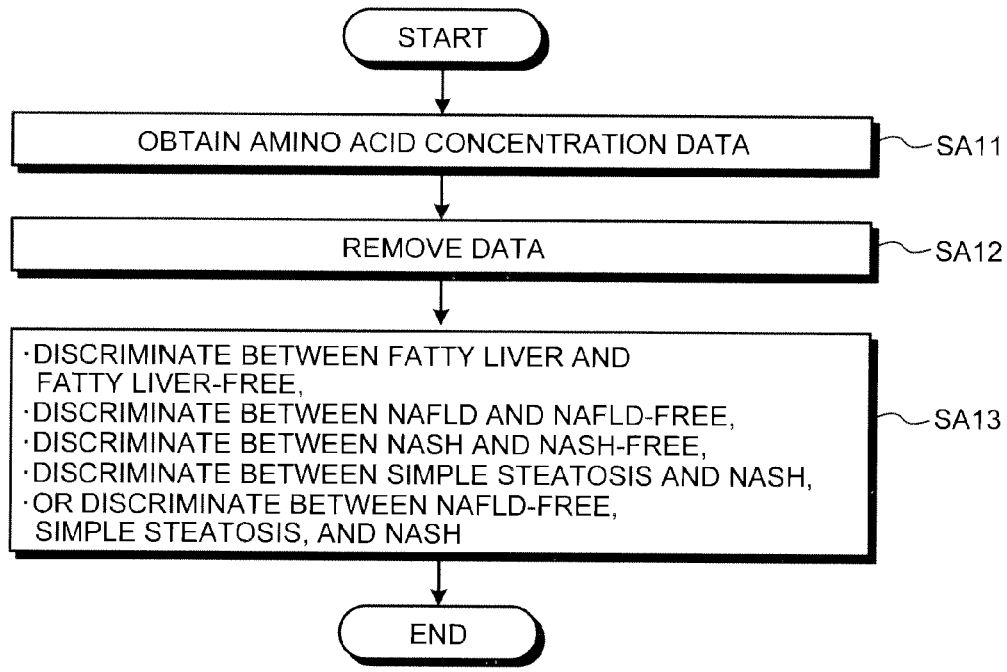
FIG. 2 is a flowchart showing one example of a method of evaluating fatty liver related disease according to a first embodiment.

1-2. Method of Evaluating Fatty Liver Related Disease in Accordance with the First Embodiment Herein, the method of evaluating fatty liver related disease according to the first embodiment is described with reference to FIG. 2. FIG. 2 is a flowchart showing one example of the method of evaluating fatty liver related disease according to the first embodiment.

The amino acid concentration data on the concentration value of the amino acid in blood collected from an individual such as animal or human is obtained (step SA11). In step SA11, for example, the amino acid concentration data determined by a company or the like that performs amino acid concentration measurements may be obtained, or amino acid concentration data may be obtained by determining amino acid concentration data by a measurement method such as, for example, the above described (A) or (B) from blood collected from the subject.

Data such as defective and outliers is then removed from the amino acid concentration data of the individual obtained in step SA11 (step SA12).

Then, any one of the discriminations described in the following 11. to 15. is conducted in the individual, based on the amino acid concentration data of the individual from which the data such as the defective and the outliers have been removed in step SA12 (step SA13).

11. Discrimination Between NASH and NASH-Free (I) the concentration value of at least one of Gln, Glu, Pro, Gly, Ala, Leu, Ile, Val, Tyr, Phe, Met, His, Trp, Thr, Asn, and Ser contained in the amino acid concentration data is compared with a previously established threshold (cutoff value), thereby discriminating between the NASH and the NASH-free in the individual, or (II) the discriminant value is calculated based on both (i) the concentration value of at least one of Gln, Glu, Pro, Gly, Ala, Leu, Ile, Val, Tyr, Phe, Met, His, Trp, Thr, Asn, and Ser contained in the amino acid concentration data and (ii) the multivariate discriminant containing at least one of Gln, Glu, Pro, Gly, Ala, Leu, Ile, Val, Tyr, Phe, Met, His, Trp, Thr, Asn, and Ser as the explanatory variable, and then the calculated discriminant value is compared with a previously established threshold (cutoff value), thereby discriminating between the NASH and the NASH-free in the individual.

12. Discrimination Between NAFLD and NAFLD-Free (I) the concentration value of at least one of Gln, Glu, Pro, Gly, Ala, Cit, Leu, Ile, Val, Tyr, Phe, Met, His, Trp, Lys, Orn, Ser, Thr, and Asn contained in the amino acid concentration data is compared with a previously established threshold (cutoff value), thereby discriminating between the NAFLD and the NAFLD-free in the individual, or (II) the discriminant value is calculated based on both (i) the concentration value of at least one of Gln, Glu, Pro, Gly, Ala, Cit, Leu, Ile, Val, Tyr, Phe, Met, His, Trp, Lys, Orn, Ser, Thr, and Asn contained in the amino acid concentration data and (ii) the multivariate discriminant containing at least one of Gln, Glu, Pro, Gly, Ala, Cit, Leu, Ile, Val, Tyr, Phe, Met, His, Trp, Lys, Orn, Ser, Thr, and Asn as the explanatory variable, and then the calculated discriminant value is compared with a previously established threshold (cutoff value), thereby discriminating between the NAFLD and the NAFLD-free in the individual.

13. Discrimination Between Fatty Liver and Fatty Liver-Free (I) the concentration value of at least one of Thr, Ser, Glu, Pro, Gly, Ala, Cit, Leu, Ile, Val, Tyr, Phe, Met, His, Trp, Asn, and Orn contained in the amino acid concentration data is compared with a previously established threshold (cutoff value), thereby discriminating between the fatty liver and the fatty liver-free in the individual, or (II) the discriminant value is calculated based on both (i) the concentration value of at least one of Thr, Ser, Glu, Pro, Gly, Ala, Cit, Leu, Ile, Val, Tyr, Phe, Met, His, Trp, Asn, and Orn contained in the amino acid concentration data and (ii) the multivariate discriminant containing at least one of Thr, Ser, Glu, Pro, Gly, Ala, Cit, Leu, Ile, Val, Tyr, Phe, Met, His, Trp, Asn, and Orn as the explanatory variable, and then the calculated discriminant value is compared with a previously established threshold (cutoff value), thereby discriminating between the fatty liver and the fatty liver-free in the individual.

14. Discrimination Between NASH and Simple Steatosis (I) the concentration value of at least one of Gln, Glu, Gly, Ala, Cit, Asn, Trp, Leu, Orn, Phe, Met, Ile, Pro, and ABA contained in the amino acid concentration data is compared with a previously established threshold (cutoff value), thereby discriminating between the NASH and the simple steatosis (the both of the NASH-free and the NAFLD) in the individual, or (II) the discriminant value is calculated based on both (i) the concentration value of at least one of Gln, Glu, Gly, Ala, Cit, Asn, Trp, Leu, Orn, Phe, Met, Ile, Pro, and ABA contained in the amino acid concentration data and (ii) the multivariate discriminant containing at least one of Gln, Glu, Gly, Ala, Cit, Asn, Trp, Leu, Orn, Phe, Met, Ile, Pro, and ABA as the explanatory variable, and then the calculated discriminant value is compared with a previously established threshold (cutoff value), thereby discriminating between the NASH and the simple steatosis (the both of the NASH-free and the NAFLD) in the individual.

15. Discrimination Between NASH, Simple Steatosis, and NAFLD-free

The discriminant value is calculated based on both (i) the concentration value of at least one of Gln, Glu, Gly, Ala, Cit, Asn, Trp, Leu, Orn, Phe, Met, Ile, Pro, and ABA contained in the amino acid concentration data and (ii) the multivariate discriminant containing at least one of Gln, Glu, Gly, Ala, Cit, Asn, Trp, Leu, Orn, Phe, Met, Ile, Pro, and ABA as the explanatory variable, and then the calculated discriminant value is compared with a previously established threshold (cutoff value), thereby discriminating between the NAFLD-free, the NASH, and the simple steatosis (the both of the NASH-free and the NAFLD) in the individual.

1-3. Summary of the First Embodiment and Other Embodiments

In the method of evaluating fatty liver related disease to the first embodiment as described above in detail, (I) the amino acid concentration data in the blood collected from the individual is obtained, (II) the data such as the defective and the outliers is removed from the obtained amino acid concentration data of the individual, and (III) any one of the discriminations 11. to 15. described above is conducted in the individual, based on the amino acid concentration data of the individual from which the data such as the defective and the outliers have been removed. Thus, the concentrations of the amino acids which among amino acids in blood, are useful for the 2-group discrimination between the NASH and the NASH-free, the 2-group discrimination between the NAFLD and the NAFLD-free, the 2-group discrimination between the fatty liver and the fatty liver-free, or the 2-group discrimination between the NASH and the simple steatosis, can be utilized to bring about the effect of enabling accurately these 2-group discriminations. The discriminant values obtained in the multivariate discriminants useful for the 2-group discrimination between the NASH and the NASH-free, the 2-group discrimination between the NAFLD and the NAFLD-free, the 2-group discrimination between the fatty liver and the fatty liver-free, the 2-group discrimination between the NASH and the simple steatosis, or the 3-group discrimination between the NAFLD-free, the NASH, and the simple steatosis, can be utilized to bring about the effect of enabling accurately these 2-group discriminations or the 3-group discrimination.

The multivariate discriminant used in step SA13 may be any one of the logistic regression equation, the fractional expression, the linear discriminant, the multiple regression equation, the discriminant prepared by the support vector machine, the discriminant prepared by the Mahalanobis' generalized distance method, the discriminant prepared by the canonical discriminant analysis, and the discriminant prepared by the decision tree. Thus, the discriminant values obtained in the multivariate discriminants useful for the 2-group discrimination between the NASH and the NASH-free, the 2-group discrimination between the NAFLD and the NAFLD-free, the 2-group discrimination between the fatty liver and the fatty liver-free, the 2-group discrimination between the NASH and the simple steatosis, or the 3-group discrimination between the NAFLD-free, the NASH, and the simple steatosis, can be utilized to bring about the effect of enabling more accurately these 2-group discriminations or the 3-group discrimination.

Specifically, the multivariate discriminant used in the above described discrimination 11. may be the logistic regression equation containing Glu, Gln, Gly, Ala, Val, and Tyr as the explanatory variables. Thus, the discriminant values obtained in the multivariate discriminants useful particularly for the 2-group discrimination between the NASH and the NASH-free can be utilized to bring about the effect of enabling more accurately the 2-group discrimination. The multivariate discriminant used in the above described discrimination 12. may be the logistic regression equation containing Ser, Glu, Gly, Val, Tyr, and His as the explanatory variables. Thus, the discriminant values obtained in the multivariate discriminants useful particularly for the 2-group discrimination between the NAFLD and the NAFLD-free can be utilized to bring about the effect of enabling more accurately the 2-group discrimination. The multivariate discriminant used in the above described discrimination 13. may be the logistic regression equation containing Ser, Glu, Gly, Ala, Val, and Tyr as the explanatory variables. Thus, the discriminant values obtained in the multivariate discriminants useful particularly for the 2-group discrimination between the fatty liver and the fatty liver-free can be utilized to bring about the effect of enabling more accurately the 2-group discrimination. The multivariate discriminant used in the above described discrimination 14. may be the logistic regression equation containing Asn, Gln, Gly, Ala, Cit, and Met as the explanatory variables. Thus, the discriminant values obtained in the multivariate discriminants useful particularly for the 2-group discrimination between the NASH and the simple steatosis can be utilized to bring about the effect of enabling more accurately the 2-group discrimination. The multivariate discriminant used in the above described discrimination 15. may be the logistic regression equation containing Ser, Glu, Gly, Val, Tyr, and His as the explanatory variables and the logistic regression equation containing Asn, Gln, Gly, Ala, Cit, and Met as the explanatory variables. Thus, the discriminant values obtained in the multivariate discriminants useful particularly for the 3-group discrimination between the NAFLD-free, the NASH, and the simple steatosis can be utilized to bring about the effect of enabling more accurately the 3-group discrimination.

The multivariate discriminant described above may be prepared by a method described in International Publication WO 2004/052191 that is an international application filed by the present applicant or by a method (multivariate discriminant-preparing processing described in the second embodiment described later) described in International Publication WO 2006/098192 that is an international application filed by the present applicant. Any multivariate discriminants obtained by these methods can be preferably used in the evaluation of the state of the fatty liver related disease, regardless of the unit of the amino acid concentration in the amino acid concentration data as input data.

Second Embodiment 2-1. Outline of the Invention

Figure 3:
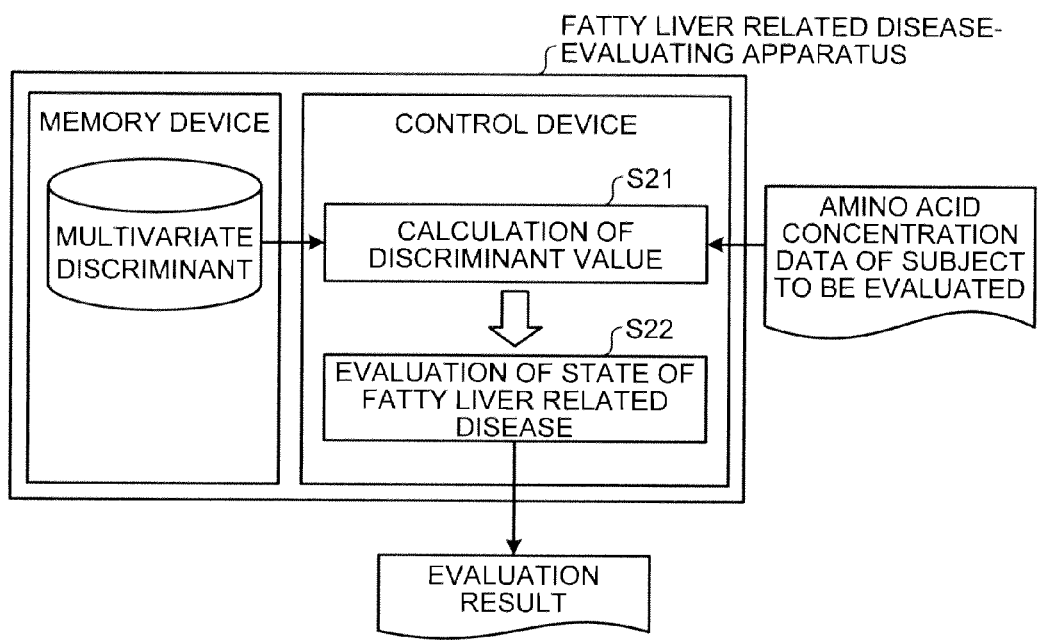
FIG. 3 is a principle configurational diagram showing a basic principle of the present invention.

Herein, outlines of the fatty liver related disease-evaluating apparatus, the fatty liver related disease-evaluating method, the fatty liver related disease-evaluating program product, the recording medium, the fatty liver related disease-evaluating system, and the information communication terminal apparatus of the present invention will be described in detail with reference to FIG. 3. FIG. 3 is a principle configurational diagram showing a basic principle of the present invention.

In the present invention, a discriminant value that is a value of a multivariate discriminant containing a concentration of an amino acid as an explanatory variable is calculated in a control device, based on previously obtained amino acid concentration data on a concentration value of the amino acid of a subject to be evaluated (for example, an individual such as animal or human) and the multivariate discriminant stored in a memory device (step S21).

In the present invention, a state of a fatty liver related disease including at least one of fatty liver, NAFLD (non-alcoholic fatty liver disease), and NASH (non-alcoholic steatohepatitis) in the subject is evaluated in the control device based on the discriminant value calculated in step S21 (step S22).

According to the present invention described above, the discriminant value that is the value of the multivariate discriminant is calculated based on the amino acid concentration data of the subject and the multivariate discriminant containing the concentration of the amino acid as the explanatory variable and then the state of the fatty liver related disease including at least one of the fatty liver, the NAFLD, and the NASH in the subject is evaluated based on the calculated discriminant value. Thus, the discriminant values obtained in the multivariate discriminants containing the concentration of the amino acid as the explanatory variable can be utilized to bring about the effect of enabling an accurate evaluation of the state of the fatty liver related disease.

The multivariate discriminant may be any one of the logistic regression equation, the fractional expression, the linear discriminant, the multiple regression equation, the discriminant prepared by the support vector machine, the discriminant prepared by the Mahalanobis' generalized distance method, the discriminant prepared by the canonical discriminant analysis, and the discriminant prepared by the decision tree. Thus, the discriminant values obtained in the multivariate discriminants containing the concentration of the amino acid as the explanatory variable can be utilized to bring about the effect of enabling a more accurate evaluation of the state of the fatty liver related disease.

In step S21, the discriminant value may be calculated based on both (i) the concentration value of at least one of Gln, Glu, Pro, Gly, Ala, Leu, Ile, Val, Tyr, Phe, Met, His, Trp, Thr, Asn, and Ser contained in the amino acid concentration data and (ii) the multivariate discriminant containing at least one of Gln, Glu, Pro, Gly, Ala, Leu, Ile, Val, Tyr, Phe, Met, His, Trp, Thr, Asn, and Ser as the explanatory variable and then in step S22 the state of the NASH in the subject may be evaluated based on the discriminant value calculated in step S21. Thus, the discriminant values obtained in the multivariate discriminants correlated significantly with the state of the NASH can be utilized to bring about the effect of enabling an accurate evaluation of the state of the NASH. Specifically, the discrimination between the NASH and NASH-free in the subject may be conducted based on the discriminant value. Thus, the discriminant values obtained in the multivariate discriminants useful for the 2-group discrimination between the NASH and the NASH-free can be utilized to bring about the effect of enabling accurately the 2-group discrimination. The multivariate discriminant may be the logistic regression equation containing Glu, Gln, Gly, Ala, Val, and Tyr as the explanatory variables. Thus, the discriminant values obtained in the multivariate discriminants useful particularly for the 2-group discrimination between the NASH and the NASH-free can be utilized to bring about the effect of enabling more accurately the 2-group discrimination.

In step S21, the discriminant value may be calculated based on both (i) the concentration value of at least one of Gln, Glu, Pro, Gly, Ala, Cit, Leu, Ile, Val, Tyr, Phe, Met, His, Trp, Lys, Orn, Ser, Thr, and Asn contained in the amino acid concentration data and (ii) the multivariate discriminant containing at least one of Gln, Glu, Pro, Gly, Ala, Cit, Leu, Ile, Val, Tyr, Phe, Met, His, Trp, Lys, Orn, Ser, Thr, and Asn as the explanatory variable and then in step S22 the state of the NAFLD in the subject may be evaluated based on the discriminant value calculated in step S21. Thus, the discriminant values obtained in the multivariate discriminants correlated significantly with the state of the NAFLD can be utilized to bring about the effect of enabling an accurate evaluation of the state of the NAFLD. Specifically, the discrimination between the NAFLD and NAFLD-free in the subject may be conducted based on the discriminant value. Thus, the discriminant values obtained in the multivariate discriminants useful for the 2-group discrimination between the NAFLD and the NAFLD-free can be utilized to bring about the effect of enabling accurately the 2-group discrimination. The multivariate discriminant may be the logistic regression equation containing Ser, Glu, Gly, Val, Tyr, and His as the explanatory variables. Thus, the discriminant values obtained in the multivariate discriminants useful particularly for the 2-group discrimination between the NAFLD and the NAFLD-free can be utilized to bring about the effect of enabling more accurately the 2-group discrimination.

In step S21, the discriminant value may be calculated based on both (i) the concentration value of at least one of Thr, Ser, Glu, Pro, Gly, Ala, Cit, Leu, Ile, Val, Tyr, Phe, Met, His, Trp, Asn, and Orn contained in the amino acid concentration data and (ii) the multivariate discriminant containing at least one of Thr, Ser, Glu, Pro, Gly, Ala, Cit, Leu, Ile, Val, Tyr, Phe, Met, His, Trp, Asn, and Orn as the explanatory variable and then in step S22 the state of the fatty liver in the subject may be evaluated based on the discriminant value calculated in step S21. Thus, the discriminant values obtained in the multivariate discriminants correlated significantly with the state of the fatty liver can be utilized to bring about the effect of enabling an accurate evaluation of the state of the fatty liver. Specifically, the discrimination between the fatty liver and fatty liver-free in the subject may be conducted based on the discriminant value. Thus, the discriminant values obtained in the multivariate discriminants useful for the 2-group discrimination between the fatty liver and the fatty liver-free can be utilized to bring about the effect of enabling accurately the 2-group discrimination. The multivariate discriminant may be the logistic regression equation containing Ser, Glu, Gly, Ala, Val, and Tyr as the explanatory variables. Thus, the discriminant values obtained in the multivariate discriminants useful particularly for the 2-group discrimination between the fatty liver and the fatty liver-free can be utilized to bring about the effect of enabling more accurately the 2-group discrimination.

In step S21, the discriminant value may be calculated based on both (i) the concentration value of at least one of Gln, Glu, Gly, Ala, Cit, Asn, Trp, Leu, Orn, Phe, Met, Ile, Pro, and ABA contained in the amino acid concentration data and (ii) the multivariate discriminant containing at least one of Gln, Glu, Gly, Ala, Cit, Asn, Trp, Leu, Orn, Phe, Met, Ile, Pro, and ABA as the explanatory variable and then in step S22 the states of the NASH and the NAFLD in the subject may be evaluated based on the discriminant value calculated in step S21. Thus, the discriminant values obtained in the multivariate discriminants correlated significantly with the states of the NASH and the NAFLD can be utilized to bring about the effect of enabling an accurate evaluation of the states of the NASH and the NAFLD. Specifically, the discrimination between the NASH and the "both of the NASH-free and the NAFLD" (the simple steatosis) in the subject may be conducted based on the discriminant value. Thus, the discriminant values obtained in the multivariate discriminants useful for the 2-group discrimination between the NASH and the simple steatosis can be utilized to bring about the effect of enabling accurately the 2-group discrimination. The multivariate discriminant may be the logistic regression equation containing Asn, Gln, Gly, Ala, Cit, and Met as the explanatory variables. Thus, the discriminant values obtained in the multivariate discriminants useful particularly for the 2-group discrimination between the NASH and the simple steatosis can be utilized to bring about the effect of enabling more accurately the 2-group discrimination. Specifically, the discrimination between the NAFLD-free, the NASH, and the "both of the NASH-free and the NAFLD" in the subject may be conducted based on the discriminant value. Thus, the discriminant values obtained in the multivariate discriminants useful for the 3-group discrimination between the NAFLD-free, the NASH, and the simple steatosis can be utilized to bring about the effect of enabling accurately the 3-group discrimination. The multivariate discriminant may be the logistic regression equation containing Ser, Glu, Gly, Val, Tyr, and His as the explanatory variables and the logistic regression equation containing Asn, Gln, Gly, Ala, Cit, and Met as the explanatory variables. Thus, the discriminant values obtained in the multivariate discriminants useful particularly for the 3-group discrimination between the NAFLD-free, the NASH, and the simple steatosis can be utilized to bring about the effect of enabling more accurately the 3-group discrimination.

The multivariate discriminant described above may be prepared by a method described in International Publication WO 2004/052191 that is an international application filed by the present applicant or by a method (multivariate discriminant-preparing processing described later) described in International Publication WO 2006/098192 that is an international application filed by the present applicant. Any multivariate discriminants obtained by these methods can be preferably used in the evaluation of the state of the fatty liver related disease, regardless of the unit of the amino acid concentration in the amino acid concentration data as input data.

The multivariate discriminant refers to a form of equation used generally in multivariate analysis and includes, for example, fractional expression, multiple regression equation, multiple logistic regression equation, linear discriminant function, Mahalanobis' generalized distance, canonical discriminant function, support vector machine, and decision tree. The multivariate discriminant also includes an equation shown by the sum of different forms of multivariate discriminants. In the multiple regression equation, multiple logistic regression equation and canonical discriminant function, a coefficient and constant term are added to each explanatory variable, and the coefficient and constant term in this case are preferably real numbers, more preferably values in the range of 99% confidence interval for the coefficient and constant term obtained from data for discrimination, more preferably in the range of 95% confidence interval for the coefficient and constant term obtained from data for discrimination. The value of each coefficient and the confidence interval thereof may be those multiplied by a real number, and the value of each constant term and the confidence interval thereof may be those having an arbitrary actual constant added or subtracted or those multiplied or divided by an arbitrary actual constant. When an expression such as a logistic regression, a linear discriminant, and a multiple regression analysis is used as an index, a linear transformation of the expression (addition of a constant and multiplication by a constant) and a monotonic increasing (decreasing) transformation (for example, a logit transformation) of the expression do not alter discrimination capability, and thus are equivalent. Therefore, the expression includes an expression that is subjected to a linear transformation and a monotonic increasing (decreasing) transformation.

In the fractional expression, the numerator of the fractional expression is expressed by the sum of the amino acids A, B, C etc. and the denominator of the fractional expression is expressed by the sum of the amino acids a, b, c etc. The fractional expression also includes the sum of the fractional expressions $\alpha$, $\beta$, $\gamma$ etc. (for example, $\alpha+\beta$) having such constitution. The fractional expression also includes divided fractional expressions. The amino acids used in the numerator or denominator may have suitable coefficients respectively. The amino acids used in the numerator or denominator may appear repeatedly. Each fractional expression may have a suitable coefficient. A value of a coefficient for each explanatory variable and a value for a constant term may be any real numbers. In combinations where explanatory variables in the numerator and explanatory variables in the denominator in the fractional expression are switched with each other, the positive (or negative) sign is generally reversed in correlation with objective explanatory variables, but because their correlation is maintained, such combinations can be assumed to be equivalent to one another in discrimination, and thus the fractional expression also includes combinations where explanatory variables in the numerator and explanatory variables in the denominator in the fractional expression are switched with each other.

When the state of the fatty liver related disease is evaluated in the present invention, another biological information (e.g., biological metabolites such as glucose, lipid, protein, peptide, mineral and hormone, and biological indices such as blood glucose level, blood pressure level, sex, age, hepatic disease index, dietary habit, drinking habit, exercise habit, obesity level and disease history) may be used in addition to the amino acid concentration. When the state of the fatty liver related disease is evaluated in the present invention, another biological information (e.g., biological metabolites such as glucose, lipid, protein, peptide, mineral and hormone, and biological indices such as blood glucose level, blood pressure level, sex, age, hepatic disease index, dietary habit, drinking habit, exercise habit, obesity level and disease history) may be used as the explanatory variables in the multivariate discriminant in addition to the amino acid concentration.

Here, the summary of the multivariate discriminant-preparing processing (steps 1 to 4) is described in detail. The processing described below is merely one example, and the method of preparing the multivariate discriminant is not limited thereto.

First, in the present invention, a candidate multivariate discriminant (e.g., $y=a_1x_1+a_2x_2+ \ldots +a_nx_n$, y: fatty liver related disease state index data, $x_i$: amino acid concentration data, $a_i$: constant, i=1, 2, . . . , n) that is a candidate for the multivariate discriminant is prepared in the control device based on a predetermined discriminant-preparing method from fatty liver related disease state information stored in the memory device containing the amino acid concentration data and fatty liver related disease state index data on an index for indicating the state of the fatty liver related disease (step 1). Data containing defective and outliers may be removed in advance from the fatty liver related disease state information.

In step 1, a plurality of the candidate multivariate discriminants may be prepared from the fatty liver related disease state information by using a plurality of the different discriminant-preparing methods (including those for multivariate analysis such as principal component analysis, discriminant analysis, support vector machine, multiple regression analysis, logistic regression analysis, k-means method, cluster analysis, and decision tree). Specifically, a plurality of the candidate multivariate discriminants may be prepared simultaneously and concurrently by using a plurality of different algorithms with the fatty liver related disease state information which is multivariate data composed of the amino acid concentration data and the fatty liver related disease state index data obtained by analyzing blood samples from a large number of healthy groups and fatty liver related disease groups. For example, the two different candidate multivariate discriminants may be formed by performing discriminant analysis and logistic regression analysis simultaneously with the different algorithms. Alternatively, the candidate multivariate discriminant may be formed by converting the fatty liver related disease state information with the candidate multivariate discriminant prepared by performing principal component analysis and then performing discriminant analysis of the converted fatty liver related disease state information. In this way, it is possible to finally prepare the multivariate discriminant suitable for diagnostic condition.

The candidate multivariate discriminant prepared by principal component analysis is a linear expression consisting of amino acid explanatory variables maximizing the variance of all amino acid concentration data. The candidate multivariate discriminant prepared by discriminant analysis is a high-powered expression (including exponential and logarithmic expressions) consisting of amino acid explanatory variables minimizing the ratio of the sum of the variances in respective groups to the variance of all amino acid concentration data. The candidate multivariate discriminant prepared by using support vector machine is a high-powered expression (including kernel function) consisting of amino acid explanatory variables maximizing the boundary between groups. The candidate multivariate discriminant prepared by multiple regression analysis is a high-powered expression consisting of amino acid explanatory variables minimizing the sum of the distances from all amino acid concentration data. The candidate multivariate discriminant prepared by logistic regression analysis is a fraction expression having, as a component, the natural logarithm having a linear expression consisting of amino acid explanatory variables maximizing the likelihood as the exponent. The k-means method is a method of searching k pieces of neighboring amino acid concentration data in various groups, designating the group containing the greatest number of the neighboring points as its data-belonging group, and selecting the amino acid explanatory variable that makes the group to which input amino acid concentration data belong agree well with the designated group. The cluster analysis is a method of clustering (grouping) the points closest in entire amino acid concentration data. The decision tree is a method of ordering amino acid explanatory variables and predicting the group of amino acid concentration data from the pattern possibly held by the higher-ordered amino acid explanatory variable.

Returning to the description of the multivariate discriminant-preparing processing, the candidate multivariate discriminant prepared in step 1 is verified (mutually verified) in the control device based on a particular verifying method (step 2). The verification of the candidate multivariate discriminant is performed on each other to each candidate multivariate discriminant prepared in step 1.

In step 2, at least one of discrimination rate, sensitivity, specificity, information criterion, ROC_AUC (area under the curve in a receiver operating characteristic curve), and the like of the candidate multivariate discriminant may be verified by at least one of the bootstrap method, holdout method, N-fold method, leave-one-out method, and the like. In this way, it is possible to prepare the candidate multivariate discriminant higher in predictability or reliability, by taking the fatty liver related disease state information and the diagnostic condition into consideration.

The discrimination rate is the rate of the fatty liver related disease states judged correct according to the present invention in all input data. The sensitivity is the rate of the fatty liver related disease states judged correct according to the present invention in the fatty liver related disease states declared fatty liver related disease in the input data. The specificity is the rate of the fatty liver related disease states judged correct according to the present invention in the fatty liver related disease states declared healthy in the input data. The information criterion is the sum of the number of the amino acid explanatory variables in the candidate multivariate discriminant prepared in step 1 and the difference in number between the fatty liver related disease states evaluated according to the present invention and those declared in input data. ROC_AUC (area under the curve in a receiver operating characteristic curve) is defined as an area under the curve in a receiver operating characteristic curve (ROC) which is a curve prepared by plotting (x,y)=(1-specificity, sensitivity) on a two-dimensional coordinate, the value of ROC_AUC is equal to 1 for perfect discrimination, and discrimination performance becomes higher as the value becomes closer to 1. The predictability is the average of the discrimination rate, sensitivity, or specificity obtained by repeating verification of the candidate multivariate discriminant. Alternatively, the reliability is the variance of the discrimination rate, sensitivity, or specificity obtained by repeating verification of the candidate multivariate discriminant.

Returning to the description of the multivariate discriminant-preparing processing, a combination of the amino acid concentration data contained in the fatty liver related disease state information used in preparing the candidate multivariate discriminant is selected by selecting the explanatory variable of the candidate multivariate discriminant in the control device based on a predetermined explanatory variable-selecting method from the verification result obtained in step 2 (however, the explanatory variable of the candidate multivariate discriminant may be selected based on the predetermined explanatory variable-selecting method without taking the verification result obtained in step 2 into consideration) (step 3). The selection of the amino acid explanatory variable is performed on each candidate multivariate discriminant prepared in step 1. In this way, it is possible to select the amino acid explanatory variable of the candidate multivariate discriminant properly. The step 1 is executed once again by using the fatty liver related disease state information including the amino acid concentration data selected in step 3.

In step 3, the amino acid explanatory variable of the candidate multivariate discriminant may be selected based on at least one of the stepwise method, best path method, local search method, and genetic algorithm from the verification result obtained in step 2.

The best path method is a method of selecting an amino acid explanatory variable by optimizing an evaluation index of the candidate multivariate discriminant while eliminating the amino acid explanatory variables contained in the candidate multivariate discriminant one by one.

Returning to the description of the multivariate discriminant-preparing processing, the steps 1, 2 and 3 are repeatedly performed in the control device, and based on verification results thus accumulated, the candidate multivariate discriminant used as the multivariate discriminant is selected from a plurality of the candidate multivariate discriminants, thereby preparing the multivariate discriminant (step 4). In the selection of the candidate multivariate discriminant, there are cases where the optimum multivariate discriminant is selected from the candidate multivariate discriminants prepared in the same discriminant-preparing method or the optimum multivariate discriminant is selected from all candidate multivariate discriminants.

As described above, in the multivariate discriminant-preparing processing, the processing for the preparation of the candidate multivariate discriminants, the verification of the candidate multivariate discriminants, and the selection of the explanatory variables in the candidate multivariate discriminants are performed based on the fatty liver related disease state information in a series of operations in a systematized manner, whereby the multivariate discriminant most appropriate for evaluating the state of the fatty liver related disease can be prepared. In other words, in the multivariate discriminant-preparing processing, the amino acid concentration is used in multivariate statistical analysis, and for selecting the optimum and robust combination of the explanatory variables, the explanatory variable-selecting method is combined with cross-validation to extract the multivariate discriminant having high diagnosis performance. Logistic regression equation, linear discriminant, discriminant prepared by support vector machine, discriminant prepared by Mahalanobis' generalized distance method, equation prepared by multiple regression analysis, discriminant prepared by cluster analysis, and the like can be used in the multivariate discriminant.

2-2. System Configuration

Hereinafter, the configuration of the fatty liver related disease-evaluating system according to the second embodiment (hereinafter referred to sometimes as the present system) will be described with reference to FIGS. 4 to 20. This system is merely one example, and the present invention is not limited thereto.

Figure 4:
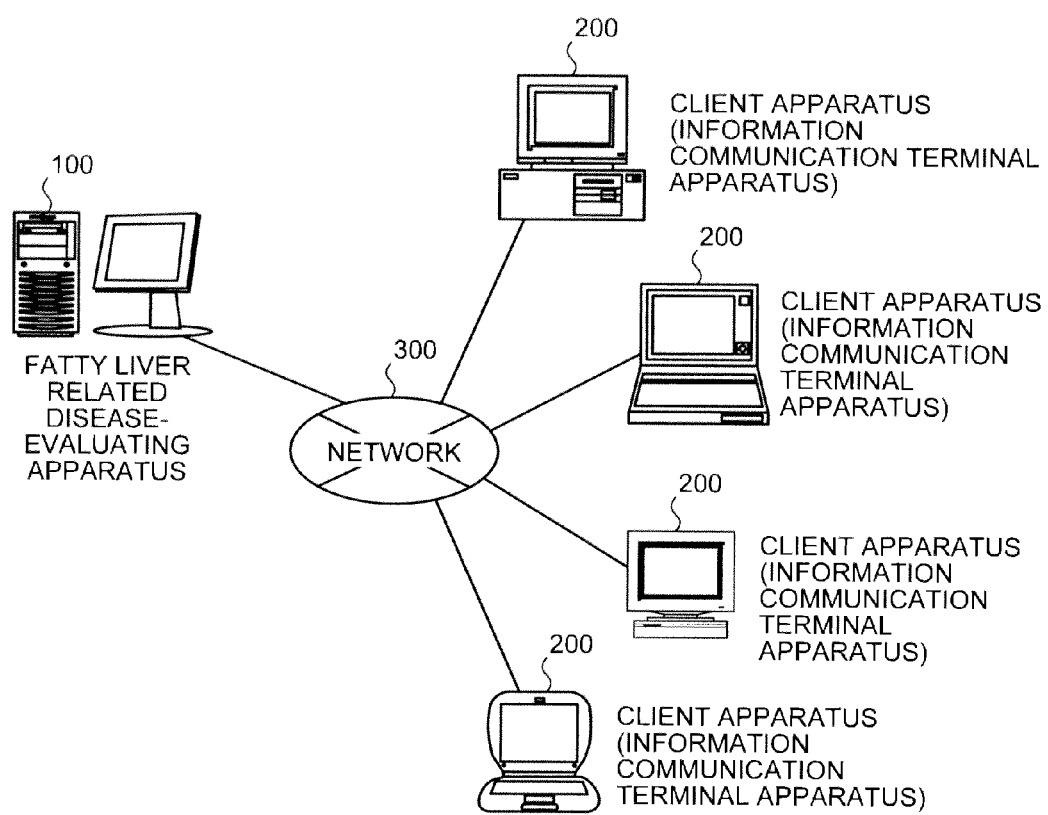
FIG. 4 is a diagram showing an example of an entire configuration of a present system.
Figure 5:
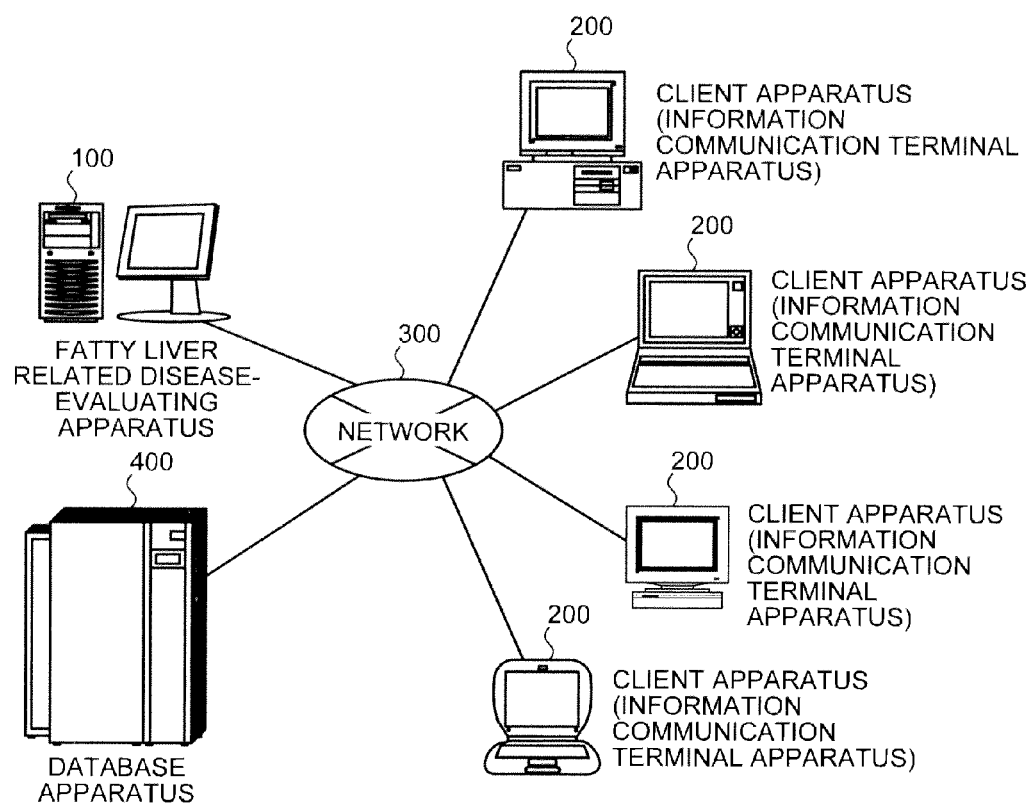
FIG. 5 is a diagram showing another example of an entire configuration of the present system.

First, an entire configuration of the present system will be described with reference to FIGS. 4 and 5. FIG. 4 is a diagram showing an example of the entire configuration of the present system. FIG. 5 is a diagram showing another example of the entire configuration of the present system. As shown in FIG. 4, the present system is constituted in which the fatty liver related disease-evaluating apparatus 100 that evaluates the state of the fatty liver related disease in the subject, and the client apparatus 200 (corresponding to the information communication terminal apparatus of the present invention) that provides the amino acid concentration data of the subject on the concentration values of the amino acids, are communicatively connected to each other via a network 300.

In the present system as shown in FIG. 5, in addition to the fatty liver related disease-evaluating apparatus 100 and the client apparatus 200, the database apparatus 400 storing, for example, the fatty liver related disease state information used in preparing the multivariate discriminant and the multivariate discriminant used in evaluating the state of the fatty liver related disease in the fatty liver related disease-evaluating apparatus 100, may be communicatively connected via the network 300. In this configuration, the information on the state of the fatty liver related disease etc. are provided via the network 300 from the fatty liver related disease-evaluating apparatus 100 to the client apparatuses 200 and the database apparatus 400, or from the client apparatuses 200 and the database apparatus 400 to the fatty liver related disease-evaluating apparatus 100. The "information on the state of the fatty liver related disease" is information on the measured values of particular items of the state of the fatty liver related disease of organisms including human. The information on the state of the fatty liver related disease is generated in the fatty liver related disease-evaluating apparatus 100, client apparatus 200, or other apparatuses (e.g., various measuring apparatuses) and stored mainly in the database apparatus 400.

Figure 6:
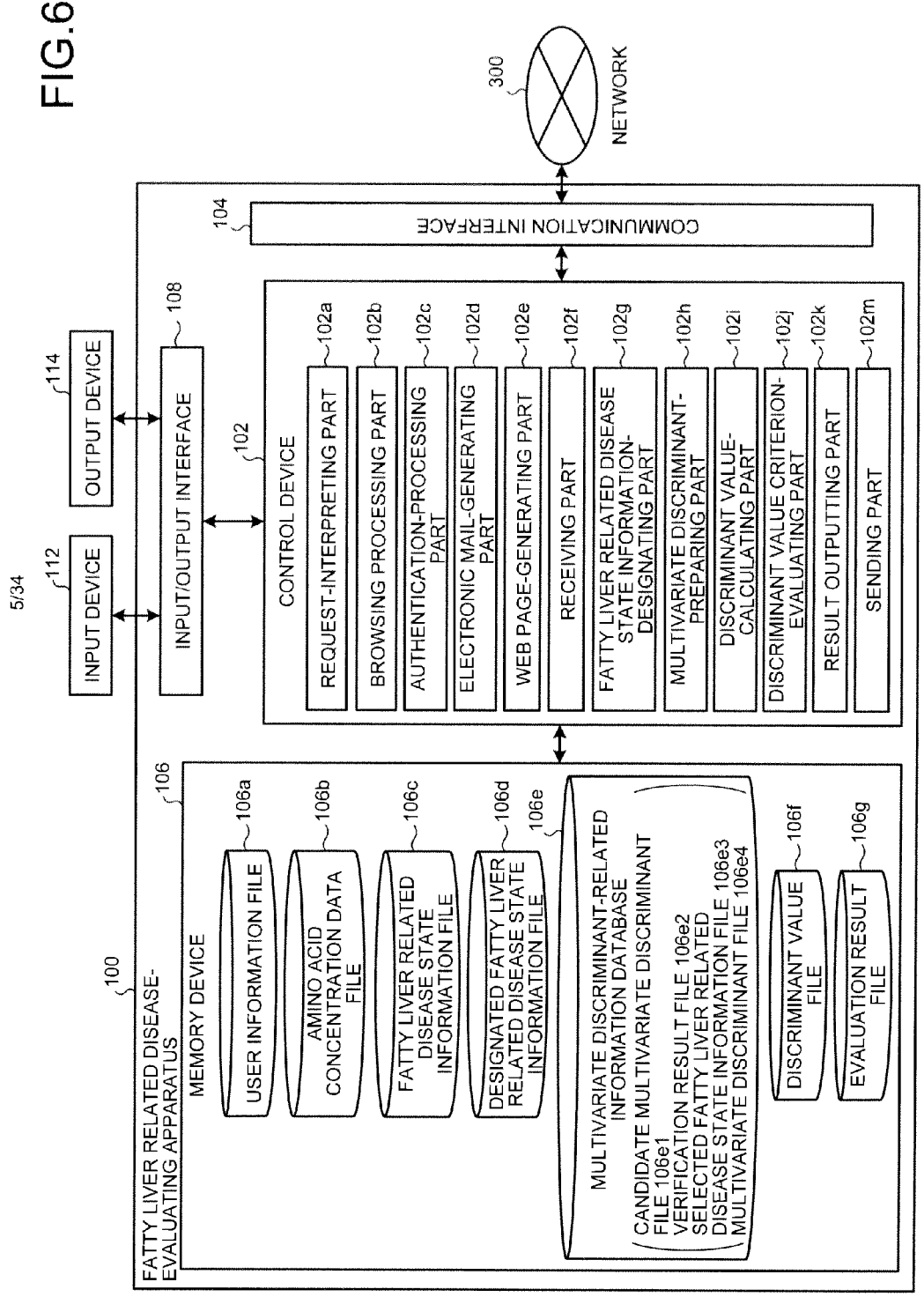
FIG. 6 is a block diagram showing an example of a configuration of a fatty liver related disease-evaluating apparatus 100 in the present system.

Now, the configuration of the fatty liver related disease-evaluating apparatus 100 in the present system will be described with reference to FIGS. 6 to 18. FIG. 6 is a block diagram showing an example of the configuration of the fatty liver related disease-evaluating apparatus 100 in the present system, showing conceptually only the region relevant to the present invention.

The fatty liver related disease-evaluating apparatus 100 includes (I) a control device 102, such as CPU (Central Processing Unit), that integrally controls the fatty liver related disease-evaluating apparatus, (II) a communication interface 104 that connects the fatty liver related disease-evaluating apparatus to the network 300 communicatively via communication apparatuses such as a router and wired or wireless communication lines such as a private line, (III) a memory device 106 that stores various databases, tables, files and others, and (IV) an input/output interface 108 connected to an input device 112 and an output device 114, and these parts are connected to each other communicatively via any communication channel. The fatty liver related disease-evaluating apparatus 100 may be present together with various analyzers (e.g., amino acid analyzer) in a same housing. A typical configuration of disintegration/integration of the fatty liver related disease-evaluating apparatus 100 is not limited to that shown in the figure, and all or a part of it may be disintegrated or integrated functionally or physically in any unit, according to various additions or the like or according to functional loads. In other words, the embodiments may be implemented in arbitrary combinations thereof or an embodiment may be selectively implemented. For example, a part of the processing may be performed via CGI (Common Gateway Interface).

The memory device 106 is a storage means, and examples thereof include memory apparatuses such as RAM (Random Access Memory) and ROM (Read Only Memory), fixed disk drives such as a hard disk, a flexible disk, an optical disk, and the like. The memory device 106 stores computer programs giving instructions to the CPU for various processings, together with OS (Operating System). As shown in the figure, the memory device 106 stores the user information file 106a, the amino acid concentration data file 106b, the fatty liver related disease state information file 106c, the designated fatty liver related disease state information file 106d, a multivariate discriminant-related information database 106e, the discriminant value file 106f, and the evaluation result file 106g.

The user information file 106a stores user information on users. FIG. 7 is a chart showing an example of information stored in the user information file 106a. As shown in FIG. 7, the information stored in the user information file 106a includes user ID (identification) for identifying a user uniquely, user password for authentication of the user, user name, organization ID for uniquely identifying an organization of the user, department ID for uniquely identifying a department of the user organization, department name, and electronic mail address of the user that are correlated to one another.

Returning to FIG. 6, the amino acid concentration data file 106b stores the amino acid concentration data on the concentration values of the amino acids. FIG. 8 is a chart showing an example of information stored in the amino acid concentration data file 106b. As shown in FIG. 8, the information stored in the amino acid concentration data file 106b includes individual number for uniquely identifying an individual (sample) as a subject to be evaluated and amino acid concentration data that are correlated to one another. In FIG. 8, the amino acid concentration data is assumed to be numerical values, i.e., on a continuous scale, but the amino acid concentration data may be expressed on a nominal scale or an ordinal scale. In the case of the nominal or ordinal scale, any number may be allocated to each state for analysis. The amino acid concentration data may be combined with other biological information (e.g., biological metabolites such as glucose, lipid, protein, peptide, mineral and hormone, and biological indices such as blood glucose level, blood pressure level, sex, age, hepatic disease index, dietary habit, drinking habit, exercise habit, obesity level and disease history).

Returning to FIG. 6, the fatty liver related disease state information file 106c stores the fatty liver related disease state information used in preparing the multivariate discriminant. FIG. 9 is a chart showing an example of information stored in the fatty liver related disease state information file 106c. As shown in FIG. 9, the information stored in the fatty liver related disease state information file 106c includes individual (sample) number, fatty liver related disease state index data (T) on index (index $T_1$, index $T_2$, index $T_3$ . . . ) for indicating the state of the fatty liver related disease, and amino acid concentration data that are correlated to one another. In FIG. 9, the fatty liver related disease state index data and the amino acid concentration data are assumed to be numerical values, i.e., on a continuous scale, but the fatty liver related disease state index data and the amino acid concentration data may be expressed on a nominal scale or an ordinal scale. In the case of the nominal or ordinal scale, any number may be allocated to each state for analysis. The fatty liver related disease state index data is a single known condition index serving as a marker of the state of the fatty liver related disease, and numerical data may be used.

Returning to FIG. 6, the designated fatty liver related disease state information file 106d stores the fatty liver related disease state information designated in a fatty liver related disease state information-designating part 102g described below. FIG. 10 is a chart showing an example of information stored in the designated fatty liver related disease state information file 106d. As shown in FIG. 10, the information stored in the designated fatty liver related disease state information file 106d includes individual number, designated fatty liver related disease state index data, and designated amino acid concentration data that are correlated to one another.

Returning to FIG. 6, the multivariate discriminant-related information database 106e is composed of (I) the candidate multivariate discriminant file 106e1 storing the candidate multivariate discriminant prepared in a candidate multivariate discriminant-preparing part 102h1 described below, (II) the verification result file 106e2 storing the verification results obtained in a candidate multivariate discriminant-verifying part 102h2 described below, (III) the selected fatty liver related disease state information file 106e3 storing the fatty liver related disease state information containing the combination of the amino acid concentration data selected in an explanatory variable-selecting part 102h3 described below, and (IV) the multivariate discriminant file 106e4 storing the multivariate discriminant prepared in the multivariate discriminant-preparing part 102h described below.

The candidate multivariate discriminant file 106e1 stores the candidate multivariate discriminants prepared in the candidate multivariate discriminant-preparing part 102h1 described below. FIG. 11 is a chart showing an example of information stored in the candidate multivariate discriminant file 106e1. As shown in FIG. 11, the information stored in the candidate multivariate discriminant file 106e1 includes rank, and candidate multivariate discriminant (e.g., $F_1$ (Gly, Leu, Phe, . . . ), $F_2$ (Gly, Leu, Phe, . . . ), or $F_3$ (Gly, Leu, Phe, . . . ) in FIG. 11) that are correlated to each other.

Returning to FIG. 6, the verification result file 106e2 stores the verification results obtained in the candidate multivariate discriminant-verifying part 102h2 described below. FIG. 12 is a chart showing an example of information stored in the verification result file 106e2. As shown in FIG. 12, the information stored in the verification result file 106e2 includes rank, candidate multivariate discriminant (e.g., $F_k$ (Gly, Leu, Phe, . . . ), $F_m$ (Gly, Leu, Phe, . . . ), $F_l$ (Gly, Leu, Phe, . . . ) in FIG. 12), and verification result of each candidate multivariate discriminant (e.g., evaluation value of each candidate multivariate discriminant) that are correlated to one another.

Returning to FIG. 6, the selected fatty liver related disease state information file 106e3 stores the fatty liver related disease state information including the combination of the amino acid concentration data corresponding to the explanatory variables selected in the explanatory variable-selecting part 102h3 described below. FIG. 13 is a chart showing an example of information stored in the selected fatty liver related disease state information file 106e3. As shown in FIG. 13, the information stored in the selected fatty liver related disease state information file 106e3 includes individual number, fatty liver related disease state index data designated in the fatty liver related disease state information-designating part 102g described below, and amino acid concentration data selected in the explanatory variable-selecting part 102h3 described below that are correlated to one another.

Returning to FIG. 6, the multivariate discriminant file 106e4 stores the multivariate discriminants prepared in the multivariate discriminant-preparing part 102h described below. FIG. 14 is a chart showing an example of information stored in the multivariate discriminant file 106e4. As shown in FIG. 14, the information stored in the multivariate discriminant file 106e4 includes rank, multivariate discriminant (e.g., $F_p$ (Phe, . . . ), $F_p$ (Gly, Leu, Phe), $F_k$ (Gly, Leu, Phe, . . . ) in FIG. 14), a threshold corresponding to each discriminant-preparing method, and verification result of each multivariate discriminant (e.g., evaluation value of each multivariate discriminant) that are correlated to one another.

Returning to FIG. 6, the discriminant value file 106f stores the discriminant value calculated in a discriminant value-calculating part 102i described below. FIG. 15 is a chart showing an example of information stored in the discriminant value file 106f. As shown in FIG. 15, the information stored in the discriminant value file 106f includes individual number for uniquely identifying the individual (sample) as the subject, rank (number for uniquely identifying the multivariate discriminant), and discriminant value that are correlated to one another.

Figures 16, 17:
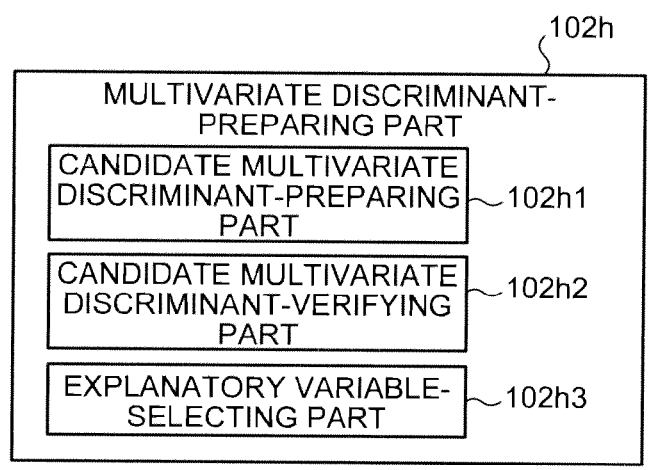
FIG. 16 is a chart showing an example of information stored in an evaluation result file 106g.
FIG. 17 is a block diagram showing a configuration of a multivariable discriminant-preparing part 102h.

Returning to FIG. 6, the evaluation result file 106g stores the evaluation results obtained in the discriminant value criterion-evaluating part 102j described below (specifically the discrimination results obtained in a discriminant value criterion-discriminating part 102*j*1 described below). FIG. 16 is a chart showing an example of information stored in the evaluation result file 106*g*. The information stored in the evaluation result file 106*g* includes individual number for uniquely identifying the individual (sample) as the subject, previously obtained amino acid concentration data of the subject, discriminant value calculated by multivariate discriminant, and evaluation result on the state of the fatty liver related disease, that are correlated to one another.

Returning to FIG. 6, the memory device 106 stores various Web data for providing the client apparatuses 200 with web site information, CGI programs, and others as information other than the information described above. The Web data include data for displaying the Web pages described below and others, and the data are generated as, for example, a HTML (HyperText Markup Language) or XML (Extensible Markup Language) text file. Files for components and files for operation for generation of the Web data, and other temporary files, and the like are also stored in the memory device 106. In addition, the memory device 106 may store as needed sound files of sounds for transmission to the client apparatuses 200 in WAVE format or AIFF (Audio Interchange File Format) format and image files of still images or motion pictures in JPEG (Joint Photographic Experts Group) format or MPEG2 (Moving Picture Experts Group phase 2) format.

The communication interface 104 allows communication between the fatty liver related disease-evaluating apparatus 100 and the network 300 (or communication apparatus such as a router). Thus, the communication interface 104 has a function to communicate data via a communication line with other terminals.

The input/output interface 108 is connected to the input device 112 and the output device 114. A monitor (including a home television), a speaker, or a printer may be used as the output device 114 (hereinafter, the output device 114 may be described as a monitor 114). A keyboard, a mouse, a microphone, or a monitor functioning as a pointing device together with a mouse may be used as the input device 112.

The control device 102 has an internal memory storing control programs such as OS (Operating System), programs for various processing procedures, and other needed data, and performs various information processings according to these programs. As shown in the figure, the control device 102 includes mainly a request-interpreting part 102*a*, a browsing processing part 102*b*, an authentication-processing part 102*c*, an electronic mail-generating part 102*d*, a Web page-generating part 102*e*, a receiving part 102*f*, the fatty liver related disease state information-designating part 102*g*, the multivariate discriminant-preparing part 102*h*, the discriminant value-calculating part 102*i*, the discriminant value criterion-evaluating part 102*j*, a result outputting part 102*k* and a sending part 102*m*. The control device 102 performs data processings such as removal of data including defective, removal of data including many outliers, and removal of explanatory variables for the defective-including data in the fatty liver related disease state information transmitted from the database apparatus 400 and in the amino acid concentration data transmitted from the client apparatus 200.

The request-interpreting part 102*a* interprets the requests transmitted from the client apparatus 200 or the database apparatus 400 and sends the requests to other parts in the control device 102 according to results of interpreting the requests. Upon receiving browsing requests for various screens transmitted from the client apparatus 200, the browsing processing part 102*b* generates and transmits web data for these screens. Upon receiving authentication requests transmitted from the client apparatus 200 or the database apparatus 400, the authentication-processing part 102*c* performs authentication. The electronic mail-generating part 102*d* generates electronic mails including various kinds of information. The Web page-generating part 102*e* generates Web pages for users to browse with the client apparatus 200.

The receiving part 102*f* receives, via the network 300, information (specifically, the amino acid concentration data, the fatty liver related disease state information, the multivariate discriminant etc.) transmitted from the client apparatus 200 and the database apparatus 400. The fatty liver related disease state information-designating part 102*g* designates objective fatty liver related disease state index data and objective amino acid concentration data in preparing the multivariate discriminant.

The multivariate discriminant-preparing part 102*h* generates the multivariate discriminants based on the fatty liver related disease state information received in the receiving part 102*f* and the fatty liver related disease state information designated in the fatty liver related disease state information-designating part 102*g*. Specifically, the multivariate discriminant-preparing part 102*h* generates the multivariate discriminant by selecting the candidate multivariate discriminant used as the multivariate discriminant from a plurality of the candidate multivariate discriminants, based on verification results accumulated by repeating processings in the candidate multivariate discriminant-preparing part 102*h*1, the candidate multivariate discriminant-verifying part 102*h*2, and the explanatory variable-selecting part 102*h*3 from the fatty liver related disease state information.

If the multivariate discriminants are stored previously in a predetermined region of the memory device 106, the multivariate discriminant-preparing part 102*h* may generate the multivariate discriminant by selecting the desired multivariate discriminant out of the memory device 106. Alternatively, the multivariate discriminant-preparing part 102*h* may generate the multivariate discriminant by selecting and downloading the desired multivariate discriminant from the multivariate discriminants previously stored in another computer apparatus (e.g., the database apparatus 400).

Hereinafter, a configuration of the multivariate discriminant-preparing part 102*h* will be described with reference to FIG. 17. FIG. 17 is a block diagram showing the configuration of the multivariate discriminant-preparing part 102*h*, and only a part in the configuration related to the present invention is shown conceptually. The multivariate discriminant-preparing part 102*h* has the candidate multivariate discriminant-preparing part 102*h*1, the candidate multivariate discriminant-verifying part 102*h*2, and the explanatory variable-selecting part 102*h*3, additionally. The candidate multivariate discriminant-preparing part 102*h*1 generates the candidate multivariate discriminant that is a candidate of the multivariate discriminant, from the fatty liver related disease state information based on a predetermined discriminant-preparing method. The candidate multivariate discriminant-preparing part 102*h*1 may generate a plurality of the candidate multivariate discriminants from the fatty liver related disease state information, by using a plurality of the different discriminant-preparing methods. The candidate multivariate discriminant-verifying part 102*h*2 verifies the candidate multivariate discriminant prepared in the candidate multivariate discriminant-preparing part 102*h*1 based on a particular verifying method. The candidate multivariate discriminant-verifying part 102*h*2 may verify at least one of the discrimination rate, sensitivity, specificity, information criterion, and ROC_AUC (area under the curve in a receiver operating characteristic curve) of the candidate multivariate discriminants based on at least one of the bootstrap method, holdout method, N-fold method, and leave-one-out method. The explanatory variable-selecting part 102h3 selects the combination of the amino acid concentration data contained in the fatty liver related disease state information used in preparing the candidate multivariate discriminant, by selecting the explanatory variables of the candidate multivariate discriminant based on a particular explanatory variable-selecting method from the verification results obtained in the candidate multivariate discriminant-verifying part 102h2. The explanatory variable-selecting part 102h3 may select the explanatory variables of the candidate multivariate discriminant based on at least one of the stepwise method, best path method, local search method, and genetic algorithm from the verification results.

Returning to FIG. 6, the discriminant value-calculating part 102i calculates the discriminant value that is the value of the multivariate discriminant, based on the amino acid concentration data of the subject received in the receiving part 102f and the multivariate discriminant prepared in the multivariate discriminant-preparing part 102h. The multivariate discriminant may be any one of a logistic regression equation, a fractional expression, a linear discriminant, a multiple regression equation, a discriminant prepared by a support vector machine, a discriminant prepared by a Mahalanobis' generalized distance method, a discriminant prepared by canonical discriminant analysis, and a discriminant prepared by a decision tree.

Specifically, when evaluating the state of the NASH by the discriminant value criterion-evaluating part 102j (specifically, discriminating between the NASH and the NASH-free by the discriminant value criterion-discriminating part 102j1), the discriminant value-calculating part 102i may calculate the discriminant value based on both (i) the concentration value of at least one of Gln, Glu, Pro, Gly, Ala, Leu, Ile, Val, Tyr, Phe, Met, His, Trp, Thr, Asn, and Ser contained in the amino acid concentration data and (ii) the multivariate discriminant containing at least one of Gln, Glu, Pro, Gly, Ala, Leu, Ile, Val, Tyr, Phe, Met, His, Trp, Thr, Asn, and Ser as the explanatory variable. When discriminating between the NASH and the NASH-free by the discriminant value criterion-discriminating part 102j1, the multivariate discriminant may be the logistic regression equation containing Glu, Gln, Gly, Ala, Val, and Tyr as the explanatory variables.

When evaluating the state of the NAFLD by the discriminant value criterion-evaluating part 102j (specifically, discriminating between the NAFLD and the NAFLD-free by the discriminant value criterion-discriminating part 102j1), the discriminant value-calculating part 102i may calculate the discriminant value based on both (i) the concentration value of at least one of Gln, Glu, Pro, Gly, Ala, Cit, Leu, Ile, Val, Tyr, Phe, Met, His, Trp, Lys, Orn, Ser, Thr, and Asn contained in the amino acid concentration data and (ii) the multivariate discriminant containing at least one of Gln, Glu, Pro, Gly, Ala, Cit, Leu, Ile, Val, Tyr, Phe, Met, His, Trp, Lys, Orn, Ser, Thr, and Asn as the explanatory variable. When discriminating between the NAFLD and the NAFLD-free by the discriminant value criterion-discriminating part 102j1, the multivariate discriminant may be the logistic regression equation containing Ser, Glu, Gly, Val, Tyr, and His as the explanatory variables.

When evaluating the state of the fatty liver by the discriminant value criterion-evaluating part 102j (specifically, discriminating between the fatty liver and the fatty liver-free by the discriminant value criterion-discriminating part 102j1), the discriminant value-calculating part 102i may calculate the discriminant value based on both (i) the concentration value of at least one of Thr, Ser, Glu, Pro, Gly, Ala, Cit, Leu, Ile, Val, Tyr, Phe, Met, His, Trp, Asn, and Orn contained in the amino acid concentration data and (ii) the multivariate discriminant containing at least one of Thr, Ser, Glu, Pro, Gly, Ala, Cit, Leu, Ile, Val, Tyr, Phe, Met, His, Trp, Asn, and Orn as the explanatory variable. When discriminating between the fatty liver and the fatty liver-free by the discriminant value criterion-discriminating part 102j1, the multivariate discriminant may be the logistic regression equation containing Ser, Glu, Gly, Ala, Val, and Tyr as the explanatory variables.

When evaluating the states of the NASH and the NAFLD by the discriminant value criterion-evaluating part 102j (specifically, discriminating between the NASH and the "both of the NASH-free and the NAFLD" (the simple steatosis) or discriminating between the NAFLD-free, the NASH, and the "both of the NASH-free and the NAFLD" by the discriminant value criterion-discriminating part 102j1), the discriminant value-calculating part 102i may calculate the discriminant value based on both (i) the concentration value of at least one of Gln, Glu, Gly, Ala, Cit, Asn, Trp, Leu, Orn, Phe, Met, Ile, Pro, and ABA contained in the amino acid concentration data and (ii) the multivariate discriminant containing at least one of Gln, Glu, Gly, Ala, Cit, Asn, Trp, Leu, Orn, Phe, Met, Ile, Pro, and ABA as the explanatory variable. When discriminating between the NASH and the "both of the NASH-free and the NAFLD" (the simple steatosis) by the discriminant value criterion-discriminating part 102j1, the multivariate discriminant may be the logistic regression equation containing Asn, Gln, Gly, Ala, Cit, and Met as the explanatory variables. When discriminating between the NAFLD-free, the NASH, and the "both of the NASH-free and the NAFLD" by the discriminant value criterion-discriminating part 102j1, the multivariate discriminant may be the logistic regression equation containing Ser, Glu, Gly, Val, Tyr, and His as the explanatory variables and the logistic regression equation containing Asn, Gln, Gly, Ala, Cit, and Met as the explanatory variables.

Figure 18:
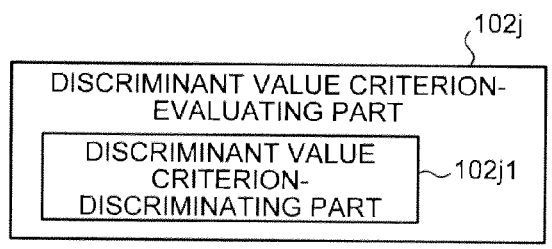
FIG. 18 is a block diagram showing a configuration of a discriminant value criterion-evaluating part 102j.

The discriminant value criterion-evaluating part 102j evaluates the state of the fatty liver related disease (specifically, at least one of the NASH, the NAFLD, and the fatty liver) in the subject based on the discriminant value calculated in the discriminant value-calculating part 102i. The discriminant value criterion-evaluating part 102j further includes the discriminant value criterion-discriminating part 102j1. Now, the configuration of the discriminant value criterion-evaluating part 102j will be described with reference to FIG. 18. FIG. 18 is a block diagram showing the configuration of the discriminant value criterion-evaluating part 102j, and only a part in the configuration related to the present invention is shown conceptually. The discriminant value criterion-discriminating part 102j1 conducts the discrimination between the NASH and the NASH-free, the discrimination between the NAFLD and the NAFLD-free, the discrimination between the fatty liver and the fatty liver-free, the discrimination between the NASH and the "both of the NASH-free and the NAFLD" (the simple steatosis), or the discrimination between the NAFLD-free, the NASH, and the "both of the NASH-free and the NAFLD" in the subject, based on the discriminant value. Specifically, the discriminant value criterion-discriminating part 102j1 compares the discriminant value with a previously established threshold (cutoff value), thereby condicting any one of these discriminations in the subject.

Returning to FIG. 6, the result outputting part 102k outputs, into the output device 114, the processing results in each processing part in the control device 102 (including the evaluation results obtained in the discriminant value criterion-evaluating part 102j (specifically, the discrimination results obtained in the discriminant value criterion-discriminating part 102j1)) etc.

The sending part 102m transmits the evaluation results to the client apparatus 200 that is a sender of the amino acid concentration data of the subject, and transmits the multivariate discriminants prepared in the fatty liver related disease-evaluating apparatus 100 and the evaluation results to the database apparatus 400.

Figure 19:
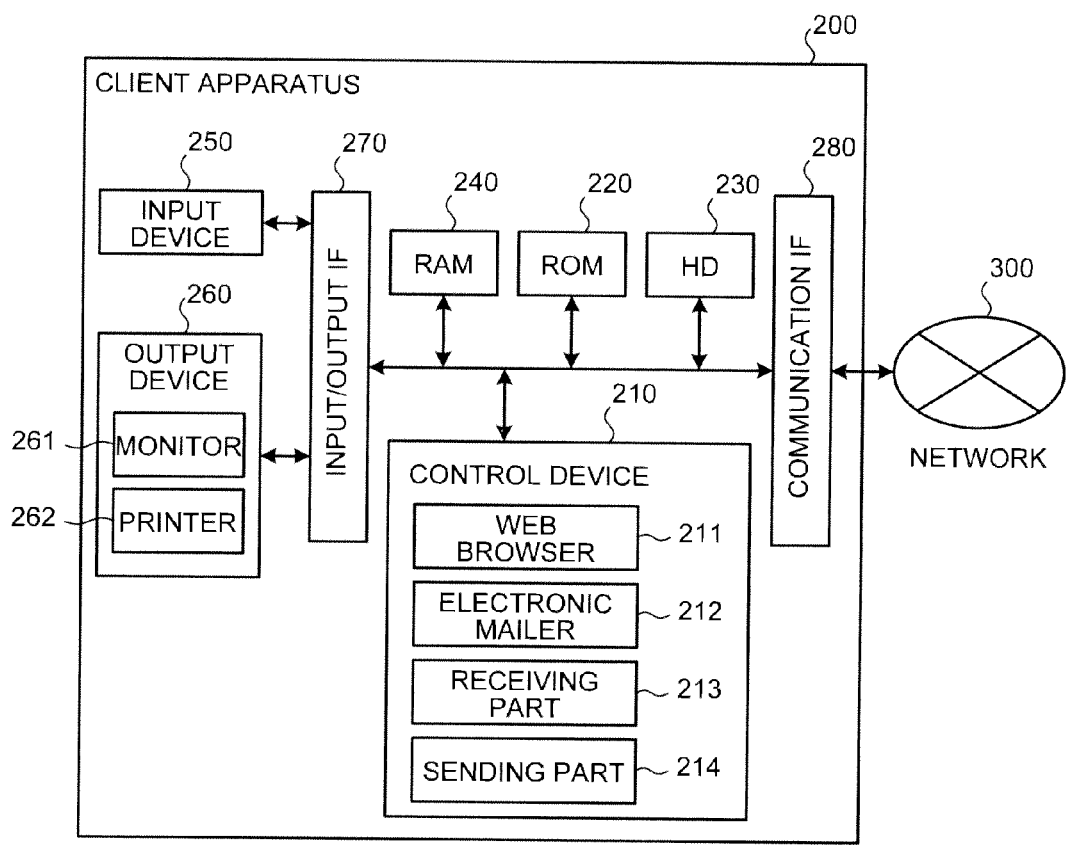
FIG. 19 is a block diagram showing an example of a configuration of a client apparatus 200 in the present system.

Hereinafter, a configuration of the client apparatus 200 in the present system will be described with reference to FIG. 19. FIG. 19 is a block diagram showing an example of the configuration of the client apparatus 200 in the present system, and only the part in the configuration relevant to the present invention is shown conceptually.

The client apparatus 200 includes a control device 210, ROM 220, HD (Hard Disk) 230, RAM 240, an input device 250, an output device 260, an input/output IF 270, and a communication IF 280 that are connected communicatively to one another through a communication channel.

The control device 210 has a Web browser 211, an electronic mailer 212, a receiving part 213, and a sending part 214. The Web browser 211 performs browsing processings of interpreting Web data and displaying the interpreted Web data on a monitor 261 described below. The Web browser 211 may have various plug-in softwares, such as stream player, having functions to receive, display and feedback streaming screen images. The electronic mailer 212 sends and receives electronic mails using a particular protocol (e.g., SMTP (Simple Mail Transfer Protocol) or POPS (Post Office Protocol version 3)). The receiving part 213 receives various kinds of information, such as the evaluation results transmitted from the fatty liver related disease-evaluating apparatus 100, via the communication IF 280. The sending part 214 sends various kinds of information such as the amino acid concentration data of the subject, via the communication IF 280, to the fatty liver related disease-evaluating apparatus 100.

The input device 250 is for example a keyboard, a mouse or a microphone. The monitor 261 described below also functions as a pointing device together with a mouse. The output device 260 is an output means for outputting information received via the communication IF 280, and includes the monitor 261 (including home television) and a printer 262. In addition, the output device 260 may have a speaker or the like additionally. The input/output IF 270 is connected to the input device 250 and the output device 260.

The communication IF 280 connects the client apparatus 200 to the network 300 (or communication apparatus such as a router) communicatively. In other words, the client apparatuses 200 are connected to the network 300 via a communication apparatus such as a modem, TA (Terminal Adapter) or a router, and a telephone line, or a private line. In this way, the client apparatuses 200 can access to the fatty liver related disease-evaluating apparatus 100 by using a particular protocol.

The client apparatus 200 may be realized by installing softwares (including programs, data and others) for a Web data-browsing function and an electronic mail-processing function to an information processing apparatus (for example, an information processing terminal such as a known personal computer, a workstation, a family computer, Internet TV (Television), PHS (Personal Handyphone System) terminal, a mobile phone terminal, a mobile unit communication terminal or PDA (Personal Digital Assistants)) connected as needed with peripheral devices such as a printer, a monitor, and an image scanner.

All or a part of processings of the control device 210 in the client apparatus 200 may be performed by CPU and programs read and executed by the CPU. Computer programs for giving instructions to the CPU and executing various processings together with the OS (Operating System) are recorded in the ROM 220 or HD 230. The computer programs, which are executed as they are loaded in the RAM 240, constitute the control device 210 with the CPU. The computer programs may be stored in application program servers connected via any network to the client apparatus 200, and the client apparatus 200 may download all or a part of them as needed. All or any part of processings of the control device 210 may be realized by hardware such as wired-logic.

Hereinafter, the network 300 in the present system will be described with reference to FIGS. 4 and 5. The network 300 has a function to connect the fatty liver related disease-evaluating apparatus 100, the client apparatuses 200, and the database apparatus 400 mutually, communicatively to one another, and is for example the Internet, an intranet, or LAN (Local Area Network (both wired/wireless)). The network 300 may be VAN (Value Added Network), a personal computer communication network, a public telephone network (including both analog and digital), a leased line network (including both analog and digital), CATV (Community Antenna Television) network, a portable switched network or a portable packet-switched network (including IMT2000 (International Mobile Telecommunication 2000) system, GSM (registered trademark) (Global System for Mobile Communications) system, or PDC (Personal Digital Cellular)/PDC-P system), a wireless calling network, a local wireless network such as Bluetooth (registered trademark), PHS network, a satellite communication network (including CS (Communication Satellite), BS (Broadcasting Satellite), ISDB (Integrated Services Digital Broadcasting), and the like), or the like.

Figure 20:
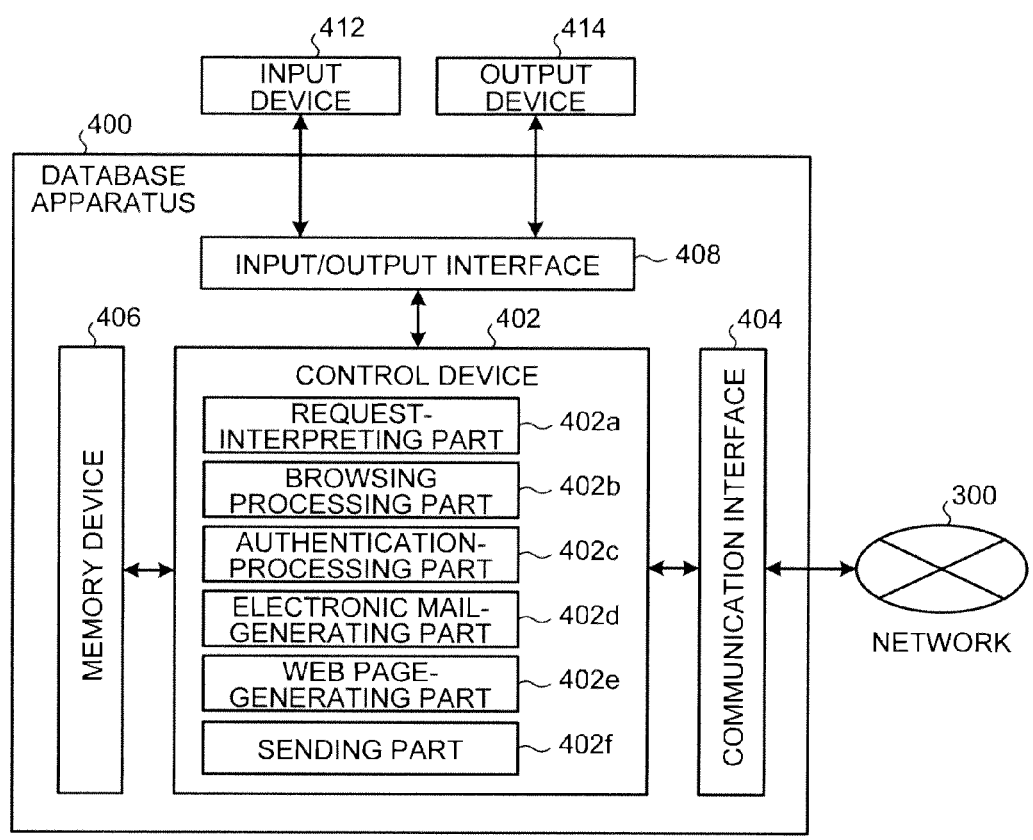
FIG. 20 is a block diagram showing an example of a configuration of a database apparatus 400 in the present system.

Hereinafter, the configuration of the database apparatus 400 in the present system will be described with reference to FIG. 20. FIG. 20 is a block diagram showing an example of the configuration of the database apparatus 400 in the present system, showing conceptually only the region relevant to the present invention.

The database apparatus 400 has functions to store, for example, the fatty liver related disease state information used in preparing the multivariate discriminants in the fatty liver related disease-evaluating apparatus 100 or in the database apparatus 400, the multivariate discriminants prepared in the fatty liver related disease-evaluating apparatus 100, and the evaluation results obtained in the fatty liver related disease-evaluating apparatus 100. As shown in FIG. 20, the database apparatus 400 includes (I) a control device 402, such as CPU, which integrally controls the entire database apparatus, (II) a communication interface 404 connecting the database apparatus to the network 300 communicatively via a communication apparatus such as a router and via wired or wireless communication circuits such as a private line, (III) a memory device 406 storing various databases, tables and files (for example, files for Web pages), and (IV) an input/output interface 408 connected to an input device 412 and an output device 414, and these parts are connected communicatively to each other via any communication channel.

The memory device 406 is a storage means, and may be, for example, memory apparatus such as RAM or ROM, a fixed disk drive such as a hard disk, a flexible disk, an optical disk, and the like. The memory device 406 stores, for example, various programs used in various processings. The communication interface 404 allows communication between the database apparatus 400 and the network 300 (or a communication apparatus such as a router). Thus, the communication interface 404 has a function to communicate data via a communication line with other terminals. The input/output interface 408 is connected to the input device 412 and the output device 414. A monitor (including a home television), a speaker, or a printer may be used as the output device 414 (hereinafter, the output device 414 may be described as a monitor 414). A keyboard, a mouse, a microphone, or a monitor functioning as a pointing device together with a mouse may be used as the input device 412.

The control device 402 has an internal memory storing control programs such as OS (Operating System), programs for various processing procedures, and other needed data, and performs various information processings according to these programs. As shown in the figure, the control device 402 includes mainly a request-interpreting part 402a, a browsing processing part 402b, an authentication-processing part 402c, an electronic mail-generating part 402d, a Web page-generating part 402e, and a sending part 402f.

The request-interpreting part 402a interprets the requests transmitted from the fatty liver related disease-evaluating apparatus 100 and sends the requests to other parts in the control device 402 according to results of interpreting the requests. Upon receiving browsing requests for various screens transmitted from the fatty liver related disease-evaluating apparatus 100, the browsing processing part 402b generates and transmits web data for these screens. Upon receiving authentication requests transmitted from the fatty liver related disease-evaluating apparatus 100, the authentication-processing part 402c performs authentication. The electronic mail-generating part 402d generates electronic mails including various kinds of information. The Web page-generating part 402e generates Web pages for users to browse with the client apparatus 200. The sending part 402f transmits various kinds of information such as the fatty liver related disease state information and the multivariate discriminants to the fatty liver related disease-evaluating apparatus 100.

2-3. Processing in the Present System

Figure 21:
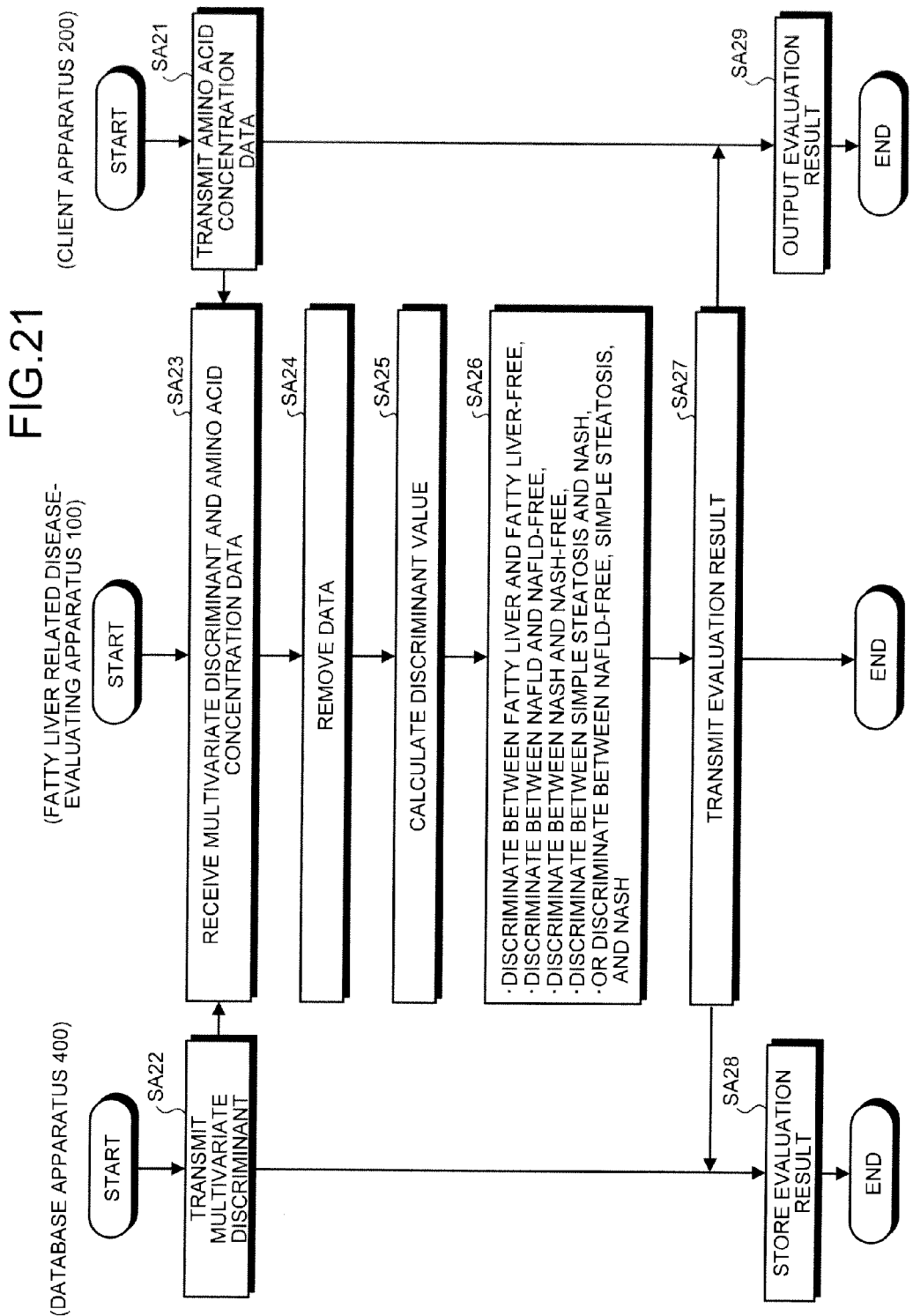
FIG. 21 is a flowchart showing an example of a fatty liver related disease evaluation service processing performed in the present system.

Here, an example of a fatty liver related disease evaluation service processing performed in the present system constituted as described above will be described with reference to FIG. 21. FIG. 21 is a flowchart showing the example of the fatty liver related disease evaluation service processing.

The amino acid concentration data used in the present processing is data concerning the concentration values of amino acids obtained by analyzing, by professionals or ourselves, blood (including, for example, plasma, serum, and the like) previously collected from an individual by a measurement method such as the following (A) or (B). Here, the unit of the amino acid concentration may be, for example, a molar concentration, a weight concentration, or one obtained by addition, subtraction, multiplication, and division of any constant with these concentrations.

(A) Plasma is separated from blood by centrifuging a collected blood sample. All plasma samples are frozen and stored at −80° C. until an amino acid concentration is measured. At the time of measuring an amino acid concentration, acetonitrile is added to perform a protein removal treatment, pre-column derivatization is then performed using a labeled reagent (3-aminopyridyl-N-hydroxysuccinimidyl carbamate), and an amino acid concentration is analyzed by liquid chromatograph mass spectrometer (LC-MS) (see International Publication WO 2003/069328 and International Publication WO 2005/116629).

(B) Plasma is separated from blood by centrifuging a collected blood sample. All plasma samples are frozen and stored at −80° C. until an amino acid concentration is measured. At the time of measuring an amino acid concentration, sulfosalicylic acid is added to perform a protein removal treatment, and an amino acid concentration is analyzed by an amino acid analyzer based on post-column derivatization using a ninhydrin reagent.

First, the client apparatus 200 accesses the fatty liver related disease-evaluating apparatus 100 when the user specifies the Web site address (such as URL) provided from the fatty liver related disease-evaluating apparatus 100, via the input device 250 on the screen displaying the Web browser 211. Specifically, when the user instructs update of the Web browser 211 screen on the client apparatus 200, the Web browser 211 sends the Web site address provided from the fatty liver related disease-evaluating apparatus 100 by a particular protocol to the fatty liver related disease-evaluating apparatus 100, thereby transmitting requests demanding a transmission of Web page corresponding to an amino acid concentration data transmission screen to the fatty liver related disease-evaluating apparatus 100 based on a routing of the address.

Then, upon receipt of the request transmitted from the client apparatus 200, the request-interpreting part 102a in the fatty liver related disease-evaluating apparatus 100 analyzes the transmitted requests and sends the requests to other parts in the control device 102 according to analytical results. Specifically, when the transmitted requests are requests to send the Web page corresponding to the amino acid concentration data transmission screen, mainly the browsing processing part 102b in the fatty liver related disease-evaluating apparatus 100 obtains the Web data for display of the Web page stored in a predetermined region of the memory device 106 and sends the obtained Web data to the client apparatus 200. More specifically, upon receiving the requests to transmit the Web page corresponding to the amino acid concentration data transmission screen by the user, the control device 102 in the fatty liver related disease-evaluating apparatus 100 demands inputs of user ID and user password from the user. If the user ID and password are input, the authentication-processing part 102c in the fatty liver related disease-evaluating apparatus 100 examines the input user ID and password by comparing them with the user ID and user password stored in the user information file 106a for authentication. Only when the user is authenticated, the browsing processing part 102b in the fatty liver related disease-evaluating apparatus 100 sends the Web data for displaying the Web page corresponding to the amino acid concentration data transmission screen to the client apparatus 200. The client apparatus 200 is identified with the IP (Internet Protocol) address transmitted from the client apparatus 200 together with the transmission requests.

Then, the client apparatus 200 receives, in the receiving part 213, the Web data (for displaying the Web page corresponding to the amino acid concentration data transmission screen) transmitted from the fatty liver related disease-evaluating apparatus 100, interprets the received Web data with the Web browser 211, and displays the amino acid concentration data transmission screen on the monitor 261.

When the user inputs and selects, via the input device 250, for example the amino acid concentration data of the individual on the amino acid concentration data transmission screen displayed on the monitor 261, the sending part 214 of the client apparatus 200 transmits an identifier for identifying input information and selected items to the fatty liver related disease-evaluating apparatus 100, thereby transmitting the amino acid concentration data of the individual as the subject to the fatty liver related disease-evaluating apparatus 100 (step SA21). In step SA21, the transmission of the amino acid concentration data may be realized for example by using an existing file transfer technology such as FTP (File Transfer Protocol).

Then, the request-interpreting part 102*a* of the fatty liver related disease-evaluating apparatus 100 interprets the identifier transmitted from the client apparatus 200 thereby interpreting the requests from the client apparatus 200, and requests the database apparatus 400 to send the multivariate discriminant for the evaluation of the state of the fatty liver related disease (specifically, the multivariate discriminant for the 2-group discrimination between the NASH and the NASH-free, the 2-group discrimination between the NAFLD and the NAFLD-free, the 2-group discrimination between the fatty liver and the fatty liver-free, the 2-group discrimination between the NASH and the simple steatosis, or the 3-group discrimination between the NASH, the simple steatosis, and the NAFLD-free).

Then, the request-interpreting part 402*a* in the database apparatus 400 interprets the transmission requests from the fatty liver related disease-evaluating apparatus 100 and transmits, to the fatty liver related disease-evaluating apparatus 100, the multivariate discriminant (for example, the updated newest multivariate discriminant) stored in a predetermined region of the memory device 406 (step SA22).

For example, when discriminating between the NASH and the NASH-free in step SA26, the multivariate discriminant containing at least one of Gln, Glu, Pro, Gly, Ala, Leu, Ile, Val, Tyr, Phe, Met, His, Trp, Thr, Asn, and Ser as the explanatory variable is transmitted to the fatty liver related disease-evaluating apparatus 100 in step SA22. When discriminating between the NAFLD and the NAFLD-free in step SA26, the multivariate discriminant containing at least one of Gln, Glu, Pro, Gly, Ala, Cit, Leu, Ile, Val, Tyr, Phe, Met, His, Trp, Lys, Orn, Ser, Thr, and Asn as the explanatory variable is transmitted to the fatty liver related disease-evaluating apparatus 100 in step SA22. When discriminating between the fatty liver and the fatty liver-free in step SA26, the multivariate discriminant containing at least one of Thr, Ser, Glu, Pro, Gly, Ala, Cit, Leu, Ile, Val, Tyr, Phe, Met, His, Trp, Asn, and Orn as the explanatory variable is transmitted to the fatty liver related disease-evaluating apparatus 100 in step SA22. When discriminating between the NASH and the simple steatosis or discriminating between the NAFLD-free, the NASH, and the simple steatosis in step SA26, the multivariate discriminant containing at least one of Gln, Glu, Gly, Ala, Cit, Asn, Trp, Leu, Orn, Phe, Met, Ile, Pro, and ABA as the explanatory variable is transmitted to the fatty liver related disease-evaluating apparatus 100 in step SA22.

Then, the fatty liver related disease-evaluating apparatus 100 receives, in the receiving part 102*f*, the amino acid concentration data of the individual transmitted from the client apparatuses 200 and the multivariate discriminant transmitted from the database apparatus 400, and stores the received amino acid concentration data in a predetermined memory region of the amino acid concentration data file 106*b* and the received multivariate discriminant in a predetermined memory region of the multivariate discriminant file 106*e*4 (step SA23).

Then, the control device 102 in the fatty liver related disease-evaluating apparatus 100 removes data such as defective and outliers from the amino acid concentration data of the individual received in step SA23 (step SA24).

Then, the fatty liver related disease-evaluating apparatus 100 calculates, in the discriminant value-calculating part 102*i*, the discriminant value based on both (i) the amino acid concentration data of the individual from which the data such as the defective and outliers have been removed in step SA24 and (ii) the multivariate discriminant received in step SA23 (step SA25).

Specifically, when discriminating between the NASH and the NASH-free in step SA26, the fatty liver related disease-evaluating apparatus 100 calculates, in the discriminant value-calculating part 102*i*, the discriminant value based on both (i) the concentration value of at least one of Gln, Glu, Pro, Gly, Ala, Leu, Ile, Val, Tyr, Phe, Met, His, Trp, Thr, Asn, and Ser contained in the amino acid concentration data and (ii) the multivariate discriminant containing at least one of Gln, Glu, Pro, Gly, Ala, Leu, Ile, Val, Tyr, Phe, Met, His, Trp, Thr, Asn, and Ser as the explanatory variable.

When discriminating between the NAFLD and the NAFLD-free in step SA26, the fatty liver related disease-evaluating apparatus 100 calculates, in the discriminant value-calculating part 102*i*, the discriminant value based on both (i) the concentration value of at least one of Gln, Glu, Pro, Gly, Ala, Cit, Leu, Ile, Val, Tyr, Phe, Met, His, Trp, Lys, Orn, Ser, Thr, and Asn contained in the amino acid concentration data and (ii) the multivariate discriminant containing at least one of Gln, Glu, Pro, Gly, Ala, Cit, Leu, Ile, Val, Tyr, Phe, Met, His, Trp, Lys, Orn, Ser, Thr, and Asn as the explanatory variable.

When discriminating between the fatty liver and the fatty liver-free in step SA26, the fatty liver related disease-evaluating apparatus 100 calculates, in the discriminant value-calculating part 102*i*, the discriminant value based on both (i) the concentration value of at least one of Thr, Ser, Glu, Pro, Gly, Ala, Cit, Leu, Ile, Val, Tyr, Phe, Met, His, Trp, Asn, and Orn contained in the amino acid concentration data and (ii) the multivariate discriminant containing at least one of Thr, Ser, Glu, Pro, Gly, Ala, Cit, Leu, Ile, Val, Tyr, Phe, Met, His, Trp, Asn, and Orn as the explanatory variable.

When discriminating between the NASH and the simple steatosis in step SA26 or discriminating between the NAFLD-free, the NASH, and the simple steatosis in step SA26, the fatty liver related disease-evaluating apparatus 100 calculates, in the discriminant value-calculating part 102*i*, the discriminant value based on both (i) the concentration value of at least one of Gln, Glu, Gly, Ala, Cit, Asn, Trp, Leu, Orn, Phe, Met, Ile, Pro, and ABA contained in the amino acid concentration data and (ii) the multivariate discriminant containing at least one of Gln, Glu, Gly, Ala, Cit, Asn, Trp, Leu, Orn, Phe, Met, Ile, Pro, and ABA as the explanatory variable.

Then, the fatty liver related disease-evaluating apparatus 100 (i) compares, in the discriminant value criterion-discriminating part 102*j*1, the discriminant value calculated in step SA25 with a previously established threshold (cutoff value), thereby executing the discrimination between the NASH and the NASH-free, the discrimination between the NAFLD and the NAFLD-free, the discrimination between the fatty liver and the fatty liver-free, the discrimination between the NASH and the simple steatosis (the both of the NASH-free and the NAFLD), or the discrimination between the NAFLD-free, the NASH, and the simple steatosis (the both of the NASH-free and the NAFLD) in the individual, and (ii) stores the discrimination results in a predetermined memory region of the evaluation result file 106g (step SA26).

Then, the sending part 102m in the fatty liver related disease-evaluating apparatus 100 sends, to the client apparatus 200 that has sent the amino acid concentration data and to the database apparatus 400, the discrimination results obtained in step SA26 (step SA27). Specifically, the fatty liver related disease-evaluating apparatus 100 first generates a Web page for displaying the discrimination results in the Web page-generating part 102e and stores the Web data corresponding to the generated Web page in a predetermined memory region of the memory device 106. Then, the user is authenticated as described above by inputting a predetermined URL (Uniform Resource Locator) into the Web browser 211 of the client apparatus 200 via the input device 250, and the client apparatus 200 sends a Web page browsing request to the fatty liver related disease-evaluating apparatus 100. The fatty liver related disease-evaluating apparatus 100 then interprets the browsing request transmitted from the client apparatus 200 in the browsing processing part 102b and reads the Web data corresponding to the Web page for displaying the discrimination results, out of the predetermined memory region of the memory device 106. The sending part 102m in the fatty liver related disease-evaluating apparatus 100 then sends the read-out Web data to the client apparatus 200 and simultaneously sends the Web data or the discrimination results to the database apparatus 400.

In step SA27, the control device 102 in the fatty liver related disease-evaluating apparatus 100 may notify the discrimination results to the user client apparatus 200 by electronic mail. Specifically, the electronic mail-generating part 102d in the fatty liver related disease-evaluating apparatus 100 first acquires the user electronic mail address by referencing the user information stored in the user information file 106a based on the user ID and the like at the transmission timing. The electronic mail-generating part 102d in the fatty liver related disease-evaluating apparatus 100 then generates electronic mail data with the acquired electronic mail address as its mail address, including the user name and the discrimination results. The sending part 102m in the fatty liver related disease-evaluating apparatus 100 then sends the generated electronic mail data to the user client apparatus 200.

Also in step SA27, the fatty liver related disease-evaluating apparatus 100 may send the discrimination results to the user client apparatus 200 by using, for example, an existing file transfer technology such as FTP.

Returning to FIG. 21, the control device 402 in the database apparatus 400 receives the discrimination results or the Web data transmitted from the fatty liver related disease-evaluating apparatus 100 and stores (accumulates) the received discrimination results or the received Web data in a predetermined memory region of the memory device 406 (step SA28).

The receiving part 213 of the client apparatus 200 receives the Web data transmitted from the fatty liver related disease-evaluating apparatus 100, and the received Web data is interpreted with the Web browser 211, to display on the monitor 261 the Web page screen displaying the discrimination results of the individual (step SA29). When the discrimination results are sent from the fatty liver related disease-evaluating apparatus 100 by electronic mail, the electronic mail transmitted from the fatty liver related disease-evaluating apparatus 100 is received at any timing, and the received electronic mail is displayed on the monitor 261 with the known function of the electronic mailer 212 in the client apparatus 200.

In this way, the user can confirm the discrimination results of the individual on the "discrimination between the NASH and the NASH-free", the "discrimination between the NAFLD and the NAFLD-free", the "discrimination between the fatty liver and the fatty liver-free", the "discrimination between the NASH and the simple steatosis", or the "discrimination between the NAFLD-free, the NASH, and the simple steatosis", by browsing the Web page displayed on the monitor 261. The user may print out the content of the Web page displayed on the monitor 261 by the printer 262.

When the discrimination results are transmitted by electronic mail from the fatty liver related disease-evaluating apparatus 100, the user reads the electronic mail displayed on the monitor 261, whereby the user can confirm the discrimination results of the individual on the "discrimination between the NASH and the NASH-free", the "discrimination between the NAFLD and the NAFLD-free", the "discrimination between the fatty liver and the fatty liver-free", the "discrimination between the NASH and the simple steatosis", or the "discrimination between the NAFLD-free, the NASH, and the simple steatosis." The user may print out the content of the electronic mail displayed on the monitor 261 by the printer 262.

Given the foregoing description, the explanation of the fatty liver related disease evaluation service processing is finished.

2-4. Summary of the Second Embodiment and Other Embodiments

According to the fatty liver related disease-evaluating system described above in detail, the client apparatus 200 sends the amino acid concentration data of the individual to the fatty liver related disease-evaluating apparatus 100. Upon receiving the requests from the fatty liver related disease-evaluating apparatus 100, the database apparatus 400 transmits, to the fatty liver related disease-evaluating apparatus 100, the multivariate discriminant for the discrimination between the NASH and the NASH-free, the multivariate discriminant for the discrimination between the NAFLD and the NAFLD-free, the multivariate discriminant for the discrimination between the fatty liver and the fatty liver-free, the multivariate discriminant for the discrimination between the NASH and the simple steatosis, or the multivariate discriminant for the discrimination between the NAFLD-free, the NASH, and the simple steatosis. By the fatty liver related disease-evaluating apparatus 100, (1) the amino acid concentration data is received from the client apparatus 200, and the multivariate discriminant is received from the database apparatus 400 simultaneously, (2) the discriminant value is calculated based on the received amino acid concentration data and the received multivariate discriminant, (3) the calculated discriminant value is compared with the previously established threshold, thereby executing the "discrimination between the NASH and the NASH-free", the "discrimination between the NAFLD and the NAFLD-free", the "discrimination between the fatty liver and the fatty liver-free", the "discrimination between the NASH and the simple steatosis", the "discrimination between the NAFLD-free, the NASH, and the simple steatosis" in the individual, and (4) the discrimination results are transmitted to the client apparatus 200 and database apparatus 400. Then, the client apparatus 200 receives and displays the discrimination results transmitted from the fatty liver related disease-evaluating apparatus 100, and the database apparatus 400 receives and stores the discrimination results transmitted from the fatty liver related disease-evaluating apparatus 100. Thus, the discriminant values obtained in the multivariate discriminants useful for the 2-group discrimination between the NASH and the NASH-free, the 2-group discrimination between the NAFLD and the NAFLD-free, the 2-group discrimination between the fatty liver and the fatty liver-free, the 2-group discrimination between the NASH and the simple steatosis, or the 3-group discrimination between the NAFLD-free, the NASH, and the simple steatosis, can be utilized to bring about the effect of enabling accurately these 2-group discriminations or 3-group discrimination.

According to the fatty liver related disease-evaluating system, the multivariate discriminant used in step SA25 may be any one of the logistic regression equation, the fractional expression, the linear discriminant, the multiple regression equation, the discriminant prepared by the support vector machine, the discriminant prepared by the Mahalanobis' generalized distance method, the discriminant prepared by the canonical discriminant analysis, and the discriminant prepared by the decision tree. Thus, the discriminant values obtained in the multivariate discriminants useful for the 2-group discrimination between the NASH and the NASH-free, the 2-group discrimination between the NAFLD and the NAFLD-free, the 2-group discrimination between the fatty liver and the fatty liver-free, the 2-group discrimination between the NASH and the simple steatosis, or the 3-group discrimination between the NAFLD-free, the NASH, and the simple steatosis, can be utilized to bring about the effect of enabling more accurately these 2-group discriminations or 3-group discrimination.

Specifically, when discriminating between the NASH and the NASH-free in step SA26, the multivariate discriminant used in step SA25 may be the logistic regression equation containing Glu, Gln, Gly, Ala, Val, and Tyr as the explanatory variables. Thus, the discriminant values obtained in the multivariate discriminants useful particularly for the 2-group discrimination between the NASH and the NASH-free can be utilized to bring about the effect of enabling more accurately the 2-group discrimination. When discriminating between the NAFLD and the NAFLD-free in step SA26, the multivariate discriminant used in step SA25 may be the logistic regression equation containing Ser, Glu, Gly, Val, Tyr, and His as the explanatory variables. Thus, the discriminant values obtained in the multivariate discriminants useful particularly for the 2-group discrimination between the NAFLD and the NAFLD-free can be utilized to bring about the effect of enabling more accurately the 2-group discrimination. When discriminating between the fatty liver and the fatty liver-free in step SA26, the multivariate discriminant used in step SA25 may be the logistic regression equation containing Ser, Glu, Gly, Ala, Val, and Tyr as the explanatory variables. Thus, the discriminant values obtained in the multivariate discriminants useful particularly for the 2-group discrimination between the fatty liver and the fatty liver-free can be utilized to bring about the effect of enabling more accurately the 2-group discrimination. When discriminating between the NASH and the simple steatosis in step SA26, the multivariate discriminant used in step SA25 may be the logistic regression equation containing Asn, Gln, Gly, Ala, Cit, and Met as the explanatory variables. Thus, the discriminant values obtained in the multivariate discriminants useful particularly for the 2-group discrimination between the NASH and the simple steatosis can be utilized to bring about the effect of enabling more accurately the 2-group discrimination. When discriminating between the NAFLD-free, the NASH, and the simple steatosis in step SA26, the multivariate discriminant used in step SA25 may be the logistic regression equation containing Ser, Glu, Gly, Val, Tyr, and His as the explanatory variables and the logistic regression equation containing Asn, Gln, Gly, Ala, Cit, and Met as the explanatory variables. Thus, the discriminant values obtained in the multivariate discriminants useful particularly for the 3-group discrimination between the NAFLD-free, the NASH, and the simple steatosis can be utilized to bring about the effect of enabling more accurately the 3-group discrimination.

The multivariate discriminant described above may be prepared by a method described in International Publication WO 2004/052191 that is an international application filed by the present applicant or by a method (multivariate discriminant-preparing processing described later) described in International Publication WO 2006/098192 that is an international application filed by the present applicant. Any multivariate discriminants obtained by these methods can be preferably used in the evaluation of the state of the fatty liver related disease, regardless of the unit of the amino acid concentration in the amino acid concentration data as input data.

In addition to the second embodiment described above, the fatty liver related disease-evaluating apparatus, the fatty liver related disease-evaluating method, the fatty liver related disease-evaluating program product, the recording medium, the fatty liver related disease-evaluating system, and the information communication terminal apparatus according to the present invention can be practiced in various different embodiments within the technological scope of the claims. For example, among the processings described in the second embodiment above, all or a part of the processings described above as performed automatically may be performed manually, and all or a part of the manually conducted processings may be performed automatically by known methods. In addition, the processing procedure, control procedure, specific name, various registered data, information including parameters such as retrieval condition, screen, and database configuration shown in the description above or drawings may be modified arbitrarily, unless specified otherwise. For example, the components of the fatty liver related disease-evaluating apparatus 100 shown in the figures are conceptual and functional and may not be the same physically as those shown in the figure. In addition, all or an arbitrary part of the operational function of each component and each device in the fatty liver related disease-evaluating apparatus 100 (in particular, the operational functions executed in the control device 102) may be executed by the CPU (Central Processing Unit) or the programs executed by the CPU, and may be realized as wired-logic hardware. The fatty liver related disease-evaluating apparatus 100 may be configured as an information processing apparatus such as known personal computer and work station, or may be configured by connecting an arbitrary peripheral device to the information processing apparatus. The fatty liver related disease-evaluating apparatus 100 may be provided by installing software (including the programs and the data, etc.) to cause the information processing apparatus to implement the method according to the present invention.

The "program" is a data processing method written in any language or by any description method and may be of any format such as source code or binary code. The "program" may not be limited to a program configured singly, and may include a program configured decentrally as a plurality of modules or libraries, and a program to achieve the function together with a different program such as OS (Operating System). The program is stored on a non-transitory computer-readable recording medium including programmed instructions for making a computer execute the method according to the present invention and read mechanically as needed by the fatty liver related disease-evaluating apparatus 100. More specifically, computer programs to give instructions to the CPU in cooperation with an OS (operating system) to perform various processes are recorded in the storage unit 106 such as ROM or a HDD (hard disk drive). The computer programs are executed by being loaded to RAM, and form the control unit in cooperation with the CPU. The computer programs may be stored in an application program server connected to the fatty liver related disease-evaluating apparatus 100 via an arbitrary network 300, and all or part thereof can be downloaded as necessary. Any well-known configuration or procedure may be used as specific configuration, reading procedure, installation procedure after reading, and the like for reading the programs recorded on the recording medium in each apparatus.

The "recording media" includes any "portable physical media". Examples of the "portable physical media" include a memory card, a USB (universal serial bus) memory, an SD (secure digital) card, flexible disk, magnetic optical disk, ROM, EPROM (Erasable Programmable Read Only Memory), EEPROM (Electronically Erasable and Programmable Read Only Memory), CD-ROM (Compact Disk Read Only Memory), MO (Magneto-Optical disk), DVD (Digital Versatile Disk), Blu-ray Disc, and the like. The program according to the present invention may be stored in a computer-readable recording medium, or can be configured as a program product.

Figure 22:
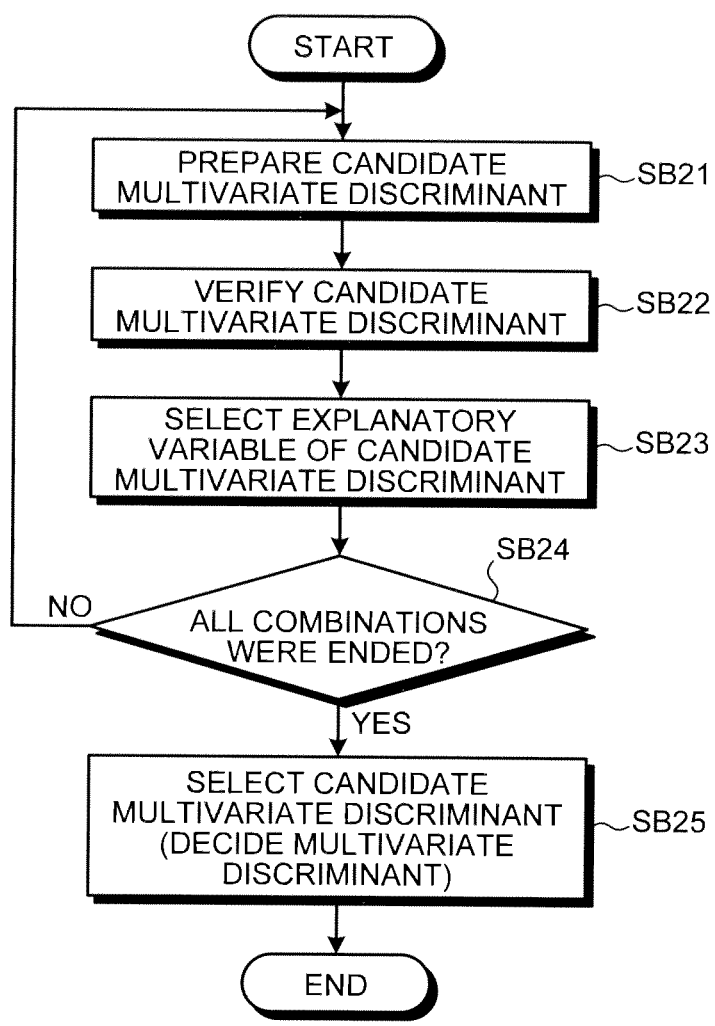
FIG. 22 is a flowchart showing an example of a multivariate discriminant-preparing processing performed in the fatty liver related disease-evaluating apparatus 100 in the present system.

Finally, an example of the multivariate discriminant-preparing processing performed in the fatty liver related disease-evaluating apparatus 100 is described in detail with reference to FIG. 22. The processing described below is merely one example, and the method of preparing the multivariate discriminant is not limited thereto. FIG. 22 is a flowchart showing an example of the multivariate discriminant-preparing processing. The multivariate discriminant-preparing processing may be performed in the database apparatus 400 handling the fatty liver related disease state information.

In the present description, the fatty liver related disease-evaluating apparatus 100 stores the fatty liver related disease state information previously obtained from the database apparatus 400 in a predetermined memory region of the fatty liver related disease state information file 106c. The fatty liver related disease-evaluating apparatus 100 shall store, in a predetermined memory region of the designated fatty liver related disease state information file 106d, the fatty liver related disease state information including the fatty liver related disease state index data and amino acid concentration data designated previously in the fatty liver related disease state information-designating part 102g.

The candidate multivariate discriminant-preparing part 102h1 in the multivariate discriminant-preparing part 102h first prepares the candidate multivariate discriminants according to a predetermined discriminant-preparing method from the fatty liver related disease state information stored in a predetermine memory region of the designated fatty liver related disease state information file 106d, and stores the prepared candidate multivariate discriminants in a predetermined memory region of the candidate multivariate discriminant file 106e1 (step SB21). Specifically, the candidate multivariate discriminant-preparing part 102h1 in the multivariate discriminant-preparing part 102h first selects a desired method out of a plurality of different discriminant-preparing methods (including those for multivariate analysis such as principal component analysis, discriminant analysis, support vector machine, multiple regression analysis, logistic regression analysis, k-means method, cluster analysis, and decision tree) and determines the form of the candidate multivariate discriminant to be prepared (the form of discriminant) based on the selected discriminant-preparing method. The candidate multivariate discriminant-preparing part 102h1 in the multivariate discriminant-preparing part 102h then performs various calculation corresponding to the selected function-selecting method (e.g., average or variance), based on the fatty liver related disease state information. The candidate multivariate discriminant-preparing part 102h1 in the multivariate discriminant-preparing part 102h then determines the parameters for the calculation result and the determined candidate multivariate discriminant. In this way, the candidate multivariate discriminant is generated based on the selected discriminant-preparing method. When the candidate multivariate discriminants are generated simultaneously and concurrently (in parallel) by using a plurality of different discriminant-preparing methods in combination, the processings described above may be executed concurrently for each selected discriminant-preparing method. Alternatively when the candidate multivariate discriminants are generated in series by using a plurality of different discriminant-preparing methods in combination, for example, the candidate multivariate discriminants may be generated by converting the fatty liver related disease state information with the candidate multivariate discriminants prepared by performing principal component analysis and performing discriminant analysis of the converted fatty liver related disease state information.

The candidate multivariate discriminant-verifying part 102h2 in the multivariate discriminant-preparing part 102h verifies (mutually verifies) the candidate multivariate discriminant prepared in step SB21 according to a particular verifying method and stores the verification result in a predetermined memory region of the verification result file 106e2 (step SB22). Specifically, the candidate multivariate discriminant-verifying part 102h2 in the multivariate discriminant-preparing part 102h first generates the verification data to be used in verification of the candidate multivariate discriminant, based on the fatty liver related disease state information stored in a predetermined memory region of the designated fatty liver related disease state information file 106d, and verifies the candidate multivariate discriminant according to the generated verification data. If a plurality of the candidate multivariate discriminants is generated by using a plurality of different discriminant-preparing methods in step SB21, the candidate multivariate discriminant-verifying part 102h2 in the multivariate discriminant-preparing part 102h verifies each candidate multivariate discriminant corresponding to each discriminant-preparing method according to a particular verifying method. Here in step SB22, at least one of the discrimination rate, sensitivity, specificity, information criterion, ROC_AUC (area under the curve in a receiver operating characteristic curve), and the like of the candidate multivariate discriminant may be verified based on at least one method of the bootstrap method, holdout method, N-fold method, leave-one-out method, and the like. Thus, it is possible to select the candidate multivariate discriminant higher in predictability or reliability, by taking the fatty liver related disease state information and diagnostic condition into consideration.

Then, the explanatory variable-selecting part 102h3 in the multivariate discriminant-preparing part 102h selects the combination of the amino acid concentration data contained in the fatty liver related disease state information used in preparing the candidate multivariate discriminant by selecting the explanatory variable of the candidate multivariate discriminant from the verification result obtained in step SB22 according to a predetermined explanatory variable-selecting method (however, the explanatory variable of the candidate multivariate discriminant may be selected based on the predetermined explanatory variable-selecting method without taking the verification result obtained in step SB22 into consideration), and stores the fatty liver related disease state information including the selected combination of the amino acid concentration data in a predetermined memory region of the selected fatty liver related disease state information file 106e3 (step SB23). When a plurality of the candidate multivariate discriminants is generated by using a plurality of different discriminant-preparing methods in step SB21 and each candidate multivariate discriminant corresponding to each discriminant-preparing method is verified according to a predetermined verifying method in step SB22, the explanatory variable-selecting part 102h3 in the multivariate discriminant-preparing part 102h selects the explanatory variable of the candidate multivariate discriminant for each candidate multivariate discriminant (candidate multivariate discriminant corresponding to the verification result obtained in step SB22), according to a predetermined explanatory variable-selecting method in step SB23. Here in step SB23, the explanatory variable of the candidate multivariate discriminant may be selected from the verification results according to at least one of the stepwise method, best path method, local search method, and genetic algorithm. The best path method is a method of selecting an explanatory variable by optimizing an evaluation index of the candidate multivariate discriminant while eliminating the explanatory variables contained in the candidate multivariate discriminant one by one. In step SB23, the explanatory variable-selecting part 102h3 in the multivariate discriminant-preparing part 102h may select the combination of the amino acid concentration data based on the fatty liver related disease state information stored in a predetermined memory region of the designated fatty liver related disease state information file 106d.

The multivariate discriminant-preparing part 102h then judges whether all combinations of the amino acid concentration data contained in the fatty liver related disease state information stored in a predetermined memory region of the designated fatty liver related disease state information file 106d are processed, and if the judgment result is "End" (Yes in step SB24), the processing advances to the next step (step SB25), and if the judgment result is not "End" (No in step SB24), it returns to step SB21. The multivariate discriminant-preparing part 102h may judge whether the processing is performed a predetermined number of times, and if the judgment result is "End" (Yes in step SB24), the processing may advance to the next step (step SB25), and if the judgment result is not "End" (No in step SB24), it may return to step SB21. The multivariate discriminant-preparing part 102h may judge whether the combination of the amino acid concentration data selected in step SB23 is the same as the combination of the amino acid concentration data contained in the fatty liver related disease state information stored in a predetermined memory region of the designated fatty liver related disease state information file 106d or the combination of the amino acid concentration data selected in the previous step SB23, and if the judgment result is "the same" (Yes in step SB24), the processing may advance to the next step (step SB25) and if the judgment result is not "the same" (No in step SB24), it may return to step SB21. If the verification result is specifically the evaluation value for each multivariate discriminant, the multivariate discriminant-preparing part 102h may advance to step SB25 or return to step SB21, based on the comparison of the evaluation value with a particular threshold corresponding to each discriminant-preparing method.

Then, the multivariate discriminant-preparing part 102h determines the multivariate discriminant by selecting the candidate multivariate discriminant used as the multivariate discriminant based on the verification results from a plurality of the candidate multivariate discriminants, and stores the determined multivariate discriminant (the selected candidate multivariate discriminant) in particular memory region of the multivariate discriminant file 106e4 (step SB25). Here, in step SB25, for example, there are cases where the optimal multivariate discriminant is selected from the candidate multivariate discriminants prepared in the same discriminant-preparing method or the optimal multivariate discriminant is selected from all candidate multivariate discriminants.

Given the foregoing description, the explanation of the multivariate discriminant-preparing processing is finished.

Third Embodiment 3-1. Outline of the Invention

Figure 23:
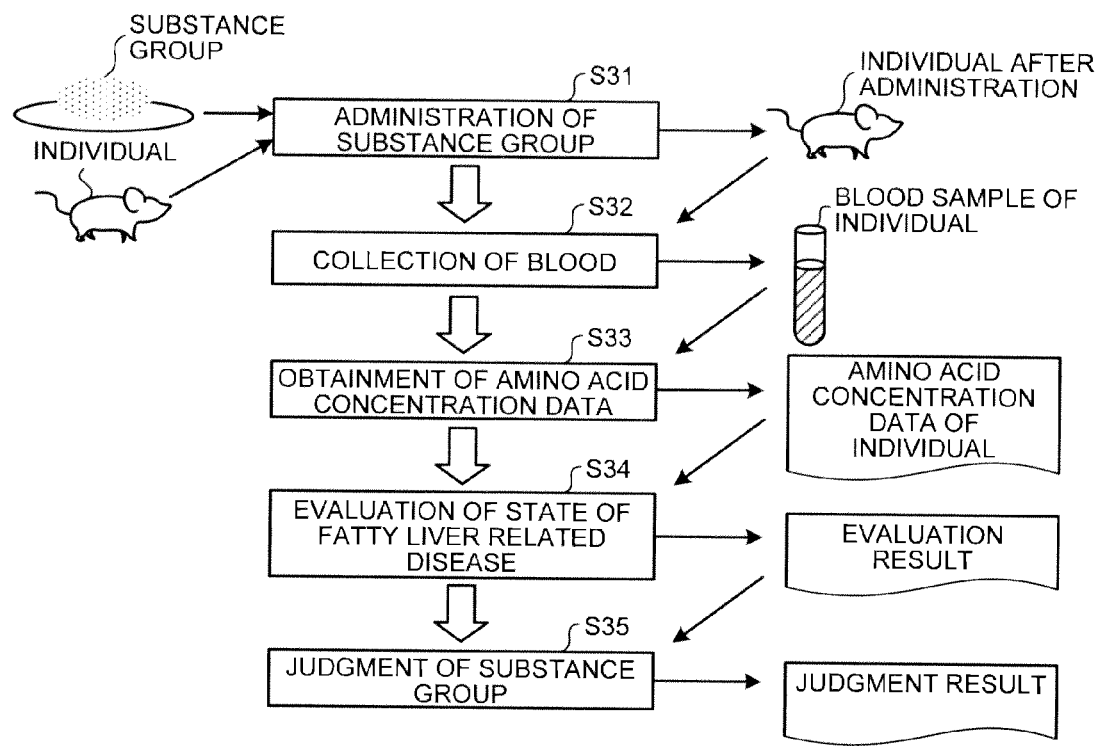
FIG. 23 is a principle configurational diagram showing a basic principle of the present invention.

Herein, the method of searching for prophylactic/ameliorating substance for fatty liver related disease of the present invention is described in detail with reference to FIG. 23. FIG. 23 is a principle configurational diagram showing a basic principle of the present invention.

First, a desired substance group consisting of one or more substances is administered to a subject to be evaluated (for example, an individual such as an animal or a human) (step S31). For example, a suitable combination of an existing drug, amino acid, food and supplement capable of administration to humans (for example, a suitable combination of a drug (for example, insulin resistance improving agents, biguanide agents, ursodeoxycholic acid, antihyperlipemic agents, antioxidants, and the like), supplement, and the like that are known to be effective in amelioration of various symptoms of a fatty liver related disease (specifically, at least one of fatty liver, NAFLD, and NASH)) may be administered over a predetermined period (for example in the range of 1 day to 12 months) in a predetermined amount at predetermined frequency and timing (for example 3 times per day, after food) by a predetermined administration method (for example, oral administration). The administration method, dose, and dosage form may be suitably combined depending on the condition of a patient. The dosage form may be determined based on known techniques. The dose is not particularly limited, and for example, a drug containing 1 μg to 100g active ingredient may be given.

From the subject administered with the substance group in step S31, blood is then collected (step S32).

Amino acid concentration data on a concentration value of an amino acid in the blood collected in step S32 is obtained (step S33). In step S33, for example, the amino acid concentration data determined by a company or the like that performs amino acid concentration measurements may be obtained, or amino acid concentration data may be obtained by determining amino acid concentration data by a measurement method such as, for example, the following method (A) or (B) from blood (including, for example, plasma, serum, and the like) collected from the subject.

Here, the unit of the amino acid concentration may be, for example, a molar concentration, a weight concentration, or one obtained by addition, subtraction, multiplication, and division of any constant with these concentrations.

(A) Plasma is separated from blood by centrifuging a collected blood sample. All plasma samples are frozen and stored at −80° C. until an amino acid concentration is measured. At the time of measuring an amino acid concentration, acetonitrile is added to perform a protein removal treatment, pre-column derivatization is then performed using a labeled reagent (3-aminopyridyl-N-hydroxysuccinimidyl carbamate), and an amino acid concentration is analyzed by liquid chromatograph mass spectrometer (LC-MS) (see International Publication WO 2003/069328 and International Publication WO 2005/116629).

(B) Plasma is separated from blood by centrifuging a collected blood sample. All plasma samples are frozen and stored at −80° C. until an amino acid concentration is measured. At the time of measuring an amino acid concentration, sulfosalicylic acid is added to perform a protein removal treatment, and an amino acid concentration is analyzed by an amino acid analyzer based on post-column derivatization using a ninhydrin reagent.

Then, a state of the fatty liver related disease including at least one of the fatty liver, the NAFLD (non-alcoholic fatty liver disease), and the NASH (non-alcoholic steatohepatitis) in the subject is evaluated based on the amino acid concentration data of the subject obtained in step S33 (step S34).

Then, whether or not the substance group administered in step S31 prevents the fatty liver related disease or ameliorates the state of fatty liver related disease is judged based on an evaluation result in step S34 (step S35).

When a judgment result in step S35 is "preventive or ameliorative", the substance group administered in step S31 is searched as one preventing the fatty liver related disease or ameliorating the state of the fatty liver related disease.

According to the present invention, (I) the desired substance group is administered to the subject, (II) blood is collected from the subject to which the desired substance group has been administered, (III) the amino acid concentration data on the concentration value of the amino acid in the collected blood is obtained, (IV) the state of the fatty liver related disease in the subject is evaluated based on the obtained amino acid concentration data, and (V) whether or not the desired substance group prevents the fatty liver related disease or ameliorates the state of the fatty liver related disease is judged based on the evaluation results. Thus, the method of evaluating fatty liver related disease capable of accurately evaluating the state of the fatty liver related disease by utilizing concentrations of amino acids in blood can be used to bring about an effect of enabling an accurate search for a substance for preventing the fatty liver related disease or ameliorating the state of the fatty liver related disease.

Before step S34 is executed, data such as defective and outliers may be removed from the amino acid concentration data. Thus, the state of the fatty liver related disease can be more accurately evaluated.

In step S34, the state of the NASH in the subject may be evaluated based on the concentration value of at least one of Gln, Glu, Pro, Gly, Ala, Leu, Ile, Val, Tyr, Phe, Met, His, Trp, Thr, Asn, and Ser contained in the amino acid concentration data obtained in step S33. Thus, the concentrations of the amino acids which among amino acids in blood, are correlated with the state of the NASH can be utilized to bring about the effect of enabling an accurate evaluation of the state of the NASH. Specifically, the discrimination between the NASH and NASH-free may be conducted based on the concentration value of at least one of Gln, Glu, Pro, Gly, Ala, Leu, Ile, Val, Tyr, Phe, Met, His, Trp, Thr, Asn, and Ser contained in the amino acid concentration data. Thus, the concentrations of the amino acids which among amino acids in blood, are useful for the 2-group discrimination between the NASH and the NASH-free can be utilized to bring about the effect of enabling accurately the 2-group discrimination.

In step S34, the state of the NAFLD in the subject may be evaluated based on the concentration value of at least one of Gln, Glu, Pro, Gly, Ala, Cit, Leu, Ile, Val, Tyr, Phe, Met, His, Trp, Lys, Orn, Ser, Thr, and Asn contained in the amino acid concentration data obtained in step S33. Thus, the concentrations of the amino acids which among amino acids in blood, are correlated with the state of the NAFLD can be utilized to bring about the effect of enabling an accurate evaluation of the state of the NAFLD. Specifically, the discrimination between the NAFLD and NAFLD-free in the subject may be conducted based on the concentration value of at least one of Gln, Glu, Pro, Gly, Ala, Cit, Leu, Ile, Val, Tyr, Phe, Met, His, Trp, Lys, Orn, Ser, Thr, and Asn contained in the amino acid concentration data. Thus, the concentrations of the amino acids which among amino acids in blood, are useful for the 2-group discrimination between the NAFLD and the NAFLD-free can be utilized to bring about the effect of enabling accurately the 2-group discrimination.

In step S34, the state of the fatty liver in the subject may be evaluated based on the concentration value of at least one of Thr, Ser, Glu, Pro, Gly, Ala, Cit, Leu, Ile, Val, Tyr, Phe, Met, His, Trp, Asn, and Orn contained in the amino acid concentration data obtained in step S33. Thus, the concentrations of the amino acids which among amino acids in blood, are correlated with the state of the fatty liver can be utilized to bring about the effect of enabling an accurate evaluation of the state of the fatty liver. Specifically, the discrimination between the fatty liver and fatty liver-free in the subject may be conducted based on the concentration value of at least one of Thr, Ser, Glu, Pro, Gly, Ala, Cit, Leu, Ile, Val, Tyr, Phe, Met, His, Trp, Asn, and Orn contained in the amino acid concentration data. Thus, the concentrations of the amino acids which among amino acids in blood, are useful for the 2-group discrimination between the fatty liver and the fatty liver-free can be utilized to bring about the effect of enabling accurately the 2-group discrimination.

In step S34, the states of the NASH and the NAFLD in the subject may be evaluated based on the concentration value of at least one of Gln, Glu, Gly, Ala, Cit, Asn, Trp, Leu, Orn, Phe, Met, Ile, Pro, and ABA contained in the amino acid concentration data obtained in step S33. Thus, the concentrations of the amino acids which among amino acids in blood, are correlated with the states of the NASH and the NAFLD can be utilized to bring about the effect of enabling an accurate evaluation of the states of the NASH and the NAFLD. Specifically, the discrimination between the NASH and both of the NASH-free and the NAFLD in the subject may be conducted based on the concentration value of at least one of Gln, Glu, Gly, Ala, Cit, Asn, Trp, Leu, Orn, Phe, Met, Ile, Pro, and ABA contained in the amino acid concentration data. Thus, the concentrations of the amino acids which among amino acids in blood, are useful for the 2-group discrimination between the NASH and the simple steatosis can be utilized to bring about the effect of enabling accurately the 2-group discrimination.

In step S34, a discriminant value that is a value of a multivariate discriminant containing a concentration of the amino acid as an explanatory variable may be calculated based on the amino acid concentration data obtained in step S33 and the previously established multivariate discriminant and then the state of the fatty liver related disease in the subject may be evaluated based on the calculated discriminant value. Thus, the discriminant values obtained in the multivariate discriminants containing the concentration of the amino acid as the explanatory variable can be utilized to bring about the effect of enabling an accurate evaluation of the state of the fatty liver related disease.

The multivariate discriminant may be any one of the logistic regression equation, the fractional expression, the linear discriminant, the multiple regression equation, the discriminant prepared by the support vector machine, the discriminant prepared by the Mahalanobis' generalized distance method, the discriminant prepared by the canonical discriminant analysis, and the discriminant prepared by the decision tree. Thus, the discriminant values obtained in the multivariate discriminants containing the concentration of the amino acid as the explanatory variable can be utilized to bring about the effect of enabling a more accurate evaluation of the state of the fatty liver related disease.

In step S34, the discriminant value may be calculated based on both (i) the concentration value of at least one of Gln, Glu, Pro, Gly, Ala, Leu, Ile, Val, Tyr, Phe, Met, His, Trp, Thr, Asn, and Ser contained in the amino acid concentration data obtained in step S33 and (ii) the multivariate discriminant containing at least one of Gln, Glu, Pro, Gly, Ala, Leu, Ile, Val, Tyr, Phe, Met, His, Trp, Thr, Asn, and Ser as the explanatory variable and then the state of the NASH in the subject may be evaluated based on the calculated discriminant value. Thus, the discriminant values obtained in the multivariate discriminants correlated significantly with the state of the NASH can be utilized to bring about the effect of enabling an accurate evaluation of the state of the NASH. Specifically, the discrimination between the NASH and the NASH-free in the subject may be conducted based on the discriminant value. Thus, the discriminant values obtained in the multivariate discriminants useful for the 2-group discrimination between the NASH and the NASH-free can be utilized to bring about the effect of enabling accurately the 2-group discrimination. The multivariate discriminant may be the logistic regression equation containing Glu, Gln, Gly, Ala, Val, and Tyr as the explanatory variables. Thus, the discriminant values obtained in the multivariate discriminants useful particularly for the 2-group discrimination between the NASH and the NASH-free can be utilized to bring about the effect of enabling more accurately the 2-group discrimination.

In step S34, the discriminant value may be calculated based on both (i) the concentration value of at least one of Gln, Glu, Pro, Gly, Ala, Cit, Leu, Ile, Val, Tyr, Phe, Met, His, Trp, Lys, Orn, Ser, Thr, and Asn contained in the amino acid concentration data obtained in step S33 and (ii) the multivariate discriminant containing at least one of Gln, Glu, Pro, Gly, Ala, Cit, Leu, Ile, Val, Tyr, Phe, Met, His, Trp, Lys, Orn, Ser, Thr, and Asn as the explanatory variable and then the state of the NAFLD in the subject may be evaluated based on the calculated discriminant value. Thus, the discriminant values obtained in the multivariate discriminants correlated significantly with the state of the NAFLD can be utilized to bring about the effect of enabling an accurate evaluation of the state of the NAFLD. Specifically, the discrimination between the NAFLD and the NAFLD-free in the subject may be conducted based on the discriminant value. Thus, the discriminant values obtained in the multivariate discriminants useful for the 2-group discrimination between the NAFLD and the NAFLD-free can be utilized to bring about the effect of enabling accurately the 2-group discrimination. The multivariate discriminant may be the logistic regression equation containing Ser, Glu, Gly, Val, Tyr, and His as the explanatory variables. Thus, the discriminant values obtained in the multivariate discriminants useful particularly for the 2-group discrimination between the NAFLD and the NAFLD-free can be utilized to bring about the effect of enabling more accurately the 2-group discrimination.

In step S34, the discriminant value may be calculated based on both (i) the concentration value of at least one of Thr, Ser, Glu, Pro, Gly, Ala, Cit, Leu, Ile, Val, Tyr, Phe, Met, His, Trp, Asn, and Orn contained in the amino acid concentration data obtained in step S33 and (ii) the multivariate discriminant containing at least one of Thr, Ser, Glu, Pro, Gly, Ala, Cit, Leu, Ile, Val, Tyr, Phe, Met, His, Trp, Asn, and Orn as the explanatory variable and then the state of the fatty liver in the subject may be evaluated based on the calculated discriminant value. Thus, the discriminant values obtained in the multivariate discriminants correlated significantly with the state of the fatty liver can be utilized to bring about the effect of enabling an accurate evaluation of the state of the fatty liver. Specifically, the discrimination between the fatty liver and the fatty liver-free in the subject may be conducted based on the discriminant value. Thus, the discriminant values obtained in the multivariate discriminants useful for the 2-group discrimination between the fatty liver and the fatty liver-free can be utilized to bring about the effect of enabling accurately the 2-group discrimination. The multivariate discriminant may be the logistic regression equation containing Ser, Glu, Gly, Ala, Val, and Tyr as the explanatory variables. Thus, the discriminant values obtained in the multivariate discriminants useful particularly for the 2-group discrimination between the fatty liver and the fatty liver-free can be utilized to bring about the effect of enabling more accurately the 2-group discrimination.

In step S34, the discriminant value may be calculated based on both (i) the concentration value of at least one of Gln, Glu, Gly, Ala, Cit, Asn, Trp, Leu, Orn, Phe, Met, Ile, Pro, and ABA contained in the amino acid concentration data obtained in step S33 and (ii) the multivariate discriminant containing at least one of Gln, Glu, Gly, Ala, Cit, Asn, Trp, Leu, Orn, Phe, Met, Ile, Pro, and ABA as the explanatory variable and then the states of the NASH and the NAFLD in the subject may be evaluated based on the calculated discriminant value. Thus, the discriminant values obtained in the multivariate discriminants correlated significantly with the states of the NASH and the NAFLD can be utilized to bring about the effect of enabling an accurate evaluation of the states of the NASH and the NAFLD. Specifically, the discrimination between the NASH and the "both of the NASH-free and the NAFLD" (the simple steatosis) in the subject may be conducted based on the discriminant value. Thus, the discriminant values obtained in the multivariate discriminants useful for the 2-group discrimination between the NASH and the simple steatosis can be utilized to bring about the effect of enabling accurately the 2-group discrimination. The multivariate discriminant may be the logistic regression equation containing Asn, Gln, Gly, Ala, Cit, and Met as the explanatory variables. Thus, the discriminant values obtained in the multivariate discriminants useful particularly for the 2-group discrimination between the NASH and the simple steatosis can be utilized to bring about the effect of enabling more accurately the 2-group discrimination. Specifically, the discrimination between the NAFLD-free, the NASH, and the "both of the NASH-free and the NAFLD" in the subject may be conducted based on the discriminant value. Thus, the discriminant values obtained in the multivariate discriminants useful for the 3-group discrimination between the NAFLD-free, the NASH, and the simple steatosis can be utilized to bring about the effect of enabling accurately the 3-group discrimination. The multivariate discriminant may be the logistic regression equation containing Ser, Glu, Gly, Val, Tyr, and His as the explanatory variables and the logistic regression equation containing Asn, Gln, Gly, Ala, Cit, and Met as the explanatory variables. Thus, the discriminant values obtained in the multivariate discriminants useful particularly for the 3-group discrimination between the NAFLD-free, the NASH, and the simple steatosis can be utilized to bring about the effect of enabling more accurately the 3-group discrimination.

The multivariate discriminant described above may be prepared by a method described in International Publication WO 2004/052191 that is an international application filed by the present applicant or by a method (multivariate discriminant-preparing processing described in the second embodiment described above) described in International Publication WO 2006/098192 that is an international application filed by the present applicant. Any multivariate discriminants obtained by these methods can be preferably used in the evaluation of the state of the fatty liver related disease, regardless of the unit of the amino acid concentration in the amino acid concentration data as input data.

The multivariate discriminant refers to a form of equation used generally in multivariate analysis and includes, for example, fractional expression, multiple regression equation, multiple logistic regression equation, linear discriminant function, Mahalanobis' generalized distance, canonical discriminant function, support vector machine, and decision tree. The multivariate discriminant also includes an equation shown by the sum of different forms of multivariate discriminants. In the multiple regression equation, multiple logistic regression equation and canonical discriminant function, a coefficient and constant term are added to each explanatory variable, and the coefficient and constant term in this case are preferably real numbers, more preferably values in the range of 99% confidence interval for the coefficient and constant term obtained from data for discrimination, more preferably in the range of 95% confidence interval for the coefficient and constant term obtained from data for discrimination. The value of each coefficient and the confidence interval thereof may be those multiplied by a real number, and the value of each constant term and the confidence interval thereof may be those having an arbitrary actual constant added or subtracted or those multiplied or divided by an arbitrary actual constant. When an expression such as a logistic regression, a linear discriminant, and a multiple regression analysis is used as an index, a linear transformation of the expression (addition of a constant and multiplication by a constant) and a monotonic increasing (decreasing) transformation (for example, a logit transformation) of the expression do not alter discrimination capability, and thus are equivalent. Therefore, the expression includes an expression that is subjected to a linear transformation and a monotonic increasing (decreasing) transformation.

In the fractional expression, the numerator of the fractional expression is expressed by the sum of the amino acids A, B, C etc. and the denominator of the fractional expression is expressed by the sum of the amino acids a, b, c etc. The fractional expression also includes the sum of the fractional expressions α, β, γ etc. (for example, α+β) having such constitution. The fractional expression also includes divided fractional expressions. The amino acids used in the numerator or denominator may have suitable coefficients respectively. The amino acids used in the numerator or denominator may appear repeatedly. Each fractional expression may have a suitable coefficient. A value of a coefficient for each explanatory variable and a value for a constant term may be any real numbers. In combinations where explanatory variables in the numerator and explanatory variables in the denominator in the fractional expression are switched with each other, the positive (or negative) sign is generally reversed in correlation with objective explanatory variables, but because their correlation is maintained, such combinations can be assumed to be equivalent to one another in discrimination, and thus the fractional expression also includes combinations where explanatory variables in the numerator and explanatory variables in the denominator in the fractional expression are switched with each other.

When the state of the fatty liver related disease is evaluated in the present invention, another biological information (e.g., biological metabolites such as glucose, lipid, protein, peptide, mineral and hormone, and biological indices such as blood glucose level, blood pressure level, sex, age, hepatic disease index, dietary habit, drinking habit, exercise habit, obesity level and disease history) may be used in addition to the amino acid concentration. When the state of the fatty liver related disease is evaluated in the present invention, another biological information (e.g., biological metabolites such as glucose, lipid, protein, peptide, mineral and hormone, and biological indices such as blood glucose level, blood pressure level, sex, age, hepatic disease index, dietary habit, drinking habit, exercise habit, obesity level and disease history) may be used as the explanatory variables in the multivariate discriminant in addition to the amino acid concentration.

Figure 24:
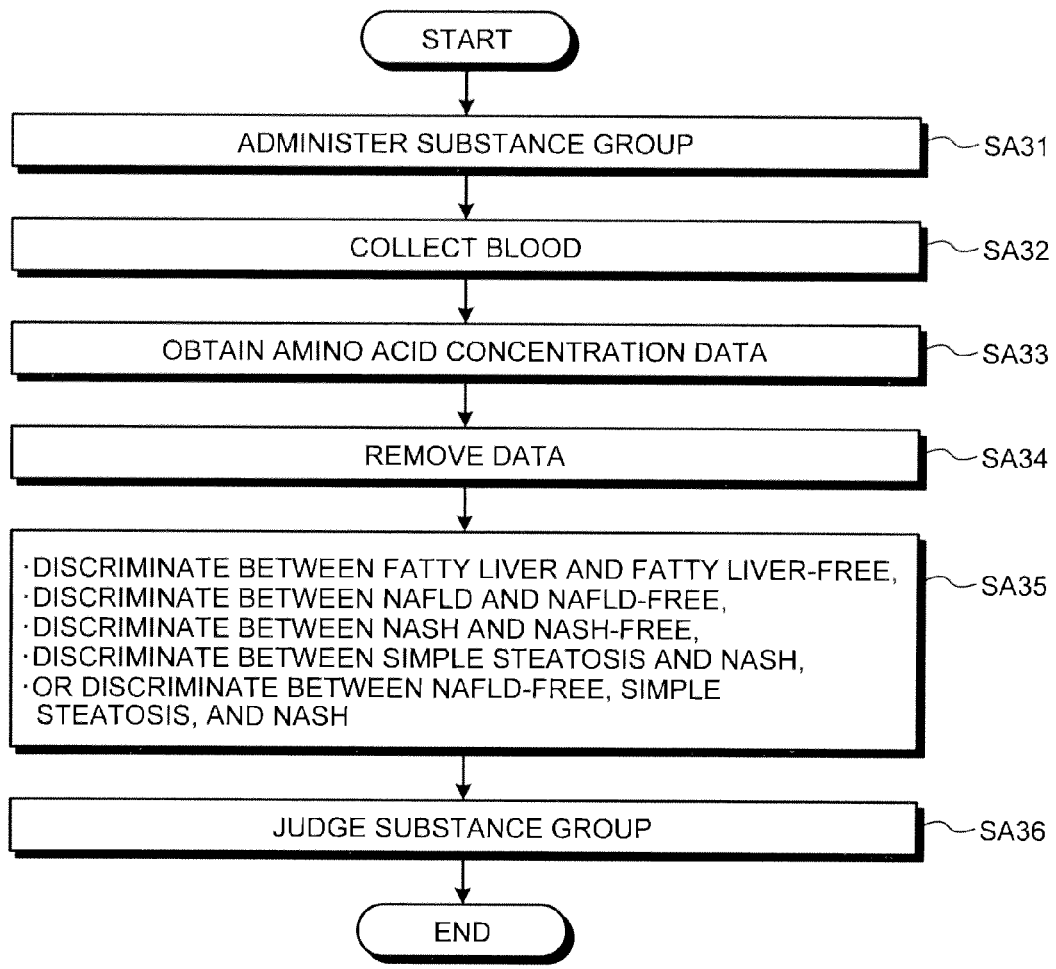
FIG. 24 is a flowchart showing one example of a method of searching for prophylactic/ameliorating substance for fatty liver related disease according to a third embodiment.

3-2. An Example of the Method of Searching for Prophylactic/Ameliorating Substance for Fatty Liver Related Disease According to the Third Embodiment Here, an example of the method of searching for prophylactic/ameliorating substance for fatty liver related disease according to the third embodiment is described with reference to FIG. 24. FIG. 24 is a flowchart showing an example of the method of searching for prophylactic/ameliorating substance for fatty liver related disease according to the third embodiment.

First, a desired substance group consisting of one or more substances is administered to an individual such as an animal or a human with the fatty liver related disease (step SA31).

From the individual administered with the substance group in step SA31, blood is then collected (step SA32).

The amino acid concentration data on the concentration value of the amino acid in the blood collected in step SA32 is obtained (step SA33). In step SA33, for example, the amino acid concentration data determined by a company or the like that performs amino acid concentration measurements may be obtained, or amino acid concentration data may be obtained by determining amino acid concentration data by a measurement method such as, for example, the above described (A) or (B) from blood collected from the subject.

Data such as defective and outliers is then removed from the amino acid concentration data of the individual obtained in step SA33 (step SA34).

Then, any one of the discriminations described in the following 31. to 35. is conducted in the individual, based on the amino acid concentration data of the individual from which the data such as the defective and the outliers have been removed in step SA34 (step SA35).

31. Discrimination Between NASH and NASH-Free (I) the concentration value of at least one of Gln, Glu, Pro, Gly, Ala, Leu, Ile, Val, Tyr, Phe, Met, His, Trp, Thr, Asn, and Ser contained in the amino acid concentration data is compared with a previously established threshold (cutoff value), thereby discriminating between the NASH and the NASH-free in the individual, or (II) the discriminant value is calculated based on both (i) the concentration value of at least one of Gln, Glu, Pro, Gly, Ala, Leu, Ile, Val, Tyr, Phe, Met, His, Trp, Thr, Asn, and Ser contained in the amino acid concentration data and (ii) the multivariate discriminant containing at least one of Gln, Glu, Pro, Gly, Ala, Leu, Ile, Val, Tyr, Phe, Met, His, Trp, Thr, Asn, and Ser as the explanatory variable, and then the calculated discriminant value is compared with a previously established threshold (cutoff value), thereby discriminating between the NASH and the NASH-free in the individual.

32. Discrimination Between NAFLD and NAFLD-Free (I) the concentration value of at least one of Gln, Glu, Pro, Gly, Ala, Cit, Leu, Ile, Val, Tyr, Phe, Met, His, Trp, Lys, Orn, Ser, Thr, and Asn contained in the amino acid concentration data is compared with a previously established threshold (cutoff value), thereby discriminating between the NAFLD and the NAFLD-free in the individual, or (II) the discriminant value is calculated based on both (i) the concentration value of at least one of Gln, Glu, Pro, Gly, Ala, Cit, Leu, Ile, Val, Tyr, Phe, Met, His, Trp, Lys, Orn, Ser, Thr, and Asn contained in the amino acid concentration data and (ii) the multivariate discriminant containing at least one of Gln, Glu, Pro, Gly, Ala, Cit, Leu, Ile, Val, Tyr, Phe, Met, His, Trp, Lys, Orn, Ser, Thr, and Asn as the explanatory variable, and then the calculated discriminant value is compared with a previously established threshold (cutoff value), thereby discriminating between the NAFLD and the NAFLD-free in the individual.

33. Discrimination Between Fatty Liver and Fatty Liver-Free (I) the concentration value of at least one of Thr, Ser, Glu, Pro, Gly, Ala, Cit, Leu, Ile, Val, Tyr, Phe, Met, His, Trp, Asn, and Orn contained in the amino acid concentration data is compared with a previously established threshold (cutoff value), thereby discriminating between the fatty liver and the fatty liver-free in the individual, or (II) the discriminant value is calculated based on both (i) the concentration value of at least one of Thr, Ser, Glu, Pro, Gly, Ala, Cit, Leu, Ile, Val, Tyr, Phe, Met, His, Trp, Asn, and Orn contained in the amino acid concentration data and (ii) the multivariate discriminant containing at least one of Thr, Ser, Glu, Pro, Gly, Ala, Cit, Leu, Ile, Val, Tyr, Phe, Met, His, Trp, Asn, and Orn as the explanatory variable, and then the calculated discriminant value is compared with a previously established threshold (cutoff value), thereby discriminating between the fatty liver and the fatty liver-free in the individual.

34. Discrimination Between NASH and Simple Steatosis (I) the concentration value of at least one of Gln, Glu, Gly, Ala, Cit, Asn, Trp, Leu, Orn, Phe, Met, Ile, Pro, and ABA contained in the amino acid concentration data is compared with a previously established threshold (cutoff value), thereby discriminating between the NASH and the simple steatosis (the both of the NASH-free and the NAFLD) in the individual, or (II) the discriminant value is calculated based on both (i) the concentration value of at least one of Gln, Glu, Gly, Ala, Cit, Asn, Trp, Leu, Orn, Phe, Met, Ile, Pro, and ABA contained in the amino acid concentration data and (ii) the multivariate discriminant containing at least one of Gln, Glu, Gly, Ala, Cit, Asn, Trp, Leu, Orn, Phe, Met, Ile, Pro, and ABA as the explanatory variable, and then the calculated discriminant value is compared with a previously established threshold (cutoff value), thereby discriminating between the NASH and the simple steatosis (the both of the NASH-free and the NAFLD) in the individual.

35. Discrimination Between NASH, Simple Steatosis, and NAFLD-free

The discriminant value is calculated based on both (i) the concentration value of at least one of Gln, Glu, Gly, Ala, Cit, Asn, Trp, Leu, Orn, Phe, Met, Ile, Pro, and ABA contained in the amino acid concentration data and (ii) the multivariate discriminant containing at least one of Gln, Glu, Gly, Ala, Cit, Asn, Trp, Leu, Orn, Phe, Met, Ile, Pro, and ABA as the explanatory variable, and then the calculated discriminant value is compared with a previously established threshold (cutoff value), thereby discriminating between the NAFLD-free, the NASH, and the simple steatosis (the both of the NASH-free and the NAFLD) in the individual.

Whether or not the substance group administered in step SA31 prevents the fatty liver related disease or ameliorates the state of the fatty liver related disease is then judged based on the discrimination results obtained in step SA35 (step SA36).

When the judgment result obtained in step SA36 is "preventive or ameliorative", the substance group administered in step SA31 is searched as one preventing the fatty liver related disease or ameliorating the state of the fatty liver related disease. The substances searched by the searching method include, for example, "amino acid group containing at least one of Gln, Glu, Pro, Gly, Ala, Leu, Ile, Val, Tyr, Phe, Met, His, Trp, Thr, Asn, and Ser", "amino acid group containing at least one of Gln, Glu, Pro, Gly, Ala, Cit, Leu, Ile, Val, Tyr, Phe, Met, His, Trp, Lys, Orn, Ser, Thr, and Asn", "amino acid group containing at least one of Thr, Ser, Glu, Pro, Gly, Ala, Cit, Leu, Ile, Val, Tyr, Phe, Met, His, Trp, Asn, and Orn", and "amino acid group containing at least one of Gln, Glu, Gly, Ala, Cit, Asn, Trp, Leu, Orn, Phe, Met, Ile, Pro, and ABA."

3-3. Summary of the Third Embodiment and Other Embodiments

According to the method of searching for prophylactic/ameliorating substance for fatty liver related disease according to the third embodiment described in detail above, (I) the desired substance group is administered to the individual, (II) blood is collected from the individual administered with the substance group, (III) the amino acid concentration data in the collected blood is obtained, (IV) the data such as the defective and outliers is removed from the obtained amino acid concentration data of the individual, (V) any one of the discriminations 31. to 35. described above is conducted in the individual, based on the amino acid concentration data of the individual from which the data such as the defective and the outliers have been removed, and (VI) whether or not the administered substance group prevents the fatty liver related disease or ameliorates the state of the fatty liver related disease is judged based on the discrimination results. Thus, the method of evaluating fatty liver related disease of the first embodiment described above can be used to bring about an effect of enabling an accurate search for the substance for preventing the fatty liver related disease or ameliorating the state of the fatty liver related disease.

The multivariate discriminant used in step SA35 may be any one of the logistic regression equation, the fractional expression, the linear discriminant, the multiple regression equation, the discriminant prepared by the support vector machine, the discriminant prepared by the Mahalanobis' generalized distance method, the discriminant prepared by the canonical discriminant analysis, and the discriminant prepared by the decision tree. Thus, the discriminant values obtained in the multivariate discriminants useful for the 2-group discrimination between the NASH and the NASH-free, the 2-group discrimination between the NAFLD and the NAFLD-free, the 2-group discrimination between the fatty liver and the fatty liver-free, the 2-group discrimination between the NASH and the simple steatosis, or the 3-group discrimination between the NAFLD-free, the NASH, and the simple steatosis, can be utilized to bring about the effect of enabling more accurately these 2-group discriminations or the 3-group discrimination.

Specifically, the multivariate discriminant used in the above described discrimination 31. may be the logistic regression equation containing Glu, Gln, Gly, Ala, Val, and Tyr as the explanatory variables. Thus, the discriminant values obtained in the multivariate discriminants useful particularly for the 2-group discrimination between the NASH and the NASH-free can be utilized to bring about the effect of enabling more accurately the 2-group discrimination. The multivariate discriminant used in the above described discrimination 32. may be the logistic regression equation containing Ser, Glu, Gly, Val, Tyr, and His as the explanatory variables. Thus, the discriminant values obtained in the multivariate discriminants useful particularly for the 2-group discrimination between the NAFLD and the NAFLD-free can be utilized to bring about the effect of enabling more accurately the 2-group discrimination. The multivariate discriminant used in the above described discrimination 33. may be the logistic regression equation containing Ser, Glu, Gly, Ala, Val, and Tyr as the explanatory variables. Thus, the discriminant values obtained in the multivariate discriminants useful particularly for the 2-group discrimination between the fatty liver and the fatty liver-free can be utilized to bring about the effect of enabling more accurately the 2-group discrimination. The multivariate discriminant used in the above described discrimination 34. may be the logistic regression equation containing Asn, Gln, Gly, Ala, Cit, and Met as the explanatory variables. Thus, the discriminant values obtained in the multivariate discriminants useful particularly for the 2-group discrimination between the NASH and the simple steatosis can be utilized to bring about the effect of enabling more accurately the 2-group discrimination. The multivariate discriminant used in the above described discrimination 35. may be the logistic regression equation containing Ser, Glu, Gly, Val, Tyr, and His as the explanatory variables and the logistic regression equation containing Asn, Gln, Gly, Ala, Cit, and Met as the explanatory variables. Thus, the discriminant values obtained in the multivariate discriminants useful particularly for the 3-group discrimination between the NAFLD-free, the NASH, and the simple steatosis can be utilized to bring about the effect of enabling more accurately the 3-group discrimination.

The multivariate discriminant described above may be prepared by a method described in International Publication WO 2004/052191 that is an international application filed by the present applicant or by a method (multivariate discriminant-preparing processing described in the second embodiment described above) described in International Publication WO 2006/098192 that is an international application filed by the present applicant. Any multivariate discriminants obtained by these methods can be preferably used in the evaluation of the state of the fatty liver related disease, regardless of the unit of the amino acid concentration in the amino acid concentration data as input data.

In the method of searching for prophylactic/ameliorating substance for fatty liver related disease according to the third embodiment, substances that restore normal value to the concentration value of any one of the "amino acid group containing at least one of Gln, Glu, Pro, Gly, Ala, Leu, Ile, Val, Tyr, Phe, Met, His, Trp, Thr, Asn, and Ser", the "amino acid group containing at least one of Gln, Glu, Pro, Gly, Ala, Cit, Leu, Ile, Val, Tyr, Phe, Met, His, Trp, Lys, Orn, Ser, Thr, and Asn", the "amino acid group containing at least one of Thr, Ser, Glu, Pro, Gly, Ala, Cit, Leu, Ile, Val, Tyr, Phe, Met, His, Trp, Asn, and Orn", and the "amino acid group containing at least one of Gln, Glu, Gly, Ala, Cit, Asn, Trp, Leu, Orn, Phe, Met, Ile, Pro, and ABA", or the discriminant value of each multivariate discriminant, can be selected by the method of evaluating fatty liver related disease in the first embodiment described above or by the fatty liver related disease-evaluating apparatus in the second embodiment described above.

In the method of searching for prophylactic/ameliorating substance for fatty liver related disease in the third embodiment, "searching for prophylactic/ameliorating substance" includes not only discovery of a novel substance effective in preventing and ameliorating the fatty liver related disease, but also (i) new discovery of use of a known substance in preventing and ameliorating the fatty liver related disease, (ii) discovery of a novel composition consisting of a combination of existing drugs and supplements having efficacy expectable for prevention and amelioration of the fatty liver related disease, (iii) discovery of the suitable usage, dose and combination described above to form them into a kit, (iv) presentation of a prophylactic and therapeutic menu including a diet, exercise etc., and (v) presentation of a necessary change in menu for each individual by monitoring the effect of the prophylactic and therapeutic menu.

Example 1

When examinees subjected to ultrasonic diagnosis for presence/absence of fatty liver are classified into two groups: a fatty liver negative group and a fatty liver positive group based on the diagnosis result, the fatty liver negative group and the fatty liver positive group include 1021 examinees and 561 examinees, respectively. Amino acid concentrations in plasma collected from examinees are measured, and the fatty liver positive discrimination capability for each amino acid concentration is evaluated with ROC_AUC (area under the curve in a receiver operating characteristic curve). The measurement of an amino acid concentration is performed by the measurement method (A) described in the above embodiment. Amino acids which are significant (p<0.05) in examination with a null hypothesis of ROC_AUC=0.5 under the assumption that ROC_AUC is non-parametric are Thr, Ser, Glu, Pro, Gly, Ala, Cit, Leu, Ile, Val, Tyr, Phe, Met, His, and Trp. Among these amino acids, for Glu, Pro, Ala, Leu, Ile, Val, Tyr, Phe, Met, His, and Trp, a significant increase is shown in the fatty liver positive group, and for Thr, Ser, Gly, and Cit, a significant decrease is shown in the fatty liver positive group.

Example 2

Examinees satisfying the following four diagnosis conditions in diagnosis of non-alcoholic fatty liver disease (NAFLD) are considered as a NAFLD high-risk group, and therefore the examinees are classified as a NAFLD positive group.

Diagnosis condition 1): A diagnosis result of having fatty liver is obtained in ultrasonic diagnosis.

Diagnosis condition 2): The ALT value is high (38 (IU/L) or more).

Diagnosis condition 3): No excessive alcohol intake (everyday intake). (Exception).

Diagnosis condition 4): Not positive for hepatitis virus HBV and HCV. (Exception).

When examinees are classified into two groups: a NAFLD negative group and a NAFLD positive group based on these four diagnosis conditions, the NAFLD negative group and the NAFLD positive group include 1415 examinees and 167 examinees, respectively. Amino acid concentrations in plasma collected from examinees are measured, and the NAFLD positive discrimination capability for each amino acid concentration is evaluated with ROC_AUC. The measurement of an amino acid concentration is performed by the measurement method (A) described in the above embodiment. Amino acids which are significant (p<0.05) in examination with a null hypothesis of ROC_AUC=0.5 under the assumption that ROC_AUC is non-parametric are Gln, Glu, Pro, Gly, Ala, Cit, Leu, Ile, Val, Tyr, Phe, Met, His, Trp, and Lys. Among these amino acids, for Glu, Pro, Ala, Leu, Ile, Val, Tyr, Phe, Met, His, Trp, and Lys, a significant increase is shown in the NAFLD positive group, and for Gln, Gly, and Cit, a significant decrease is shown in the NAFLD positive group.

Example 3

Examinees satisfying five diagnosis conditions: the NAFLD diagnosis conditions 1) to 4) shown in Example 2 plus the following diagnosis condition 5) in diagnosis of non-alcoholic steatohepatitis (NASH) are considered as a NASH high-risk group, and therefore the examinees are classified as a NASH positive group.

Diagnosis condition 5): metabolic syndrome diagnosis conditions (see Document "Metabolic Syndrome Diagnosis Criteria Examination Committee, Journal of Japanese Society of Internal Medicine, 94, 794, 2005") are satisfied.

When examinees are classified into two groups: a NASH negative group and a NASH positive group based on these five diagnosis conditions, the NASH negative group and the NASH positive group include 1518 examinees and 64 examinees, respectively. Amino acid concentrations in plasma collected from examinees are measured, and the NASH positive discrimination capability for each amino acid concentration is evaluated with ROC_AUC. The measurement of an amino acid concentration is performed by the measurement method (A) described in the above embodiment.

Amino acids which are significant (p<0.05) in examination with a null hypothesis of ROC_AUC=0.5 under the assumption that ROC_AUC is non-parametric are Gln, Glu, Pro, Gly, Ala, Leu, Ile, Val, Tyr, Phe, Met, His, and Trp. Among these amino acids, for Glu, Pro, Ala, Leu, Ile, Val, Tyr, Phe, Met, His, and Trp, a significant increase is shown in the NASH positive group, and for Gln and Gly, a significant decrease is shown in the NASH positive group.

Example 4

Amino acid concentration data identical to that determined in Example 1 is used to determine a multivariate discriminant (multivariate function) for discrimination of fatty liver positive, which is effective for the diagnosis of fatty liver described in Example 1 and has an amino acid concentration in plasma as an explanatory variable.

First, a logistic regression equation is used as the multivariate discriminant to explore a combination of explanatory variables to be included in the logistic regression equation, and a Leave-One-Out method is employed as cross validation to extensively explore a logistic regression equation having a good fatty liver positive discrimination capability.

A list of logistic regression equations having equivalently good discrimination capabilities as evaluated with ROC_AUC is shown in FIGS. 25 and 26. Here, FIGS. 25 and 26 show combinations of explanatory variables included in the logistic regression equation, ROC_AUC values with cross validation, and ROC_AUC values without cross validation. When explanatory variables in the formulae included in FIGS. 25 and 26 are listed in the descending order of occurrence frequency from the highest to the tenth, they are arranged in the following order: Glu, Ala, Tyr, Ser, Gly, Val, Leu, Ile, Cit, and His.

Among logistic regression equations having equivalently good discrimination capabilities, for example, the discrimination capability of an index formula "(−4.833)+(−0.017)Ser+(0.0344)Glu+(−0.0057)Gly+(0.0049)Ala+(0.00675)Val+(0.025)Tyr" having a set of explanatory variables "Ser, Glu, Gly, Ala, Val, and Tyr" is good with a ROC_AUC of 0.796, a sensitivity of 0.715, and a specificity of 0.731.

Further, a fractional expression is used as the multivariate discriminant to explore a combination of explanatory variables to be included in the fractional expression, and a bootstrap method is employed as cross validation to extensively explore a fractional expression having a good fatty liver positive discrimination capability.

A list of fractional expressions having equivalently good discrimination capabilities as evaluated with ROC_AUC is shown in FIGS. 27 and 28. Here, FIGS. 27 and 28 show fractional expressions, average values of ROC_AUC values with cross validation, and ROC_AUC values without cross validation. When explanatory variables in the formulae included in FIGS. 27 and 28 are listed in the descending order of occurrence frequency from the highest to the tenth, they are arranged in the following order: Glu, Gly, Ser, Tyr, Cit, Ala, Asn, Orn, Ile and Met.

Example 5

Amino acid concentration data identical to that determined in Example 2 is used to determine a multivariate discriminant (multivariate function) for discrimination of NAFLD positive, which is effective for the diagnosis of NAFLD described in Example 2 and has an amino acid concentration in plasma as an explanatory variable.

First, a logistic regression equation is used as the multivariate discriminant to explore a combination of explanatory variables to be included in the logistic regression equation, and a Leave-One-Out method is employed as cross validation to extensively explore a logistic regression equation having a good NAFLD positive discrimination capability.

A list of logistic regression equations having equivalently good discrimination capabilities as evaluated with ROC_AUC is shown in FIGS. 29 and 30. Here, FIGS. 29 and 30 show combinations of explanatory variables included in the logistic regression equation, ROC_AUC values with cross validation, and ROC_AUC values without cross validation. When explanatory variables in the formulae included in FIGS. 29 and 30 are listed in the descending order of occurrence frequency from the highest to the tenth, they are arranged in the following order: Glu, Tyr, His, Val, Orn, Ile, Ser, Thr, Trp, and Phe.

Among logistic regression equations having equivalently good discrimination capabilities, for example, the discrimination capability of an index formula "(−9.035)+(−0.0121)Ser+(0.0325)Glu+(−0.00565)Gly+(0.0113)Val+(0.0299)Tyr+(0.0271)His" having a set of explanatory variables "Ser, Glu, Gly, Val, Tyr, and His" is good with a ROC_AUC of 0.825, a sensitivity of 0.737, and a specificity of 0.776.

Further, a fractional expression is used as the multivatiate discriminant to explore a combination of explanatory variables to be included in the fractional expression, and a bootstrap method is employed as cross validation to extensively explore a fractional expression having a good NAFLD positive discrimination capability.

A list of fractional expressions having equivalently good discrimination capabilities as evaluated with ROC_AUC is shown in FIGS. 31 and 32. Here, FIGS. 31 and 32 show fractional expressions, average values of ROC_AUC values with cross validation, and ROC_AUC values without cross validation. When explanatory variables in the formulae included in FIGS. 31 and 32 are listed in the descending order of occurrence frequency from the highest to the tenth, they are arranged in the following order: Glu, Tyr, Gly, Cit, Orn, Ser, Asn, His, Met and Ile.

Example 6

Amino acid concentration data identical to that determined in Example 3 is used to determine a multivariate discriminant (multivariate function) for discrimination of NASH positive, which is effective for the diagnosis of NASH described in Example 3 and has an amino acid concentration in plasma as an explanatory variable.

First, a logistic regression equation is used as a multiple variable discrimination formula to explore a combination of explanatory variables to be included in the logistic regression equation, and a Leave-One-Out method was employed as cross validation to extensively explore a logistic regression equation having a good NASH positive discrimination capability.

A list of logistic regression equations having equivalently good discrimination capabilities as evaluated with ROC_AUC is shown in FIGS. 33 and 34. Here, FIGS. 33 and 34 show combinations of explanatory variables included in the logistic regression equation, ROC_AUC values with cross validation, and ROC_AUC values without cross validation. When explanatory variables in the formulae included in FIGS. 33 and 34 are listed in the descending order of occurrence frequency from the highest to the tenth, they are arranged in the following order: Glu, Tyr, Ala, Val, Gln, His, Phe, Thr, Asn, and Ser.

Among logistic regression equations having equivalently good discrimination capabilities, for example, the discrimination capability of an index formula "(−7.443)+(0.0283)Glu+(−0.00648)Gln+(−0.00757)Gly+(0.00468)Ala+(0.0131)Val+(0.0298)Tyr" having a set of explanatory variables "Glu, Gln, Gly, Ala, Val, and Tyr" is good with a ROC_AUC of 0.857, a sensitivity of 0.766, and a specificity of 0.789.

Further, a fractional expression is used as the multivariate discriminant to explore a combination of explanatory variables to be included in the fractional expression, and a bootstrap method is employed as cross validation to extensively explore a fractional expression having a good NASH positive discrimination capability.

A list of fractional expressions having equivalently good discrimination capabilities as evaluated with ROC_AUC is shown in FIGS. 35 and 36. Here, FIGS. 35 and 36 show fractional expressions, average values of ROC_AUC values with cross validation, and ROC_AUC values without cross validation. When explanatory variables in the formulae included in FIGS. 35 and 36 are listed in the descending order of occurrence frequency from the highest to the tenth, they are arranged in the following order: Glu, Gly, Gln, Ala, Tyr, Val, His, Ser, Met, and Thr.

Example 7

When NAFLD positive examinees are classified into two groups: a simple steatosis group and a NASH positive group based on the diagnosis of NAFLD described in Example 2 and the diagnosis of NASH described in Example 3, the simple steatosis group and the NASH positive group include 103 examinees and 64 examinees, respectively. Amino acid concentrations in plasma collected from NAFLD positive examinees are measured, and the NASH positive discrimination capability for each amino acid concentration is evaluated with ROC_AUC. The measurement of an amino acid concentration is performed by the measurement method (A) described in the above embodiment.

Amino acids which are significant ($p<0.05$) in examination with a null hypothesis of ROC_AUC=0.5 under the assumption that ROC_AUC is non-parametric are Gln, Glu, Gly, and Ala. Among these amino acids, for Glu and Ala, a significant increase is shown in the NASH positive group, and for Gln and Gly, a significant decrease is shown in the NASH positive group.

Amino acid concentration data identical to that determined this Example is used to determine a multivariate discriminant (multivariate function) for discrimination of NASH positive, which has an amino acid concentration in plasma as an explanatory variable.

First, a logistic regression equation is used as a multiple function to explore a combination of explanatory variables to be included in the logistic regression equation, and a Leave-One-Out method is employed as cross validation to extensively explore a logistic regression equation having a good NASH positive discrimination capability.

A list of logistic regression equations having equivalently good discrimination capabilities as evaluated with ROC_AUC is shown in FIGS. 37 and 38. Here, FIGS. 37 and 38 show combinations of explanatory variables included in the logistic regression equation, ROC_AUC values with cross validation, and ROC_AUC values without cross validation. When explanatory variables in the formulae included in FIGS. 37 and 38 are listed in the descending order of occurrence frequency from the highest to the tenth, they are arranged in the following order: Ala, Cit, Gln, Asn, Trp, Leu, Orn, Phe, Met, and Ile.

Among logistic regression equations having equivalently good discrimination capabilities, for example, the discrimination capability of an index formula "(1.989)+(−0.0708)Asn+(−0.0104)Gln+(−0.00473)Gly+(0.00649)Ala+(0.0776)Cit+(0.0768)Met" having a set of explanatory variables "Asn, Gln, Gly, Ala, Cit, and Met" is good with a ROC_AUC of 0.753, a sensitivity of 0.688, and a specificity of 0.718.

Further, a fractional expression is used as the multivariate discriminant to explore a combination of explanatory variables to be included in the fractional expression, and a bootstrap method is employed as cross validation to extensively explore a fractional expression having a good NASH positive discrimination capability.

A list of fractional expressions having equivalently good discrimination capabilities as evaluated with ROC_AUC is shown in FIGS. 39 and 40. Here, FIGS. 39 and 40 show fractional expressions, average values of ROC_AUC values with cross validation, and ROC_AUC values without cross validation. When explanatory variables in the formulae included in FIGS. 39 and 40 are listed in the descending order of occurrence frequency from the highest to the tenth, they are arranged in the following order: Cit, Gln, Ala, Asn, Leu, Pro, Trp, Met, Glu, and ABA (aminobutyric acid).

Example 8

When all examinees are classified into three groups: a NAFLD negative (normal) group, a simple steatosis group, and a NASH positive group based on the diagnosis of NAFLD described in Example 2 and the diagnosis of NASH described in Example 3, the normal group, the simple steatosis group, and the NASH positive group include 1415 examinees, 103 examinees, and 64 examinees, respectively. Amino acid concentrations in plasma collected from the examinees are measured, and using a multivariate discriminant containing each amino acid as an explanatory variable, discrimination between the normal and the NAFLD positive is first performed for all examinees, and discrimination between the simple steatosis and the NASH positive is then performed for the group discriminated as NAFLD positive, thereby performing discrimination of three groups: the normal group, the simple steatosis group, and the NASH positive group in two stages as a whole. The measurement of an amino acid concentration is performed by the measurement method (A) described in the above embodiment. The multivariate function formula "(−9.035)+(−0.0121)Ser+ (0.0325)Glu+(−0.00565)Gly+(0.0113)Val+(0.0299)Tyr+ (0.0271)His" described in Example 5 is used in the first discrimination between the normal and the NAFLD positive, and then the multivariate function formula "(1.989)+ (−0.0708)Asn+(−0.0104)Gln+(−0.00473)Gly+(0.00649) Ala+(0.0776)Cit+(0.0768)Met" described in Example 7 is used in the discrimination between the simple steatosis and the NASH positive for the group discriminated as NAFLD positive.

Figures 41, 42:
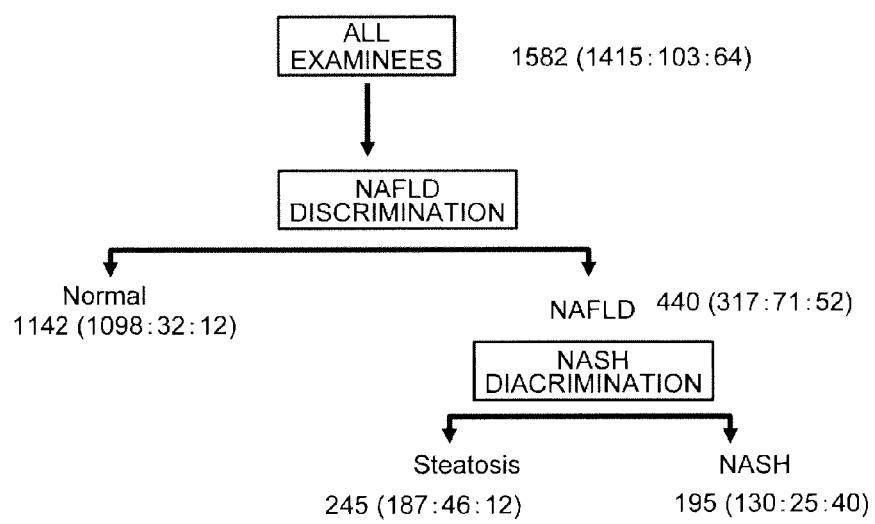
FIG. 41 is a chart showing the discrimination result of a discrimination between the NAFLD negative, the simple steatosis, and the NASH positive.
FIG. 42 is a chart showing the discrimination result of the discrimination between the NAFLD negative, the simple steatosis, and the NASH positive.

Results of discrimination of three groups: the normal group, the simple steatosis group, and the NASH positive group in two stages are shown in FIG. 41 (the normal is described as Normal and simple steatosis is described as Steatosis in the figure). Four sets of numbers in the figure represent the total number (the number of individuals in three groups: normal, simple steatosis, and NASH positive) in each discrimination prediction result.

For results of discrimination of three groups: the normal group, the simple steatosis group, and the NASH positive group in two stages, the prevalence (Prev), the sensitivity (Sen), the positive predictive value (PPV), and the concentration factor of prediction (PPV/Prev) are shown in FIG. 42 (the normal is described as Normal and simple steatosis is described as Steatosis in the figure).

In discrimination of three groups: the normal group, the simple steatosis group, and the NASH positive group in two stages, the concentration factor of prediction for the NASH positive group is about 5, and thus a good discrimination capability is exhibited.

Although the invention has been described with respect to specific embodiments for a complete and clear disclosure, the appended claims are not to be thus limited but are to be construed as embodying all modifications and alternative constructions that may occur to one skilled in the art that fairly fall within the basic teaching herein set forth.

What is claimed is:

1. A method of evaluating fatty liver related disease, comprising:
evaluating, by a central processing unit ("CPU") executing a fatty liver related disease-evaluating program stored on a computer-readable recording medium, a state of a fatty liver related disease including at least one of fatty liver, NAFLD (non-alcoholic fatty liver disease), and NASH (non-alcoholic steatohepatitis) in a subject to be evaluated, based on amino acid concentration data on a concentration value of an amino acid in blood collected from the subject; wherein the fatty liver related disease-evaluating program is configured to evaluate the state of the NAFLD in the subject based on the concentration value of at least one of Gln, Pro, Gly, Ala, Cit, Leu, Val, Phe, Met, His, Trp, Orn, Ser, Thr, and Asn contained in the amino acid concentration data.

2. The method of evaluating fatty liver related disease according to claim 1, wherein the fatty liver related disease-evaluating program is further configured to evaluate the state of the NASH in the subject based on the concentration value of at least one of Gln, Glu, Pro, Gly, Ala, Leu, Ile, Val, Tyr, Phe, Met, His, Trp, Thr, Asn, and Ser contained in the amino acid concentration data.

3. The method of evaluating fatty liver related disease according to claim 2, wherein the fatty liver related disease-evaluating program is further configured to discriminate between the NASH and NASH-free based on the concentration value of at least one of Gln, Glu, Pro, Gly, Ala, Leu, Ile, Val, Tyr, Phe, Met, His, Trp, Thr, Asn, and Ser contained in the amino acid concentration data.

4. The method of evaluating fatty liver related disease according claim 1, wherein the fatty liver related disease-evaluating program is further configured to discriminate between the NAFLD and NAFLD-free in the subject based on the concentration value of at least one of Gln, Pro, Gly, Ala, Cit, Leu, Val, Phe, Met, His, Trp, Orn, Ser, Thr, and Asn contained in the amino acid concentration data.

5. The method of evaluating fatty liver related disease according to claim 1, wherein the fatty liver related disease-evaluating program is further configured to evaluate the state of the fatty liver in the subject based on the concentration value of at least one of Thr, Ser, Glu, Pro, Gly, Ala, Cit, Leu, Ile, Val, Tyr, Phe, Met, His, Trp, Asn, and Orn contained in the amino acid concentration data obtained at the obtaining step.

6. The method of evaluating fatty liver related disease according to claim 5, wherein the fatty liver related disease-evaluating program is further configured to discriminate between the fatty liver and fatty liver-free in the subject based on the concentration value of at least one of Thr, Ser, Glu, Pro, Gly, Ala, Cit, Leu, Ile, Val, Tyr, Phe, Met, His, Trp, Asn, and Orn contained in the amino acid concentration data.

7. The method of evaluating fatty liver related disease according to claim 1, wherein the fatty liver related disease-evaluating program is further configured to evaluate the states of the NASH and the NAFLD in the subject based on the concentration value of at least one of Gln, Glu, Gly, Ala, Cit, Asn, Trp, Leu, Orn, Phe, Met, Ile, Pro, and ABA contained in the amino acid concentration data.

8. The method of evaluating fatty liver related disease according to claim 7, wherein the fatty liver related disease-evaluating program is further configured to discriminate between the NASH and both of NASH-free and the NAFLD in the subject based on the concentration value of at least one of Gln, Glu, Gly, Ala, Cit, Asn, Trp, Leu, Orn, Phe, Met, Ile, Pro, and ABA contained in the amino acid concentration data.

9. The method of evaluating fatty liver related disease according to claim 1, wherein the fatty liver related disease-evaluating program is further configured to:
  evaluate the state of the fatty liver related disease in the subject based on a discriminant value that is a value of a multivariate discriminant containing a concentration of the amino acid as an explanatory variable, wherein the discriminant value is calculated based on the amino acid concentration data and the multivariate discriminant.

10. The method of evaluating fatty liver related disease according to claim 9, wherein the multivariate discriminant is any one of a logistic regression equation, a fractional expression, a linear discriminant, a multiple regression equation, a discriminant prepared by a support vector machine, a discriminant prepared by a Mahalanobis' generalized distance method, a discriminant prepared by canonical discriminant analysis, and a discriminant prepared by a decision tree.

11. The method of evaluating fatty liver related disease according to claim 9, wherein the fatty liver related disease-evaluating program is further configured to:
  calculate the discriminant value based on both (i) the concentration value of at least one of Gln, Glu, Pro, Gly, Ala, Leu, Ile, Val, Tyr, Phe, Met, His, Trp, Thr, Asn, and Ser contained in the amino acid concentration data and (ii) the multivariate discriminant containing at least one of Gln, Glu, Pro, Gly, Ala, Leu, Ile, Val, Tyr, Phe, Met, His, Trp, Thr, Asn, and Ser as the explanatory variable; and
  evaluate the state of the NASH in the subject based on the discriminant value.

12. The method of evaluating fatty liver related disease according to claim 11, wherein the fatty liver related disease-evaluating program is further configured to discriminate between the NASH and NASH-free in the subject based on the discriminant value.

13. The method of evaluating fatty liver related disease according to claim 12, wherein the multivariate discriminant is the logistic regression equation containing Glu, Gln, Gly, Ala, Val, and Tyr as the explanatory variables.

14. The method of evaluating fatty liver related disease according to claim 9, wherein the fatty liver related disease-evaluating program is further configured to:
  calculate the discriminant value based on both (i) the concentration value of at least one of Gln, Pro, Gly, Ala, Cit, Leu, Val, Phe, Met, His, Trp, Orn, Ser, Thr, and Asn contained in the amino acid concentration data obtained at the obtaining step and (ii) the multivariate discriminant containing at least one of Gln, Pro, Gly, Ala, Cit, Leu, Val, Phe, Met, His, Trp, Orn, Ser, Thr, and Asn as the explanatory variable; and
  evaluate the state of the NAFLD in the subject base on the discriminant value.

15. The method of evaluating fatty liver related disease according to claim 14, wherein the fatty liver related disease-evaluating program is further configured to discriminate between the NAFLD and NAFLD-free in the subject based on the discriminant value.

16. The method of evaluating fatty liver related disease according to claim 15, wherein the multivariate discriminant is the logistic regression equation containing Ser, Glu, Gly, Val, Tyr, and His as the explanatory variables.

17. The method of evaluating fatty liver related disease according to claim 9, wherein the fatty liver related disease-evaluating program is further configured to:
  calculate the discriminant value based on both (i) the concentration value of at least one of Thr, Ser, Glu, Pro, Gly, Ala, Cit, Leu, Ile, Val, Tyr, Phe, Met, His, Trp, Asn, and Orn contained in the amino acid concentration data and (ii) the multivariate discriminant containing at least one of Thr, Ser, Glu, Pro, Gly, Ala, Cit, Leu, Ile, Val, Tyr, Phe, Met, His, Trp, Asn, and Orn as the explanatory variable, and
  evaluate the state of the fatty liver in the subject based on the discriminant value.

18. The method of evaluating fatty liver related disease according to claim 17, wherein the fatty liver related disease-evaluating program is further configured to discriminate between the fatty liver and fatty liver-free in the subject based on the discriminant value.

19. The method of evaluating fatty liver related disease according to claim 18, wherein the multivariate discriminant is the logistic regression equation containing Ser, Glu, Gly, Ala, Val, and Tyr as the explanatory variables.

20. The method of evaluating fatty liver related disease according to claim 9, wherein the fatty liver related disease-evaluating program is further configured to:
  calculate the discriminant value based on both (i) the concentration value of at least one of Gln, Glu, Gly, Ala, Cit, Asn, Trp, Leu, Orn, Phe, Met, Ile, Pro, and ABA contained in the amino acid concentration data and (ii) the multivariate discriminant containing at least one of Gln, Glu, Gly, Ala, Cit, Asn, Trp, Leu, Orn, Phe, Met, Ile, Pro, and ABA as the explanatory variable, and
  evaluate the states of the NASH and the NAFLD in the subject based on the discriminant value.

21. The method of evaluating fatty liver related disease according to claim 20, wherein the fatty liver related disease-evaluating program is further configured to discriminate between the NASH and both of NASH-free and the NAFLD in the subject based on the discriminant value.

22. The method of evaluating fatty liver related disease according to claim 21, wherein the multivariate discriminant is the logistic regression equation containing Asn, Gln, Gly, Ala, Cit, and Met as the explanatory variables.

23. The method of evaluating fatty liver related disease according to claim 20, wherein the fatty liver related disease-evaluating program is further configured to discriminate between NAFLD-free, the NASH, and both of NASH-free and the NAFLD in the subject based on the discriminant value.

24. The method of evaluating fatty liver related disease according to claim 23, wherein the multivariate discriminant is the logistic regression equation containing Ser, Glu, Gly, Val, Tyr, and His as the explanatory variables and the logistic regression equation containing Asn, Gln, Gly, Ala, Cit, and Met as the explanatory variables.

25. A fatty liver related disease-evaluating apparatus comprising a CPU executing a fatty liver related disease-evaluating program stored on a computer readable recording medium, wherein the CPU is configured to:
  calculate a discriminant value that is a value of a multivariate discriminant containing a concentration of an amino acid as an explanatory variable, based on amino acid concentration data on a concentration value of the amino acid in blood of a subject to be evaluated and the multivariate discriminant for evaluating a state of a fatty liver related disease including at least one of fatty liver, NAFLD (non-alcoholic fatty liver disease), and NASH (non alcoholic steatohepatitis):

wherein the CPU is further configured to:
calculate the discriminant value based on both (i) the concentration value of at least one of Gln, Pro, Gly, Ala, Cit, Leu, Val, Phe, Met, His, Trp, Orn, Ser, Thr, and Asn contained in the amino acid concentration data and (ii) the multivariate discriminant for evaluating the state of NAFLD, wherein the multivariate discriminant contains at least one of Gln, Pro, Gly, Ala, Cit, Leu, Val, Phe, Met, His, Trp, Orn, Ser, Thr, and Asn as the explanatory variable.

26. The fatty liver related disease-evaluating apparatus according to claim 25,
wherein the CPU is further configured to evaluate the state of the fatty liver related disease in the subject based on the discriminant value,
wherein the CPU is further configured to evaluate the state of NAFLD based on the discriminant value.

27. A fatty liver related disease-evaluating method carried out with an information processing apparatus comprising a CPU executing a fatty liver related disease-evaluating program stored on a computer-readable recording medium, wherein the CPU is configured to:
calculate a discriminant value that is a value of a multivariate discriminant containing a concentration of an amino acid as an explanatory variable, based on amino acid concentration data on a concentration value of the amino acid in blood of a subject to be evaluated and the multivariate discriminant for evaluating a state of a fatty liver related disease including at least one of fatty liver, NAFLD (non-alcoholic fatty liver disease) and NASH (non alcoholic steatohepatitis),
wherein the CPU is further configured to:
calculate the discriminant value based on both (i) the concentration value of at least one of Gln, Pro, Gly, Ala, Cit, Leu, Val, Phe, Met, His, Trp, Orn, Ser, Thr, and Asn contained in the amino acid concentration data and (ii) the multivariate discriminant for evaluating the state of NAFLD, wherein the multivariate discriminant contains at least one of Gln, Pro, Gly, Ala, Cit, Leu, Val, Phe, Met, His, Trp, Orn, Ser, Thr, and Asn as the explanatory variable.

28. The fatty liver related disease-evaluating method according to claim 27,
wherein the CPU is further configured to evaluate the state of the fatty liver related disease in the subject based on the discriminant value,
wherein the CPU is further configured to evaluate the state of NAFLD based on the discriminant value.

29. A non-transitory computer-readable recording medium comprising a fatty liver related disease-evaluating program that is executed by a CPU, wherein the CPU if configured to:
calculate a discriminant value that is a value of a multivariate discriminant containing a concentration of an amino acid as an explanatory variable, based on amino acid concentration data a concentration value of the amino acid in blood of a subject to be evaluated and the multivariate discriminant for evaluating a state of a fatty liver related disease including at least one of fatty liver, NAFLD (non-alcoholic fatty liver disease), and NASH (non alcoholic steatohepatitis)
wherein the CPU is further configured to:
calculate the discriminant value based on both (i) the concentration value of at least one of Gln, Pro, Gly, Ala, Cit, Leu, Val, Phe, Met, His, Trp, Orn, Ser, Thr, and Asn contained in the amino acid concentration data and (ii) the multivariate discriminant for evaluating the state of NAFLD, wherein the multivariate discriminant contains at least one of Gln, Pro, Gly, Ala, Cit, Leu, Val, Phe, Met, His, Trp, Orn, Ser, Thr, and Asn as the explanatory variable.

30. The non-transitory computer-readable recording medium according to claim 29,
wherein the CPU is further configured to evaluate the state of the fatty liver related disease in the subject based on the discriminant value,
wherein the CPU is further configured to evaluate the state of NAFLD based on the discriminant value.

31. A fatty liver related disease-evaluating system comprising (I) a fatty liver related disease-evaluating apparatus comprising a CPU executing a fatty liver related disease-evaluating program stored on a computer readable recording medium, and (II) a terminal apparatus comprising a CPU executing a computer program stored on a computer-readable recording medium to provide amino acid concentration data on a concentration value of an amino acid in blood of a subject to be evaluated, wherein the apparatuses are connected to each other communicatively via a network,
wherein the CPU of the terminal apparatus is configured to:
transmit the amino acid concentration data of the subject to the fatty liver related disease-evaluating apparatus; and
receive a discriminant value that is a value of a multivariate discriminant containing a concentration of the amino acid as an explanatory variable or an evaluation result of the subject on a state of a fatty liver related disease including at least one of fatty liver, NAFLD (non-alcoholic fatty liver disease), and NASH (non alcoholic steatohepatitis), transmitted from the fatty liver related disease-evaluating apparatus, and
wherein the CPU of the fatty liver related disease-evaluating apparatus is configured to:
receive the amino acid concentration data transmitted from the terminal apparatus;
calculate the discriminant value based on the amino acid concentration data and the multivariate discriminant for evaluating a state of a fatty liver related disease including at least one of fatty liver, NAFLD (non-alcoholic fatty liver disease), and NASH (non alcoholic steatohepatitis) or;
calculate a discriminant value that is a value of a multivariate discriminant containing a concentration of the amino acid as an explanatory variable, based on the amino acid concentration data and the multivariate discriminant for evaluating the state of the fatty liver related disease, and evaluate the state of the fatty liver related disease based on the discriminant value; and
transmit the discriminant value or the evaluation result of the subject to the terminal apparatus,
wherein the CPU of the fatty liver related disease-evaluating apparatus is further configured to:
calculate the discriminant value based on both (i) the concentration value of at least one of Gln, Pro, Gly, Ala, Cit, Leu, Val, Phe, Met, His, Trp, Orn, Ser, Thr, and Asn contained in the amino acid concentration data and (ii) the multivariate discriminant for evaluating the state of NAFLD, wherein the multivariate discriminant contains at least one of Gln, Pro, Gly, Ala, Cit, Leu, Val, Phe, Met, His, Trp, Orn, Ser, Thr, and Asn as the explanatory variable or calculate the discriminant value based on both (i) the concentration value of at least one of Gln, Pro, Gly, Ala, Cit, Leu, Val, Phe, Met, His, Trp, Orn, Ser, Thr, and Asn contained in the amino acid concentration data and (ii) the multivariate discriminant for evaluating the state of NAFLD, wherein the multivariate discriminant contains at least one of Gln, Pro, Gly, Ala, Cit, Leu, Val, Phe, Met, His, Trp, Orn, Ser, Thr, and Asn as the explanatory variable, and evaluate the state of NAFLD based on the discriminant value.

32. A terminal apparatus comprising a CPU executing a computer program stored on a computer-readable recording medium, wherein the CPU is configured to:

obtain a discriminant value that is a value of a multivariate discriminant containing a concentration of an amino acid as an explanatory variable or an evaluation result of a subject to be evaluated on a state of a fatty liver related disease including at least one of fatty liver, NAFLD (non-alcoholic fatty liver disease), and NASH (non alcoholic steatohepatitis), wherein (I) the discriminant value is calculated based on amino acid concentration data on a concentration value of the amino acid in blood of a subject to be evaluated and the multivariate discriminant for evaluating a state of a fatty liver related disease including at least one of fatty liver NAFLD (non-alcoholic fatty liver disease), and NASH (nonalcoholic steatohepatitis) or (II) the evaluation result is the result of evaluating the state of the fatty liver related disease in the subject based on a discriminant value that is a value of a multivariate discriminant containing a concentration of an amino acid as an explanatory variable, wherein the discriminant value is calculated based on amino acid concentration data on a concentration value of the amino acid in blood of the subject and the multivariate discriminant for evaluating the state of the fatty liver related disease, wherein (I) the discriminant value is calculate based on both (i) the concentration value of at least one of Gln, Pro, Gly, Ala, Cit, Leu, Val, Phe, Met, His, Trp, Orn, Ser, Thr, and Asn contained in the amino acid concentration data and (ii) the multivariate discriminant for evaluating the state of NAFLD, wherein the multivariate discriminant contains at least one of Gln, Pro, Gly, Ala, Cit, Leu, Val, Phe, Met, His, Trp, Orn, Ser, Thr, and Asn as the explanatory variable or (II) the evaluation result is the result of evaluating the state of NAFLD in the subject based on the discriminant value, wherein the discriminant value is calculated based on both (i) the concentration value of at least one of Gln, Pro, Gly, Ala, Cit, Leu, Val, Phe, Met, His, Trp, Orn, Ser, Thr, and Asn contained in the amino acid concentration data and (ii) the multivariate discriminant for evaluating the state of NAFLD wherein the multivariate discriminant contains at least one of Gln, Pro, Gly, Ala, Cit, Leu, Val, Phe, Met, His, Trp, Orn, Ser, Thr, and Asn as the explanatory variable.

33. A fatty liver related disease-evaluating apparatus comprising a CPU executing a fatty liver related disease-evaluating program stored on a computer-readable recording medium, wherein the apparatus is connected communicatively via a network to a terminal apparatus configured to provide amino acid concentration data on a concentration value of an amino acid in blood of a subject to be evaluated, wherein the CPU is configured to:

receive the amino acid concentration data transmitted from the terminal apparatus;

calculate a discriminant value that is a value of a multivariate discriminant containing a concentration of the amino acid as an explanatory variable, based on the amino acid concentration data and the multivariate discriminant for evaluating a state of a fatty liver related disease including at least one of fatty liver, NAFLD (non-alcoholic fatty liver disease), and NASH (non alcoholic steatohepatitis) or;

calculate a discriminant value that is a value of a multivariate discriminant containing a concentration of the amino acid as an explanatory variable based on the amino acid concentration data and the multivariate discriminant for evaluating a state of a fatty liver related disease including at least one of fatty liver, NAFLD (non-alcoholic fatty liver disease), and NASH (non alcoholic steatohepatitis), and evaluate the state of the fatty liver related disease based on the discriminant value; and transmit the discriminant value or an evaluation result of the subject to the terminal apparatus wherein the CPU is further configured to:

calculate the discriminant value based on both (i) the concentration value of at least one of Gln, Pro, Gly, Ala, Cit, Leu, Val, Phe, Met, His, Trp, Orn, Ser, Thr, and Asn contained in the amino acid concentration data and (ii) the multivariate discriminant for evaluating the state of NAFLD, wherein the multivariate discriminant contains at least one of Gln, Pro, Gly, Ala, Cit, Leu, Val, Phe, Met, His, Trp, Orn, Ser, Thr, and Asn as the explanatory variable or calculate the discriminant value based on both (i) the concentration value of at least one of Gln, Pro, Gly, Ala, Cit, Leu, Val, Phe, Met, His, Trp, Orn, Ser, Thr, and Asn contained in the amino acid concentration data and (ii) the multivariate discriminant for evaluating the state of NAFLD, wherein the multivariate discriminant contains at least one of Gln, Pro, Gly, Ala, Cit, Leu, Val, Phe, Met, His, Trp, Orn, Ser, Thr, and Asn as the explanatory variable, and evaluate the state of NAFLD based on the discriminant value.

\* \* \* \* \*